United States Patent [19]

Fukuoka et al.

[11] Patent Number: 5,705,584

[45] Date of Patent: *Jan. 6, 1998

[54] PROPYLENE HOMOPOLYMER AND PROPYLENE COPOLYMER PREPARED USING NOVEL BRIDGED INDENYL-CONTAINING METALLOCENE

[75] Inventors: Daisuke Fukuoka; Takashi Tashiro; Koji Kawaai; Takashi Ueda; Yoshihisa Kiso; Akira Mizuno; Masaaki Kawasaki; Masaaki Itoh; Mikio Hashimoto, all of Waki-cho, Japan

[73] Assignee: Mitsui Petrochemical Industries, Ltd., Tokyo, Japan

[ * ] Notice: The term of this patent shall not extend beyond the expiration date of Pat. No. 5,504,172.

[21] Appl. No.: 477,647

[22] Filed: Jun. 7, 1995

Related U.S. Application Data

[62] Division of Ser. No. 255,706, Jun. 7, 1994, abandoned.

[30] Foreign Application Priority Data

| Jun. 7, 1993 | [JP] | Japan | 5-136253 |
| Sep. 24, 1993 | [JP] | Japan | 5-238561 |
| Oct. 6, 1993 | [JP] | Japan | 5-250742 |
| Nov. 29, 1993 | [JP] | Japan | 5-298744 |
| Nov. 29, 1993 | [JP] | Japan | 5-298745 |
| Feb. 23, 1994 | [JP] | Japan | 6-25548 |

[51] Int. Cl.[6] .................................... C08F 10/06
[52] U.S. Cl. .............. 526/348.2; 526/160; 526/348.6; 526/351; 526/943
[58] Field of Search ................ 526/351, 348.2, 526/348.6, 160, 943

[56] References Cited

U.S. PATENT DOCUMENTS

| 4,769,510 | 9/1988 | Kaminsky et al. |
| 4,990,640 | 2/1991 | Tsutsui et al. |
| 5,103,030 | 4/1992 | Rohrmann et al. |
| 5,243,001 | 9/1993 | Winter et al. |
| 5,278,264 | 1/1994 | Spaleck et al. ............ 526/127 |
| 5,329,033 | 7/1994 | Spaleck et al. |

FOREIGN PATENT DOCUMENTS

| 41491 | 1/1994 | Australia. |
| 0115940 | 8/1984 | European Pat. Off. |
| 0277003 | 8/1988 | European Pat. Off. |
| 0277004 | 8/1988 | European Pat. Off. |
| 426637 | 5/1991 | European Pat. Off. |
| 426638 | 5/1991 | European Pat. Off. |
| 427696 | 5/1991 | European Pat. Off. |

(List continued on next page.)

OTHER PUBLICATIONS

Patent Abstracts of Japan, vol. 7, No. 273 (C–198) 6 Dec. 1983 and JPA 82 033 049 (Mitsui Toatsu Kagaku) 9 Sep. 1983.

(List continued on next page.)

Primary Examiner—David W. Wu
Attorney, Agent, or Firm—Sherman and Shalloway

[57] ABSTRACT

The novel propylene homopolymer and copolymer produced by using a catalyst which is represented by the following formula (I):

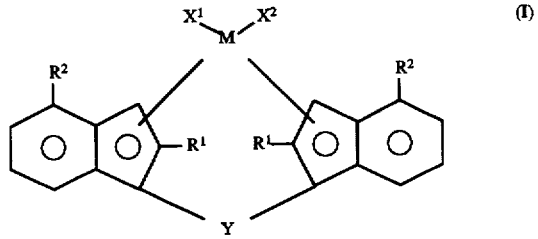

wherein M is a transition metal; $R^1$ is a hydrocarbon group of 2 to 6 carbon atoms, $R^2$ is an aryl group of 6 to 16 carbon atoms; $X^1$ and $X^2$ are each a halogen atom or the like; and Y is a divalent hydrocarbon group, a divalent silicon-containing group or the like.

2 Claims, 1 Drawing Sheet

FOREIGN PATENT DOCUMENTS

| | | |
|---|---|---|
| 427697 | 5/1991 | European Pat. Off. . |
| 0468651 | 1/1992 | European Pat. Off. . |
| 0472946 | 3/1992 | European Pat. Off. . |
| 0530647 | 3/1993 | European Pat. Off. . |
| 0546191 | 6/1993 | European Pat. Off. . |
| 0576970 | 1/1994 | European Pat. Off. . |
| 301704 | 12/1989 | Japan . |

OTHER PUBLICATIONS

Patent Abstracts of Japan, vol. 9, No. 228 (C-303) 13 Sep. 1985 and JPA 83 196 801 (Toray KK) 17 May 1985.

Journal of Organometallic Chemistry, 288, pp. 63–67 (1985).

Patent Abstracts of Japan, vol. 13, No. 236 (C-602) 30 May 1989 and JPA 87 202 317 (Toay Ind Inc) 17 Feb. 1989.

Journal of Molecular Catalysis, 56 (1989) pp. 237–247.

Polymer Preprints, Japan, vol. 39, No. 6 (1990) (No English Translation Available).

Hoechst Aktiengelesschaft at 40 YRS Ziegler Catalyst iho K. Ziegler Sep. (1993).

Macromolecular Chemistry and Physics, vol. 195, No. 4, Apr. 1994, Basel, pp. 1433–1441, XP439875 Fischer, D., "The Influence . . . Propylenes".

PROPYLENE HOMOPOLYMER AND PROPYLENE COPOLYMER PREPARED USING NOVEL BRIDGED INDENYL-CONTAINING METALLOCENE

This is a division of application Ser. No. 08/255,706 filed Jun. 7, 1994, now abandoned.

FIELD OF THE INVENTION

The present invention relates to a novel transition metal compound, an olefin polymerization catalyst component comprising the transition metal compound, an olefin polymerization catalyst containing the catalyst component and a process for olefin polymerization using the olefin polymerization catalyst. The invention also relates to a propylene homopolymer, a propylene copolymer and a propylene elastomer, all having a high triad tacticity of the propylene units chain, and low in an amount of inversely inserted propylene units.

BACKGROUND OF THE INVENTION

A well known homogeneous catalyst is, for example, so-called Kaminsky catalyst. Use of this Kaminsky catalyst produces a polymer having an extremely high polymerization activity and a narrow molecular weight distribution.

Of the Kaminsky catalysts, ethylenebis(indenyl) zirconium dichloride and ethylenebis(4,5,6,7-tetrahydroindenyl)zirconium dichloride are known as transition metal compounds for preparing isotactic polyolefins, as described in Japanese Patent Laid-Open Publication No. 130314/1986. However, polyolefins prepared by the use of these catalysts generally have a low stereoregularity and a low molecular weight. As a process for preparing polyolefins of high stereoregularity and high molecular weight using these catalyst, there is a process in which the polymerization is conducted at a low temperature, but this process has a problem of low polymerization activity.

It is known that use of hafnium compounds in place of the zirconium compounds makes it possible to prepare a polymer having high molecular weight, as described in "Journal of Molecular Catalysis", 56 (1989), pp. 237–247, but this process also has a problem of low polymerization activity. Further, dimethylsilyl bissubstituted cyclopentadienyl zirconium dichloride is also known as described in Japanese Patent Laid-Open Publication No. 301704/1989 and "Polymer Preprints", Japan, vol. 39, No. 6, pp. 1,614–1,616 (1990), but this compound is not satisfactory in all of polymerization activity, and stereoregularity and molecular weight of polymers obtained.

In order to solve these problems, various proposals have been made. For example, Japanese Patent Laid-Open Publication 268307/1993 describes an olefin polymerization catalyst formed from a metallocene compound represented by the following formula and aluminoxane as a catalyst capable of preparing a high molecular polyolefin.

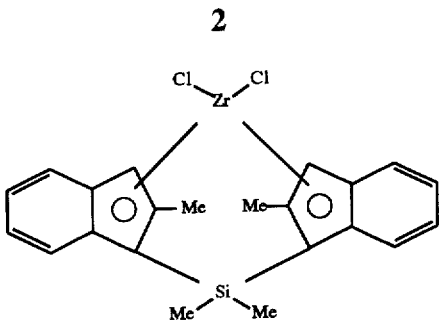

Further, EP 0 530 648 A1 describes an olefin polymerization catalyst formed from a metallocene compound represented by the following formula and aluminoxane.

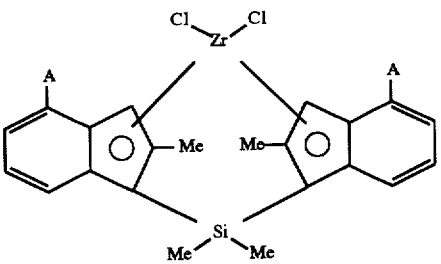

wherein A is a lower alkyl group.

However, the stereoregularity and the molecular weight of the polyolefin obtained by the use of these catalysts are not always satisfactorily, and the amount of inversely inserted units is still too large.

Moreover, a catalyst component (wherein, A is a phenyl group or naphthyl group in the aforementioned metallocene compound) is published from HOECHST AKTIENGESELLSCHAFT at 40 YEARS ZIEGLER CATALYST IN HONOR OF KARL ZIEGER AND WORKSHOP (SEP. 1–3, 1993).

Furthermore, EP 0 576 970 A1 describes an olefin polymerization catalyst formed from a metallocene compound represented by the following formula and an aluminoxane.

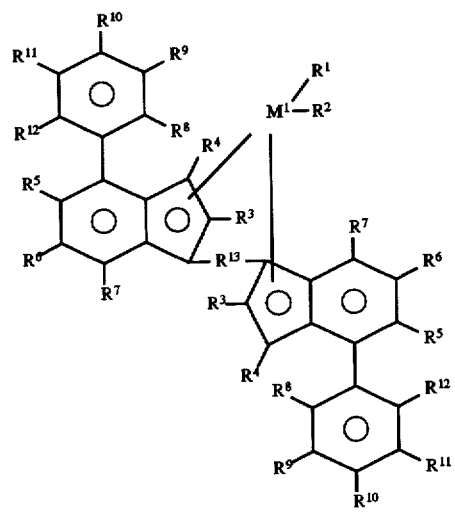

wherein $M^1$ is a transition metal atom, $R^1$ and $R^2$ are each a halogen atom, etc., $R^3$ is an alkyl group of 1 to 10 carbon atoms, etc., $R^4$ to $R^{12}$ are each an alkyl group of 1 to 10 carbon atoms etc., $R^{13}$ is a hydrocarbon group or a silicon containing group.

However, the stereoregularity of the polyolefin obtained by the use of these catalysts are not always satisfactorily, and the amount of inversely inserted units is still too large.

In the light of such prior arts as described above, the present inventors have found that polymerization activity of the catalyst component comprising the aforementioned transition metal compound is depending upon the kind of substituent on the indenyl group, and varied markedly in the stereoregularity and the amount of the inversely inserted units of the resulting polyolefin. Further, the inventors have also found that the transition metal compound having indenyl groups containing a specific substituent as a ligand is excellent olefin polymerization activity, and is capable of giving an olefin polymerization catalyst which provides an olefin polymer having high stereoregularity and low in the amount of inversely inserted units.

Propylene polymers, especially propylene homopolymers, have been applied to various uses such as industrial parts, containers, films and nonwoven fabrics, because of their excellent rigidity, surface hardness, heat resistance, glossiness and transparency.

However, the conventional propylene homopolymer is not always sufficient in transparency, impact resistance, etc. for some uses, and therefore the advent of a propylene polymer excellent in rigidity, heat resistance, surface hardness, glossiness, transparency and impact strength is desired.

Moreover, the physical properties of the copolymers of propylene and an α-olefin other than propylene vary depending on composition thereof, and hence the copolymers are generally distinguishable from each other bordering the monomer content derived from the α-olefin other than propylene of 5% by mol.

Propylene copolymers containing monomer units derived from α-olefin other than propylene in an amount of less than 5% by mol have been applied to various uses such as containers and packaging materials (e.g., films), because of their excellent rigidity, surface hardness, heat resistance, transparency and heat-sealing property. However, when the copolymer is used as a film, the resulting film is not always sufficient in transparency, heat-sealing property, anti-blocking property, anti-bleedout property and impact strength. Therefore, a propylene copolymer further improved in transparency, rigidity, surface hardness, heat resistance and heat-sealing property, and having excellent anti-blocking property, anti-bleedout property and impact strength is desired.

In contrast, propylene copolymers containing monomer units derived from α-olefin other than propylene in an amount of more than 5% by mol have been applied to various uses such as films, heat-sealing layers of laminated films, and modifiers for improving impact resistance and anti-heat-sealing property of thermoplastic resins, because of their excellent transparency, heat-sealing property at low temperature, environmental aging property and impact absorbing capacity. However, the conventional propylene copolymer is not always sufficient in transparency, heat-sealing properties at low temperature, anti-blocking properties, bleedout resistance, impact strength, etc. for some uses, and the modifiers therefrom are not always sufficient in effect of improving heat-sealing property at low temperature and impact strength. Therefore, there has been demanded a propylene copolymer further improved in transparency, environmental aging property and impact strength, and having excellent in effect of improving heat-sealing property at low temperature and impact strength.

In the light of such circumstances as described above, the present inventors have further studied, and as a result, they have found that a propylene homopolymer obtained by homopolymerization of propylene in the presence of an olefin polymerization catalyst containing a specific transition metal compound, and a propylene copolymer obtained by copolymerization of propylene and at least one kind of α-olefin selected from the group consisting of ethylene and α-olefins having 4 to 20 carbon atoms satisfy the above mentioned requisites.

A propylene/ethylene random copolymer containing a small amount of ethylene units is excellent in transparency, rigidity, surface hardness, heat resistance, and hence it is used for films, containers etc.

Heretofore, there is known some methods for preparation of the propylene/ethylene random copolymer containing a small amount of ethylene units, such as a method using a titanium catalyst system comprising a titanium compound and an organoaluminum compound and a method using a metallocene catalyst system comprising a metallocene compound (e.g., zirconocene and hafnocene) and an alkylaluminoxane or ionic compound.

However, the propylene/ethylene random copolymer obtained by using a titanium catalyst system is not always sufficient in heat-sealing property for some uses, and also insufficient in anti-blocking property, bleedout property and impact strength. On the other hand, the propylene/ethylene random copolymer obtained by using a metallocene catalyst system is not always sufficient in rigidity, surface hardness and heat resistance. Therefore, the advent of the propylene/ethylene random copolymer having advantages of the both, and excellent in balance of properties is demanded.

In the light of such circumstances as described above, the present inventors have further studied, and as a result, they have found that a propylene copolymer containing a specific amount of ethylene unit, having a high triad tacticity, as measured by $^{13}$C-NMR, of the propylene chain consisting of head-to-tail bonds, a specific proportion of inversely inserted propylene units and a specific intrinsic viscosity is excellent in transparency, rigidity, surface hardness, heat-sealing property, anti-blocking property, anti-bleedout property and impact strength.

Further, the propylene elastomer is excellent in impact absorbing capacity, heat resistance and heat-sealing property, it is singly used for films, and also is used for modifier for thermoplastic resin.

However, when the conventional propylene elastomer is singly used for films, the resulting films are not always sufficient in heat-sealing property, anti-blocking property and heat resistance. When the elastomer is used for modifier, the effect of improving impact strength is not always sufficient. Therefore, the advent of the propylene elastomer having excellent impact strength, and effective in improving heat resistance, transparency, heat-sealing property, anti-blocking resistance and impact resistance is demanded.

In the light of such circumstances as described above, the present inventors have further studied, and as a result, they have found that a propylene elastomer containing a specific amount of ethylene unit, having a high triad tacticity, as measured by $^{13}$C-NMR, of the propylene chain consisting of head-to-tail bonds, a specific proportion of inversely inserted propylene units and a specific intrinsic viscosity is excellent in above mentioned properties, and hence accomplished the present invention.

OBJECT OF THE INVENTION

It is an object of the present invention to provide a novel transition metal compound useful for an olefin polymerization catalyst component having a high olefin polymerization activity and capable of giving an olefin polymer having high stereoregularity and low in an amount of inversely inserted units, and to provide an olefin polymerization catalyst component comprising said transition metal compound.

It is another object of the invention to provide an olefin polymerization catalyst containing the above olefin polymerization catalyst component and to provide a process for olefin polymerization using said olefin polymerization catalyst.

It is a further object of the invention to provide a propylene homopolymer having excellent rigidity and transparency, a propylene copolymer having excellent impact strength and transparency, and propylene elastomer having excellent impact strength and transparency.

SUMMARY OF THE INVENTION

The novel transition metal compound according to the invention is a transition metal compound represented by the following formula (I):

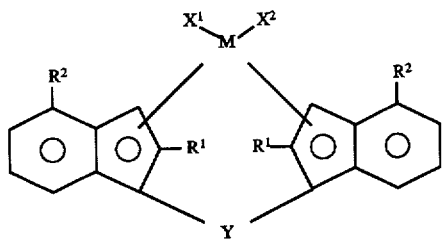

wherein

M is a transition metal of Group IVa, Group Va or Group VIa of the periodic table;

$R^1$ is a hydrocarbon group of 2 to 6 carbon atoms;

$R^2$ is an aryl group of 6 to 16 carbon atoms, which may be substituted with halogen atom, a hydrogen atom, a hydrocarbon group of 1 to 20 carbon atoms or an organosilyl group;

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group; and Y is a divalent hydrocarbon group of 1 to 20 carbon atoms, a divalent halogenated hydrocarbon group of 1 to 20 carbon atoms, a divalent silicon-containing group, a divalent germanium-containing group, —O—, —CO—, —S—, —SO—, —SO$_2$—, —NR$^3$—, —P(R$^3$)—, —P(O)(R$^3$)—, —BR$^3$— or —AlR$^3$— (R$^3$ is a hydrogen atom, a halogen atom, a hydrocarbon group of 1 to 20 carbon atoms or a halogenated hydrocarbon group of 1 to 20 carbon atoms).

The olefin polymerization catalyst component according to the invention comprises a transition metal compound represented by the above formula (I).

The first olefin polymerization catalyst according to the invention comprises:

(A) a transition metal compound represented by the above formula (I); and (B) at least one compound selected from the group consisting of (B-1) an organoaluminum oxy-compound, and (B-2) a compound which reacts with the transition metal compound to form an ion pair.

The second olefin polymerization catalyst according to the invention comprises:

(A) a transition metal compound represented by the above formula (I);

(B) at least one compound selected from the group consisting of (B-1) an organoaluminum oxy-compound, and (B-2) a compound which reacts with the transition metal compound to form an ion pair; and (C) an organoaluminum compound.

The third olefin polymerization catalyst according to the invention comprises:

a fine particle carrier;

(A) a transition metal compound represented by the above formula (I); and (B) at least one compound selected from the group consisting of (B-1) an organoaluminum oxy-compound, and (B-2) a compound which reacts with the transition metal compound to form an ion pair;

said transition metal compound (A) and said at least one compound (B) being supported on the fine particle carrier.

The fourth olefin polymerization catalyst according to the invention comprises:

a solid catalyst component comprising:

a fine particle carrier, (A) a transition metal compound represented by the above formula (I), and (B) at least one compound selected from the group consisting of (B-1) an organoaluminum oxy-compound, and (B-2) a compound which reacts with the transition metal compound to form an ion pair, said transition metal compound (A) and said at least one compound (B) being supported on the fine particle carrier; and (C) an organoaluminum compound.

The fifth olefin polymerization catalyst according to the invention comprises:

a fine particle carrier;

(A) a transition metal compound represented by the above formula (I);

(B) at least one compound selected from the group consisting of (B-1) an organoaluminum oxy-compound, and (B-2) a compound which reacts with the transition metal compound to form an ion pair; and a prepolymerized olefin polymer produced by prepolymerization.

The sixth olefin polymerization catalyst according to the invention comprises:

a fine particle carrier;

(A) a transition metal compound represented by the above formula (I);

(B) at least one compound selected from the group consisting of (B-1) an organoaluminum oxy-compound, and (B-2) a compound which reacts with the transition metal compound to form an ion pair;

(C) an organoaluminum compound; and a prepolymerized olefin polymer produced by prepolymerization.

The process for olefin polymerization according to the invention comprises polymerizing or copolymerizing an olefin in the presence of any of the first to sixth olefin polymerization catalysts.

The olefin polymerization catalysts according to the invention have high polymerization activity and an olefin polymer obtained by using the catalysts has a narrow molecular weight distribution, a narrow composition distribution and a large molecular weight. When they are used for polymerizing an α-olefin of 3 or more carbon atoms, obtainable is a polymer having high stereoregularity, low amount of inversely inserted units, and excellent in heat resistance and rigidity.

The first propylene homopolymer according to the present invention is obtained by polymerizing propylene in the presence of an olefin polymerization catalyst according to the invention comprising:

(A) a transition metal compound represented by the above formula (I); and (B) at least one compound selected from the group consisting of
(B-1) an organoaluminum oxy-compound, and
(B-2) a compound which reacts with the transition metal compound to form an ion pair.

The first propylene copolymer according to the present invention is obtained by copolymerizing propylene and at least one kind of α-olefin selected from the group consisting of ethylene and an α-olefin of 4 to 20 carbon atoms in the presence of an olefin polymerization catalyst according to the invention comprising:

(A) a transition metal compound represented by the above formula (I); and (B) at least one compound selected from the group consisting of
(B-1) an organoaluminum oxy-compound, and
(B-2) a compound which reacts with the transition metal compound to form an ion pair.

The propylene homopolymer of the present invention is excellent in rigidity, heat resistance, surface hardness, glossiness, transparency and impact strength.

The second propylene homopolymer according to the invention has such properties that:

(i) a triad tacticity of propylene units chain, as measured by $^{13}$C-NMR, is not less than 99.0%;

(ii) a proportion of inversely inserted propylene units based on the 2,1-insertion of a propylene monomer in all propylene insertions, as measured by $^{13}$C-NMR, is not more than 0.20%; and (iii) an intrinsic viscosity, as measured in decahydronaphthalene at 135° C., is in the range of 0.1 to 20 dl/g.

The propylene polymer of the present invention is excellent in rigidity, heat resistance, surface hardness, glossiness, transparency and impact resistance.

The second propylene copolymer according to the invention has such properties that:

(i) said copolymer contains ethylene units in an amount of not more than 50% by mol;

(ii) a triad tacticity of propylene units chain consisting of head-to-tail bonds, as measured by $^{13}$C-NMR, is not less than 98.0%;

(iii) a proportion of inversely inserted propylene units based on 2,1-insertion of a propylene monomer in all propylene insertions, as measured by $^{13}$C-NMR, is not more than 0.20%, and (iv) an intrinsic viscosity, as measured in decahydronaphthalene at 135° C., is in the range of 0.1 to 20 dl/g.

The propylene copolymer of the present invention (wherein the amount of monomer units derived from an α-olefin other than propylene is not more than 5% by mol) is excellent in transparency, rigidity, surface hardness, heat resistance, heat-sealing property, anti-blocking property, anti-bleedout property and impact strength. The propylene copolymer of the present invention (wherein the amount of monomer units derived from an α-olefin other than propylene is not less than 5% by mol) is excellent in transparency, environmental aging property, and effective in improving heat-sealing property at low temperature and impact strength.

The third propylene copolymer according to the invention has such properties that:

(i) said copolymer contains propylene units in an amount of 95 to 99.5% by mol and ethylene units in an amount of 0.5 to 5% by mol;

(ii) a triad tacticity of propylene units chain consisting of head-to-tail bonds, as measured by $^{13}$C-NMR, is not less than 95.0%;

(iii) a proportion of inversely inserted propylene units based on 2,1-insertion of a propylene monomer in all propylene insertions, as measured by $^{13}$C-NMR, of 0.05 to 0.5%, and (iv) an intrinsic viscosity, as measured in decahydronaphthalene at 135° C., is in the range of 0.1 to 12 dl/g.

The propylene copolymer of the present invention is excellent in rigidity, surface hardness, heat resistance, transparency, heat-sealing property, anti-blocking property and anti-bleedout property.

The propylene elastomer according to the invention has such properties that:

(i) said elastomer contains propylene units in an amount of 50 to 95% by mol and ethylene units in an amount of 5 to 50% by mol;

(ii) a triad tacticity of propylene units chain consisting of head-to-tail bonds, as measured by $^{13}$C-NMR, is not less than 90.0%;

(iii) a proportion of inversely inserted propylene units based on 2,1-insertion of a propylene monomer in all propylene insertions, as measured by $^{13}$C-NMR, of 0.05 to 0.5%; and (iv) an intrinsic viscosity, as measured in decahydronaphthalene at 135° C., is in the range of 0.1 to 12 dl/g.

The propylene elastomer of the present invention is excellent in heat resistance, impact absorbing capacity, transparency, heat-sealing properties and anti-blocking properties.

DETAILED DESCRIPTION OF THE INVENTION

Figure 1:
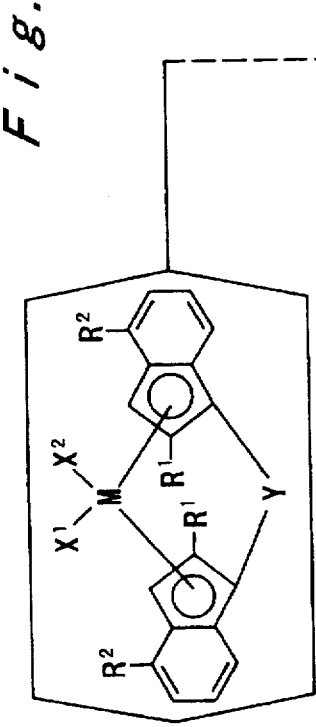
FIG. 1 is a view illustrating steps of a process for preparing the olefin polymerization catalysts according to the invention.

The novel transition metal compound, the olefin polymerization catalyst component comprising the transition metal compound, the olefin polymerization catalyst containing the olefin polymerization catalyst component, the process for olefin polymerization using the olefin polymerization catalyst, the propylene homopolymer, the propylene copolymer and the propylene elastomer, according to the invention, will be described in detail hereinafter.

FIG. 1 is a view illustrating steps of a process for preparing the olefin polymerization catalysts according to the invention.

First, the novel transition metal compound according to the invention is described.

The novel transition metal compound of the invention is a transition metal compound represented by the following formula (I).

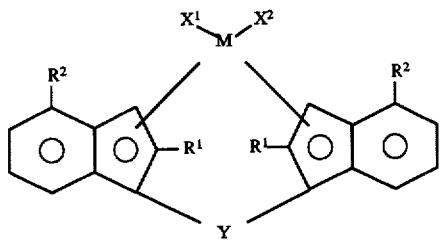

(I)

In the formula (I), M is a transition metal of Group IVa, Group Va or Group VIa of the periodic table. Examples of the transition metals include titanium, zirconium, hafnium, vanadium, niobium, tantalum, chromium, molybdenum and tungsten. Of these, titanium, zirconium and hafnium are preferred, and zirconium is particularly preferred.

$R^1$ is hydrocarbon group of 2 to 6 carbon atoms. Examples of the hydrocarbon groups of 2 to 6 carbon atoms include an alkyl group such as ethyl, n-propyl, isopropyl, n-butyl, isobutyl, sec-butyl, tert-butyl;, n-pentyl, neopentyl and n-hexyl; cycloalkyl group such as cyclohexyl; and an alkenyl group such as vinyl and propenyl.

Of these, preferred is an alkyl group wherein a carbon atom bonding to indenyl group is a primary carbon, more preferred is an alkyl group of 2 to 4 carbon atoms, particularly preferred is ethyl group.

$R^2$ is an aryl group of 6 to 16 carbon atoms. Examples of the aryl group of 6 to 16 carbon atoms include phenyl, α-naphthyl, β-naphthyl, anthracenyl, phenanthryl, pyrenyl, acenaphthyl, phenalenyl, aceanthrenyl, tetrahydronaphthyl, indanyl and biphenylyl. Of these, preferred is phenyl, naphthyl, anthracenyl or phenanthryl.

These aryl groups may be substituted with a halogen atom such as fluorine, chlorine, bromine or iodine;

a hydrocarbon group of 1 to 20 carbon atoms, for example an alkyl group such as methyl, ethyl, propyl, butyl, hexyl, cyclohexyl, octyl, nonyl, dodecyl, icosyl, norbornyl and adamantyl; an alkenyl group such as vinyl, propenyl and cyclohexenyl; arylalkyl group such as benzyl, phenylethyl and phenylpropyl; and an aryl group such as phenyl, tolyl, dimethylphenyl, trimethylphenyl, ethylphenyl, propylphenyl, biphenyl, naphthyl, methylnaphthyl, anthracenyl and phenanthryl; or an organo-silyl group such as trimethylsilyl, triethylsilyl and triphenylsilyl.

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group. Examples of those atoms and groups include the halogen atoms and the hydrocarbon groups of 1 to 20 carbon atoms as exemplified above. Examples of the halogenated hydrocarbon groups of 1 to 20 carbon atoms include the halogenated groups of the above mentioned hydrocarbon group of 1 to 20 carbon atoms.

Examples of the oxygen-containing groups include a hydroxy group; an alkoxy group such as methoxy, ethoxy, propoxy and butoxy; an aryloxy group such as phenoxy, methylphenoxy, dimethylphenoxy and naphthoxy; and an arylalkoxy group such as phenylmethoxy and phenylethoxy.

Examples of the sulfur-containing groups include groups obtained by substituting sulfur for oxygen in the above-mentioned oxygen-containing groups. As the sulfur-containing group, there can be also mentioned a sulfonato group such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzenesulfonato; and a sulfinato group such as methylsulfinato, phenylsulfinato, benzenesulfinato, p-toluenesulfinato, trimethylbenzenesulfinato and pentafluorobenzenesulfinato.

Of these, preferred is halogen atom or hydrocarbon group of 1 to 20 carbon atoms.

Y is a divalent hydrocarbon group of 1 to 20 carbon atoms, a divalent halogenated hydrocarbon group of 1 to 20 carbon atoms, a divalent silicon-containing group, a divalent germanium-containing group, —O—, —CO—, —S—, —SO—, —SO$_2$—, —NR$^3$—, —P(R$^3$)—, —P(O)(R$^3$)—, —BR$^3$— or —AlR$^3$— ($R^3$ is a hydrogen atom, a halogen atom, a hydrocarbon group of 1 to 20 carbon atoms or a halogenated hydrocarbon group of 1 to 20 carbon atoms).

Examples of the divalent hydrocarbon groups of 1 to 20 carbon atoms include an alkylene group such as methylene, dimethylmethylene, 1,2-ethylene, dimethyl-1,2-ethylene, 1,3-trimethylene, 1,4-tetramethylene; a cycloalkylene group such as 1,2-cyclohexylene and 1,4-cyclohexylene; and an arylalkylene group such as diphenylmethylene and diphenyl-1,2-ethylene.

Examples of the divalent halogenated hydrocarbon groups include groups obtained by halogenating the above-mentioned hydrocarbon groups of 1 to 20 carbon atoms, such as chloromethylene.

Examples of the divalent silicon-containing groups include an alkylsilylene group, an alkylarylsilylene group and an arylsilylene group, such as methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene and di(p-chlorophenyl)silylene; and an alkyldisilyl group, an alkylaryldisilyl group and an aryldisilyl group, such as tetramethyl-1,2-disilyl and tetraphenyl-1,2-disilyl.

Examples of the divalent germanium-containing groups include groups obtained by substituting germanium for silicon in the above-mentioned divalent silicon-containing groups.

Examples of the atoms and the groups indicated by $R^3$ include the halogen atoms, the hydrocarbon groups of 1 to 20 carbon atoms and the halogenated hydrocarbon groups of 1 to 20 carbon atoms exemplified above.

Of these, preferred are divalent silicon-containing group and divalent germanium-containing group, and particularly preferred are alkylsilylene, alkylarylsilylene and arylsilylene.

Listed below are examples of the transition metal compounds represented by the above formula (I).

rac-Dimethylsilyl-bis{1-(2-ethyl-4-phenylindenyl)}zirconium dichloride, rac-Dimethylsilyl-bis{1-(2-ethyl-4-(α-naphthyl)indenyl)}zirconium dichloride, rac-Dimethylsilyl-bis{1-(2-ethyl-4-(β-naphthyl)indenyl)}zirconium dichloride, rac-Dimethylsilyl-bis{1-(2-ethyl-4-(2-methyl-1-naphthyl)indenyl)}zirconium dichloride, rac-Dimethylsilyl-bis{1-(2-ethyl-4-(5-acenaphthyl)indenyl)}zirconium dichloride, rac-Dimethylsilyl-bis{1-(2-ethyl-4-(9-anthracenyl)indenyl)}zirconium dichloride, rac-Dimethylsilyl-bis{1-(2-ethyl-4-(9-phenanthryl)indenyl)}zirconium dichloride, rac-Dimethylsilyl-bis{1-(2-ethyl-4-(o-methylphenyl) indenyl)}zirconium dichloride,
rac-Dimethylsilyl-bis{1-(2-ethyl-4-(m-methylphenyl) indenyl)}zirconium dichloride,
rac-Dimethylsilyl-bis{1-(2-ethyl-4-(p-methylphenyl) indenyl)}zirconium dichloride,
rac-Dimethylsilyl-bis{1-(2-ethyl-4-(2,3-dimethylphenyl) indenyl)}zirconium dichloride,
rac-Dimethylsilyl-bis{1-(2-ethyl-4-(2,4-dimethylphenyl) indenyl)}zirconium dichloride,
rac-Dimethylsilyl-bis{1-(2-ethyl-4-(2,5-dimethylphenyl) indenyl)}zirconium dichloride,
rac-Dimethylsilyl-bis{1-(2-ethyl-4-(2,4,6-trimethylphenyl)indenyl)}zirconium dichloride,
rac-Dimethylsilyl-bis{1-(2-ethyl-4-(o-chlorophenyl) indenyl)}zirconium dichloride,
rac-Dimethylsilyl-bis{1-(2-ethyl-4-(m-chlorophenyl) indenyl)}zirconium dichloride,
rac-Dimethylsilyl-bis{1-(2-ethyl-4-(p-chlorophenyl) indenyl)}zirconium dichloride,
rac-Dimethylsilyl-bis{1-(2-ethyl-4-(2,3-dichlorophenyl) indenyl)}zirconium dichloride,
rac-Dimethylsilyl-bis{1-(2-ethyl-4-(2,6-dichlorophenyl) indenyl)}zirconium dichloride,
rac-Dimethylsilyl-bis{1-(2-ethyl-4-(3,5-dichlorophenyl) indenyl)}zirconium dichloride,
rac-Dimethylsilyl-bis{1-(2-ethyl-4-(2-bromophenyl) indenyl)}zirconium dichloride,
rac-Dimethylsilyl-bis{1-(2-ethyl-4-(3-bromophenyl) indenyl)}zirconium dichloride,
rac-Dimethylsilyl-bis{1-(2-ethyl-4-(4-bromophenyl) indenyl)}zirconium dichloride,
rac-Dimethylsilyl-bis{1-(2-ethyl-4-(4-biphenyl)indenyl) }zirconium dichloride,
rac-Dimethylsilyl-bis{1-(2-ethyl-4-(4-trimethylsilylphenyl)indenyl)}zirconium dichloride,
rac-Dimethylsilyl-bis{1-(2-n-propyl-4phenylindenyl) }zirconium dichloride,
rac-Dimethylsilyl-bis{1-(2-n-propyl-4-(α-naphthyl) indenyl)}zirconium dichloride,
rac-Dimethylsilyl-bis{1-(2-n-propyl-4-(β-naphthyl) indenyl)}zirconium dichloride,
rac-Dimethylsilyl-bis{1-(2-n-propyl-4-(2-methyl-1-naphthyl)indenyl)}zirconium dichloride,
rac-Dimethylsilyl-bis{1-(2-n-propyl-4-(5-acenaphthyl) indenyl)}zirconium dichloride,
rac-Dimethylsilyl-bis{1-(2-n-propyl-4-(9-anthracenyl) indenyl)}zirconium dichloride,
rac-Dimethylsilyl-bis{1-(2-n-propyl-4-(9-phenanthryl) indenyl)}zirconium dichloride,
rac-Dimethylsilyl-bis{t-(2-i-propyl-4phenylindenyl) }zirconium dichloride,
rac-Dimethylsilyl-bis{1-(2-i-propyl-4-(α-naphthyl) indenyl)}zirconium dichloride,
rac-Dimethylsilyl-bis{1-(2-i-propyl-4-(β-naphthyl) indenyl)}zirconium dichloride,
rac-Dimethylsilyl-bis{1-(2-i-propyl-4-(8-methyl-9-naphthyl)indenyl)}zirconium dichloride,
rac-Dimethylsilyl-bis{1-(2-i-propyl-4-(5-acenaphthyl) indenyl)}zirconium dichloride,
rac-Dimethylsilyl-bis{1-(2-i-propyl-4-(9-anthracenyl) indenyl)}zirconium dichloride,
rac-Dimethylsilyl-bis{1-(2-i-propyl-4-(9-phenanthryl) indenyl)}zirconium dichloride,
rac-Dimethylsilyl-bis{1-(2-s-butyl-4-phenylindenyl) }zirconium dichloride,
rac-Dimethylsilyl-bis{1-(2-s-butyl-4-(α-naphthyl) indenyl)}zirconium dichloride,
rac-Dimethylsilyl-bis{1-(2-s-butyl-4-(β-naphthyl) indenyl)}zirconium dichloride,
rac-Dimethylsilyl-bis{1-(2-s-butyl-4-(2-methyl-1-naphthyl)indenyl)}zirconium dichloride,
rac-Dimethylsilyl-bis{1-(2-s-butyl-4-(5-acenaphthyl) indenyl)}zirconium dichloride,
rac-Dimethylsilyl-bis{1-(2-s-butyl-4-(9-anthracenyl) indenyl)}zirconium dichloride,
rac-Dimethylsilyl-bis{1-(2-s-butyl-4-(9-phenanthryl) indenyl)}zirconium dichloride,
rac-Dimethylsilyl-bis{1-(2-n-pentyl-4-(9-phenylindenyl) }zirconium dichloride,
rac-Dimethylsilyl-bis{1-(2-n-pentyl-4-(α-naphthyl) indenyl)}zirconium dichloride,
rac-Dimethylsilyl-bis{1-(2-n-butyl-4-phenylindenyl) }zirconium dichloride,
rac-Dimethylsilyl-bis{1-(2-n-butyl-4-(α-naphthyl) indenyl)}zirconium dichloride,
rac-Dimethylsilyl-bis{1-(2-n-butyl-4-(β-naphthyl) indenyl)}zirconium dichloride,
rac-Dimethylsilyl-bis{1-(2-n-butyl-4-(2-methyl-1-naphthyl)indenyl)}zirconium dichloride,
rac-Dimethylsilyl-bis{1-(2-n-butyl-4-(5-acenaphthyl) indenyl)}zirconium dichloride,
rac-Dimethylsilyl-bis{1-(2-n-butyl-4-(9-anthracenyl) indenyl)}zirconium dichloride,
rac-Dimethylsilyl-bis{1-(2-n-butyl-4-(9-phenanthryl) indenyl)}zirconium dichloride,
rac-Dimethylsilyl-bis{1-(2-i-butyl-4-phenylindenyl) }zirconium dichloride,
rac-Dimethylsilyl-bis{1-(2-i-butyl-4-(α-naphthyl) indenyl)}zirconium dichloride,
rac-Dimethylsilyl-bis{1-(2-i-butyl-4-(β-naphthyl) indenyl)}zirconium dichloride,
rac-Dimethylsilyl-bis{1-(2-i-butyl-4-(2-methyl-1-naphthyl)indenyl)}zirconium dichloride,
rac-Dimethylsilyl-bis{1-(2-i-butyl-4-(5-acenaphthyl) indenyl)}zirconium dichloride,
rac-Dimethylsilyl-bis{1-(2-i-butyl-4-(9-anthracenyl) indenyl)}zirconium dichloride,
rac-Dimethylsilyl-bis{1-(2-i-butyl-4-(9-phenanthryl) indenyl)}zirconium dichloride,
rac-Dimethylsilyl-bis{1-(2-neopentyl-4-phenylindenyl) }zirconium dichloride,
rac-Dimethylsilyl-bis{1-(2-neopentyl-4-(α-naphthyl) indenyl)}zirconium dichloride,
rac-Dimethylsilyl-bis{1-(2-n-hexyl-4-phenylindenyl) }zirconium dichloride,
rac-Dimethylsilyl-bis{1-(2-n-hexyl-4-(α-naphthyl) indenyl)}zirconium dichloride,
rac-methylphenylsilyl-bis{1-(2-ethyl-4-(α-naphthyl) indenyl)}zirconium dichloride,
rac-methylphenylsilyl-bis{1-(2-ethyl-4-(9-anthracenyl) indenyl)}zirconium dichloride,
rac-methylphenylsilyl-bis{1-(2-ethyl-4-(9-phenanthryl) indenyl)}zirconium dichloride, rac-diphenylsilyl-bis{1-(2-ethyl-4-phenylindenyl)}zirconium dichloride, rac-diphenylsilyl-bis{1-(2-ethyl-4-(α-naphthyl)indenyl)}zirconium dichloride, rac-diphenylsilyl-bis{1-(2-ethyl-4-(9-anthracenyl)indenyl)}zirconium dichloride, rac-diphenylsilyl-bis{1-(2-ethyl-4-(9-phenanthryl)indenyl)}zirconium dichloride, rac-diphenylsilyl-bis{1-(2-ethyl-4-(4-biphenyl)indenyl)}zirconium dichloride, rac-methylene-bis{1-(2-ethyl-4-phenylindenyl)}zirconium dichloride, rac-methylene-bis{1-(2-ethyl-4-(α-naphthyl)indenyl)}zirconium dichloride, rac-ethylene-bis{1-(2-ethyl-4-phenylindenyl)}zirconium dichloride, rac-ethylene-bis{1-(2-ethyl-4-(α-naphthyl)indenyl}zirconium dichloride, rac-ethylene-bis{1-(2-n-propyl-4-(α-naphthyl)indenyl)}zirconium dichloride, rac-dimethylgermyl-bis{1-(2-ethyl-4-phenylindenyl)}zirconium dichloride, rac-dimethylgermyl-bis{1-(2-ethyl-4-(α-naphthyl)indenyl)}zirconium dichloride, and rac-dimethylgermyl-bis{1-(2-n-propyl-4-phenylindenyl)}zirconium dichloride.

There may also be used the transition metal compounds obtained by substituting vanadium metal, niobium metal, tantalum metal, chromium metal, molybdenum metal or tungsten metal for zirconium metal, titanium metal or hafnium metal in the above-exemplified compounds.

The transition metal compounds according to the present invention can be prepared in accordance with the methods described in Journal of Organometallic Chem. 288 (1985), pages 63 to 67, European Patent Publication No. 0,320,762 specification and Examples thereof, for instance, by the following manner.

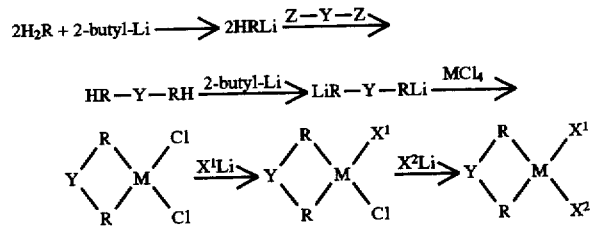

wherein, Z represents Cl, Br, I or o-tosyl group, and $H_2R$ represents

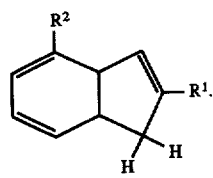

The novel transition metal compound according to the present invention can be used as an olefin polymerization catalyst in combination with an organoaluminum oxy-compound.

The novel transition metal compound is used as an olefin polymerization catalyst component in the form of usually a racemic modification, but the R configuration or the S configuration can be also used.

Next, the olefin polymerization catalyst containing the above-mentioned novel transition metal compound as its catalyst component is described.

The meaning of the term "polymerization" used herein is not limited to "homopolymerization" but may comprehend "copolymerization". Also, the meaning of the term "polymer" used herein is not limited to "homopolymer" but may comprehend "copolymer".

The first and the second olefin polymerization catalysts according to the invention are described below.

The first olefin polymerization catalyst of the invention is formed from:

(A) a transition metal compound represented by the above formula (I) (sometimes referred to as "component (A)" hereinafter); and (B) at least one compound selected from the group consisting of (B-1) an organoaluminum oxy-compound, and (B-2) a compound which reacts with the transition metal compound to form an ion pair.

The second olefin polymerization catalyst of the invention is formed from:

(A) a transition metal compound represented by the above formula (I);

(B) at least one compound selected from the group consisting of (B-1) an organoaluminum oxy-compound, and (B-2) a compound which reacts with the transition metal compound to form an ion pair; and (C) an organoaluminum compound.

The organoaluminum oxy-compound (B-1) (hereinafter sometimes referred to as "component (B-1)") used for the first and the second olefin polymerization catalysts of the invention may be a conventionally known aluminoxane or may be a benzene-insoluble organoaluminum oxy-compound as described in Japanese Patent Laid-Open Publication No. 78687/1990.

The conventionally known aluminoxane can be prepared, for example, by the following processes.

(1) A process comprising allowing an organoaluminum compound such as trialkylaluminum to react with a suspension of a compound having adsorbed water or a salt containing water of crystallization, for example, hydrate of magnesium chloride, copper sulfate, aluminum sulfate, nickel sulfate or cerous chloride in a hydrocarbon solvent.

(2) A process comprising allowing water, ice or water vapor to directly react with an organoaluminum compound such as trialkylaluminum in a solvent such as benzene, toluene, ethyl ether and tetrahydrofuran.

(3) A process comprising allowing an organotin oxide such as dimethyltin oxide and dibutyltin oxide to react with an organoaluminum compound such as trialkylaluminum in a solvent such as decane, benzene and toluene.

The aluminoxane may contain a small amount of an organometallic component. Moreover, the solvent or the unreacted organoaluminum compound may be distilled off from the recovered solution of aluminoxane described above, and the resultant product may be dissolved again in a solvent.

Examples of the organoaluminum compounds used for preparing aluminoxane include:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum;

tricycloalkylaluminums, such as tricyclohexylaluminum and tricyclooctylaluminum;

dialkylaluminum halides, such as dimethylaluminum chloride, diethylaluminum chloride, diethylaluminum bromide and diisobutylaluminum chloride;

dialkylaluminum hydrides, such as diethylaluminum hydride and diisobutylaluminum hydride;

dialkylaluminum alkoxides, such as dimethylaluminum methoxide and diethylaluminum ethoxide; and dialkylaluminum aryloxides, such as diethylaluminum phenoxide.

Of the organoaluminum compounds, trialkylaluminum and tricycloalkylaluminum are particularly preferred.

Further, there may be also used, as the organoaluminum compound for preparing aluminoxane, isoprenylaluminum represented by the following formula (II):

(II)

wherein x, y and z are each a positive number, and $z \geq 2x$.

The organoaluminum compounds mentioned above may be used singly or in combination.

Solvents used for preparing aluminoxane include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosine and gas oil; and halides of the above-mentioned aromatic, aliphatic and alicyclic hydrocarbons, particularly chlorides and bromides thereof. In addition thereto, ethers such as ethyl ether and tetrahydrofuran may be also used. Of these solvents, particularly preferred are aromatic hydrocarbons.

Examples of the compounds which react with the transition metal compound (A) to form an ion pair (hereinafter sometimes referred to as "component (B-2)"), which are used for the first and the second olefin polymerization catalysts, include Lewis acid, ionic compounds, borane compounds and carborane compounds, as described in National Publications of International Patent No. 501950/1989 and No. 502036/1989, Japanese Patent Laid-Open Publications No. 179005/1992, No. 179006/1992, No. 207703/1992 and No. 207704/1992, and U.S. Pat. No. 547,718.

The Lewis acid includes Mg-containing Lewis acid, Al-containing Lewis acid and B-containing Lewis acid. Of these, B-containing Lewis acid is preferred.

The Lewis acid containing a boron atom (B-containing Lewis acid) is, for example, a compound represented by the following formula:

$BR^6R^7R^8$ wherein $R^6$, $R^7$ and $R^8$ are each independently a phenyl group which may have a substituent such as a fluorine atom, a methyl group and a trifluoromethyl group, or a fluorine atom.

Examples of the compounds represented by the above formula include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron. Of these, tris(pentafluorophenyl)boron is particularly preferred.

The ionic compound used in the invention is a salt comprising a cationic compound and an anionic compound. An anion reacts with the transition metal compound (A) to make the transition metal compound (A) cationic and to form an ion pair so as to stabilize the transition metal cation seed. Examples of such anions include organoboron compound anion and organoarsenic compound anion, organoaluminum compound anion. Preferred is such anion as is relatively bulky and stabilizes the transition metal cation seed. Examples of cations include metallic cation, organometallic cation, carbonium cation, tripium cation, oxonium cation, sulfonium cation, phosphonium cation and ammonium cation. More specifically, there can be mentioned triphenylcarbenium cation, tributylammonium cation, N,N-dimethylammonium cation and ferrocenium cation.

Of these, preferred are ionic compounds containing a boron compound as anion. More specifically, examples of trialkyl-substituted ammonium salts include triethylammoniumtetra(phenyl)boron, tripropylammoniumtetra(phenyl)boron, tri(n-butyl)ammoniumtetra(phenyl)boron, trimethylammoniumtetra(p-tolyl)boron, trimethylammoniumtetra(o-tolyl)boron, tributylammoniumtetra(pentafluorophenyl)boron, tripropylammoniumtetra(o,p-dimethylphenyl)boron, tributylammoniumtetra(m,m-dimethylphenyl)boron, tributylammoniumtetra(p-trifluoromethylphenyl)boron, tri (n-butyl) ammoniumtetra(o-tolyl)boron and tri (n-butyl) ammoniumtetra(4-fluorophenyl)boron.

Examples of N,N-dialkylanilinium salts include

N,N-dimethylaniliniumtetra(phenyl)boron,

N,N-diethylaniliniumtetra(phenyl)boron and

N,N-2,4,6-pentamethylaniliniumtetra(phenyl)boron.

Examples of dialkylammonium salts include di(n-propyl)ammoniumtetra(pentafluorophenyl)boron and dicyclohexylammoniumtetra(phenyl)boron.

Examples of triarylphosphonium salts include triphenylphosphoniumtetra(phenyl)boron, tri(methylphenyl)phosphoniumtetra(phenyl)boron and tri(dimethylphenyl)phosphoniumtetra(phenyl)boron.

Also employable as the ionic compound containing a boron atom are triphenylcarbeniumtetrakis-(pentafluorophenyl)borate, N,N-dimethylaniliniumtetrakis(pentafluorophenyl)borate and ferroceniumtetrakis(pentafluorophenyl)borate.

Further, the following compounds can be also employed. (In the ionic compounds enumerated below, the counter ion is tri(n-butyl)ammonium, but the counter ion is in no way limited thereto.)

That is, there can be mentioned salts of anion, for example, bis{tri(n-butyl)ammonium}nonaborate, bis{tri(n-butyl)ammonium}decaborate, bis{tri(n-butyl)ammonium}undecaborate, bis{tri(n-butyl)ammonium}dodecaborate, bis{tri(n-butyl)ammonium}decachlorodecaborate, bis{tri(n-butyl)ammonium}dodecachlorododecaborate, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate and tri(n-butyl)ammoniumbromo-1-carbadecaborate.

Moreover, borane compounds and carborane compounds can be also employed. These compounds are employed as the Lewis acid or the ionic compounds.

Examples of the borane compounds and the carborane compounds include:

borane and carborane complex compounds and salts of carborane anion, for example,
decaborane(number of hydrogen=14),
7,8-dicarbaundecaborane(13),
2,7-dicarbaundecaborane(13),
undecahydride-7,8-dimethyl-7,8-dicarbaundecaborane,
dodecahydride-11-methyl-2,7-dicarbaundecaborane,
tri(n-butyl)ammonium-6-carbadecaborate(14),
tri(n-butyl)ammonium-6-carbadecaborate(12),
tri(n-butyl)ammonium-7-carbaundecaborate(13),
tri(n-butyl)ammonium-7,8-dicarbaundecaborate(12),
tri(n-butyl)ammonium-2,9-dicarbaundecaborate(12),
tri(n-butyl)ammoniumdodecahydride-8-methyl-7,9-dicarbaundecaborate,
tri(n-butyl)ammoniumundecahydride-8-ethyl-7,9-dicarbaundecaborate,
tri(n-butyl)ammoniumundecahydride-8-butyl-7,9-dicarbaundecaborate,
tri(n-butyl)ammoniumundecahydride-8-allyl-7,9-dicarbaundecaborate,
tri(n-butyl)ammoniumundecahydride-9-trimethylsilyl-7,8-dicarbaundecaborate and
tri(n-butyl)ammoniumundecahydride-4,6-dibromo-7-carbaundecaborate; and carborane and salts of carborane, for example,
4-carbanonaborane(14), 1,3-dicarbanonaborane (13), 6,9-dicarbadecaborane (14),
dodecahydride-1-phenyl-1,3-dicarbanonaborane,
dodecahydride-1-methyl-1,3-dicarbanonaborane and
undecahydride-1,3-dimethyl-1,3-dicarbanonaborane.

Furthermore, the following compounds can be also employed. (In the ionic compounds enumerated below, the counter ion is tri(n-butyl)ammonium, but the counter ion is in no way limited thereto.)

That is, there can be mentioned salts of metallic carborane and metallic borane anion, for example,
tri(n-butyl)ammoniumbis(nonahydride-1,3-dicarbononaborate)cobaltate(III),
tri(n-butyl)ammoniumbis(undecahydride-7,8-dicarbaundecaborate)ferrate(III),
tri(n-butyl)ammoniumbis(undecahydride-7,8-dicarbaundecaborate)cobaltate(III),
tri(n-butyl)ammoniumbis(undecahydride-7,8-dicarbaundecaborate)nickelate(III),
tri(n-butyl)ammoniumbis(undecahydride-7,8-dicarbaundecaborate)cuprate(III),
tri(n-butyl)ammoniumbis(undecahydride-7,8-dicarbaundecaborate)aurate(III),
tri(n-butyl)ammoniumbis(nonahydride-7,8-dimethyl-7,8-dicarbaundecaborate)ferrate(III),
tri(n-butyl)ammoniumbis(nonahydride-7,8-dimethyl-7,8-dicarbaundecaborate)chromate(III),
tri(n-butyl)ammoniumbis(tribromooctahydride-7,8-dicarbaundecaborate)cobaltate(III),
tri(n-butyl)ammoniumbis(dodecahydridedicarbadodecaborate)cobaltate(III),
bis{tri(n-butyl)ammonium}bis(dodecahydridedodecaborate)nickelate(III),
tris{tri(n-butyl)ammonium}bis(undecahydride-7-carbaundecaborate)chromate(III),
bis{tri(n-butyl)ammonium}bis(undecahydride-7-carbaundecaborate)manganate(IV),
bis{tri(n-butyl)ammonium}bis(undecahydride-7-carbaundecaborate)cobaltate(III) and
bis{tri(n-butyl)ammonium}bis(undecahydride-7-carbaundecaborate)nickelate(IV).

The compounds (B-2) which react with the transition metal compound (A) to form an ion pair can be used in combination of two or more kinds.

The organoaluminum compound (C) (hereinafter sometimes referred to as "component (C)") used for the second olefin polymerization catalyst of the invention is, for example, an organoaluminum compound represented by the following formula (III):

$$R^9_n AlX_{3-n} \quad (III)$$

wherein $R^9$ is a hydrocarbon group of 1 to 12 carbon atoms, X is a halogen atom or a hydrogen atom, and n is 1 to 3.

In the above formula (III), $R^9$ is a hydrocarbon group of 1 to 12 carbon atoms, e.g., an alkyl group, a cycloalkyl group or an aryl group. Particular examples thereof include methyl, ethyl, n-propyl, isopropyl, isobutyl, pentyl, hexyl, octyl, cyclopentyl, cyclohexyl, phenyl and tolyl.

Examples of such organoaluminum compounds (C) include:

trialkylaluminums, such as trimethylaluminum, triethylaluminum, triisopropylaluminum, triisobutylaluminum, trioctylaluminum and tri(2-ethylhexyl)aluminum;

alkenylaluminums, such as isoprenylaluminum, dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichloride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylaluminum dichloride and ethylaluminum dibromide; and alkylaluminum hydrides, such as diethylaluminum hydride and diisobutylaluminum hydride.

Also employable as the organoaluminum compound (C) is a compound represented by the following formula (IV):

$$R^9_n AlL_{3-n} \quad (IV)$$

wherein $R^9$ is the same hydrocarbon as in the above formula (III); L is —$OR^{10}$ group, —$OSiR^{11}_3$ group, —$OAlR^{12}_2$ group, $NR^{13}_2$ group, —$SiR^{14}_3$ group or —$N(R^{15})AlR^{16}_2$ group; n is 1 to 2; $R^{10}$, $R^{11}$, $R^{12}$ and $R^{16}$ are each methyl, ethyl, isopropyl, isobutyl, cyclohexyl, phenyl or the like; $R^{13}$ is hydrogen, methyl, ethyl, isopropyl, phenyl, trimethylsilyl or the like; and $R^{14}$ and $R^{15}$ are each methyl, ethyl or the like.

Examples of such organoaluminum compounds (C) include:

(1) compounds represented by the formula $R^9_n Al (OR^{10})_{3-n}$, for example, dimethylaluminum methoxide, diethylaluminum ethoxide and diisobutylaluminum methoxide;

(2) compounds represented by the formula $R^9_n Al (OSiR^{11}_3)_{3-n}$, for example, $Et_2Al(OSiMe_3)$, (iso-Bu)$_2Al(OSiMe_3)$ and (iso-Bu)$_2Al(OSiEt_3)$;

(3) compounds represented by the formula $R^9{}_nAl(OAlR^{12}{}_2)_{3-n}$, for example, $Et_2AlOAlEt_2$ and $(iso\text{-}Bu)_2AlOAl(iso\text{-}Bu)_2$;

(4) compounds represented by the formula $R^9{}_nAl(NR^{13}{}_2)_{3-n}$, for example, $Me_2AlNEt_2$, $Et_2AlNHMe$, $Me_2AlNHEt$, $Et_2AlN(SiMe_3)_2$ and $(iso\text{-}Bu)_2AlN(SiMe_3)_2$;

(5) compounds represented by the formula $R^9{}_nAl(SiR^{14}{}_3)_{3-n}$, for example, $(iso\text{-}Bu)_2AlSiMe_3$; and (6) compounds represented by the formula $R^9{}_nAl(N(R^{15})AlR^{16}{}_2)_{3-n}$, for example, $Et_2AlN(Me)AlEt_2$ and $(iso\text{-}Bu)_2AlN(Et)Al(iso\text{-}B)_2$.

Of the organoaluminum compounds represented by the formulas (III) and (IV), the compounds represented by the formulas $R^9{}_3Al$, $R^9{}_nAl(OR^{10})_{3-n}$ and $R^9{}_nAl(OAlR^{12}{}_2)_{3-n}$ are preferred, and the compounds having these formulas wherein R is an isoalkyl group and n is 2 are particularly preferred.

In the present invention, water may be used as a catalyst component in addition to the component (A), the component (B-1), the component(B-2) and the component (C). As the water employable in the invention, there can be mentioned water dissolved in a polymerization solvent described later, and adsorbed water or water of crystallization contained in a compound or a salt used for preparing the component (B-1).

The first olefin polymerization catalyst of the invention can be prepared by mixing the component (A) and the component (B-1) (or the component (B-2)), and if desired water (as a catalyst component), in an inert hydrocarbon medium (solvent) or an olefin medium (solvent).

There is no specific limitation on the order of mixing those components, but it is preferred that the component (B-1) (or the component (B-2)) is mixed with water, followed by mixing with the component (A).

The second olefin polymerization catalyst of the invention can be prepared by mixing the component (A), the component (B-1) (or the component (B-2)) and the component (C), and if desired water (as a catalyst component), in an inert hydrocarbon medium (solvent) or an olefin medium (solvent).

There is no specific limitation on the order of mixing those components. However, when the component (B-1) is used, it is preferred that the component (B-1) is mixed with the component (C), followed by mixing with the component (A). When the component (B-2) is used, it is preferred that the component (C) is mixed with the component (A), followed by mixing with the component (B-2).

In the mixing of each components, an atomic ratio (Al/transition metal) of aluminum in the component (B-1) to the transition metal in the component (A) is in the range of usually 10 to 10,000, preferably 20 to 5,000; and a concentration of the component (A) is in the range of about $10^{-8}$ to $10^{-1}$ mol/liter-medium, preferably $10^{-7}$ to $5\times10^{-2}$ mol/liter-medium.

When the component (B-2) is used, a molar ratio (component (A)/component (B-2)) of the component (A) to the component (B-2) is in the range of usually 0.01 to 10, preferably 0.1 to 5; and a concentration of the component (A) is in the range of about $10^{-8}$ to $10^{-1}$ mol/liter-medium, preferably $10^{-7}$ to $5\times10^{-2}$ mol/liter-medium.

In the preparation of the second olefin polymerization catalyst of the invention, an atomic ratio ($Al_c/Al_{B-1}$) of the aluminum atom ($Al_c$) in the component (C) to the aluminum atom ($Al_{B-1}$) in the component (B-1) is in the range of usually 0.02 to 20, preferably 0.2 to 10.

When water is used as a catalyst component, a molar ratio ($Al_{B-1}/H_2O$) of the aluminum atom ($Al_{B-1}$) in the component (B-1) to water ($H_2O$) is in the range of 0.5 to 50, preferably 1 to 40.

The above-mentioned each components may be mixed in a polymerizer, or a mixture of those components beforehand prepared may be fed to a polymerizer.

If the components are beforehand mixed, the mixing temperature is in the range of usually $-50°$ to $150°$ C., preferably $-20°$ to $120°$ C.; and the contact time is in the range of 1 to 1,000 minutes, preferably 5 to 600 minutes. The mixing temperature may be varied while the components are mixed and contacted with each other.

Examples of the media (solvents) used for preparing the olefin polymerization catalyst according to the invention include;

aliphatic hydrocarbons, such as propane, butane, pentane, hexane, heptane, octane, decane, dodecane and kerosine;

alicyclic hydrocarbons, such as cyclopentane, cyclohexane and methylcyclopentane;

aromatic hydrocarbons, such as benzene, toluene and xylene;

halogenated hydrocarbons, such as ethylene chloride, chlorobenzene and dichcloromethane; and mixtures of these hydrocarbons.

Next, the third and the fourth olefin polymerization catalysts according to the invention are described.

The third olefin polymerization catalyst according to the invention comprises:

a fine particle carrier;
(A) a transition metal compound represented by the above formula (I); and
(B) at least one compound selected from the group consisting of
(B-1) an organoaluminum oxy-compound, and
(B-2) a compound which reacts with the transition metal compound to form an ion pair;

said transition metal compound (A) and said at least one compound (B) being supported on the fine particle carrier.

The fourth olefin polymerization catalyst according to the invention comprises:

a solid catalyst component comprising:
a fine particle carrier,
(A) a transition metal compound represented by the above formula (I), and
(B) at least one compound selected from the group consisting of
(B-1) an organoaluminum oxy-compound, and
(B-2) a compound which reacts with the transition metal compound to form an ion pair, said transition metal compound (A) and said at least one compound (B) being supported on the fine particle carrier; and (C) an organoaluminum compound.

The transition metal compound (A) used for the third and the fourth olefin polymerization catalysts of the invention is the same as that for the aforesaid first and second olefin polymerization catalysts, and is represented by the above formula (I).

Examples of the organoaluminum oxy-compounds (B-1) used for the third and the fourth olefin polymerization catalysts of the invention are the same as those used for the first and the second olefin polymerization catalysts.

Examples of the compounds (B-2) which react with the transition metal compound (A) to form an ion pair and used for the third and the fourth olefin polymerization catalysts of the invention are the same as those used for the first and the second olefin polymerization catalysts.

Examples of the organoaluminum compounds (C) used for the fourth olefin polymerization catalyst of the invention are the same as those used for the second olefin polymerization catalyst.

The fine particle carrier used for the third and the fourth olefin polymerization catalysts of the invention is an inorganic or organic compound, and is a particulate or granular solid having a particle diameter of 10 to 300 μm, preferably 20 to 200 μm.

The inorganic carrier is preferably porous oxide, and examples thereof include $SiO_2$, $Al_2O_3$, MgO, $ZrO_2$, $TiO_2$, $B_2O_3$, CaO, ZnO, BaO, $ThO_2$, and mixtures thereof such as $SiO_2$—MgO, $SiO_2$—$Al_2O_3$, $SiO_2$—$TiO_2$, $SiO_2$—$V_2O_5$, $SiO_2$—$Cr_2$ and $SiO_2$—$TiO_2$MgO. Of these, preferred is a carrier containing $SiO_2$ and/or $Al_2O_3$ as its major component.

The above-mentioned inorganic oxides may contain carbonates, sulfates, nitrates and oxides, such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_2$, $Na_2O$, $K_2O$ and $Li_2O$, in a small amount.

The fine particle carrier is varied in its properties depending on the kind and the process for the preparation thereof, but preferably used in the invention is a carrier having a specific surface area of 50 to 1,000 m²/g, preferably 100 to 700 m²/g, and a pore volume of 0.3 to 2.5 cm³/g. The fine particle carrier is used after calcined at 100° to 1,000° C., preferably 150° to 700° C., if necessary.

Also employable as the fine particle carrier in the invention is a granular or particulate solid of an organic compound having a particle diameter of 10 to 300 μm. Examples of the organic compounds include (co)polymers prepared mainly from α-olefins of 2 to 14 carbon atoms such as ethylene, propylene, 1-butene and 4-methyl-1-pentene, and (co) polymers prepared mainly from vinylcyclohexane or styrene.

The fine particle carrier may contain a surface hydroxyl group or water. In this case, the surface hydroxyl group is contained in an amount of not less than 1.0% by weight, preferably 1.5 to 4.0% by weight, more preferably 2.0 to 3.5% by weight; and water is contained in an amount of not less than 1.0% by weight, preferably 1.2 to 20% by weight, more preferably 1.4 to 15% by weight. The water contained in the fine particle carrier means water which is adsorbed on the surface of the fine particle carrier.

The amount (% by weight) of the adsorbed water and the amount (% by weight) of the surface hydroxyl group in the fine particle carrier can be determined in the following manner.

Amount of adsorbed water

The weight reduction of the fine particle carrier after drying at 200° C. under ordinary pressure for 4 hours in a stream of nitrogen is measured, and a percentage of the weight after the drying to the weight before the drying is calculated.

Amount of surface hydroxyl group

The weight of the fine particle carrier after drying at 200° C. under ordinary pressure for 4 hours in a stream of nitrogen is taken as X (g). The carrier is calcined at 1,000° C. for 20 hours to obtain a calcined product containing no surface hydroxyl group. The weight of the calcined product thus obtained is taken as Y (g). The amount (% by weight) of the surface hydroxyl group is calculated from the following formula.

Amount (wt. %) of surface hydroxyl group={(X−Y)/X}×100

Further, in the third and the fourth olefin polymerization catalysts of the invention, such water as described in the first and the second olefin polymerization catalysts may be used as a catalyst component.

The third olefin polymerization catalyst of the invention (i.e., solid catalyst component) can be prepared by mixing the fine particle carrier, the component (A) and the component (B-1) (or the component (B-2)), and if desired water (catalyst component), in an inert hydrocarbon medium (solvent) or an olefin medium (solvent). In the mixing of those components, the component (C) can be further added.

There is no specific limitation on the order of mixing those components.

However, preferred processes are:

a process in which the fine particle carrier is mixed and contacted with the component (B-1) (or the component (B-2), and then with the component (A), followed by mixing with water if desired;

a process in which a mixture of the component (B-1) (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

In the mixing of each components, the component (A) is used in an amount of usually $10^{-6}$ to $5 \times 10^{-3}$ mol, preferably $3 \times 10^{-6}$ to $10^{-3}$ mol, per 1 g of the fine particle carrier; and a concentration of the component (A) is in the range of about $5 \times 10^{-6}$ to $2 \times 10^{-2}$ mol/liter-medium, preferably $2 \times 10^{-5}$ to $10^{-2}$ mol/liter-medium. An atomic ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio $(Al_{B-1}/H_2O)$ of the aluminum atom $((Al_{B-1})$ in the component (B-1) to water $(H_2O)$ is in the range of 0.5 to 50, preferably 1 to 40.

The temperature for mixing the components is in the range of usually −50° to 150° C., preferably −20° to 120° C.; and the contact time is in the range of 1 to 1,000 minutes, preferably 5 to 600 minutes. The mixing temperature may be varied while the components are mixed and contacted with each other.

The fourth olefin polymerization catalyst according to the invention is formed from the above-mentioned third olefin polymerization catalyst (solid catalyst component) and the organoaluminum compound (C). The component (C) is used in an amount of not more than 500 mol, preferably 5 to 200 mol, per 1 g of the transition metal atom in the component (A) contained in the solid catalyst component.

The third and the fourth olefin polymerization catalysts of the invention may contain other components useful for the olefin polymerization than the above-described components.

Examples of the inert hydrocarbon media (solvents) used for preparing the third and the fourth olefin polymerization catalysts of the invention are the same as those used for the first and the second olefin polymerization catalysts.

Next, the fifth and the sixth olefin polymerization catalysts according to the invention are described.

The fifth olefin polymerization catalyst according to the invention comprises:

a fine particle carrier;

(A) a transition metal compound represented by the above formula (I);
(B) at least one compound selected from the group consisting of
   (B-1) an organoaluminum oxy-compound, and
   (B-2) a compound which reacts with the transition metal compound to form an ion pair; and
a prepolymerized olefin polymer produced by prepolymerization.

The sixth olefin polymerization catalyst according to the invention comprises:
a fine particle carrier;
(A) a transition metal compound represented by the above formula (I);
(B) at least one compound selected from the group consisting of
   (B-1) an organoaluminum oxy-compound, and
   (B-2) a compound which reacts with the transition metal compound to form an ion pair;
(C) an organoaluminum compound; and
a prepolymerized olefin polymer produced by prepolymerization.

Examples of the fine particle carrier used for the fifth and the sixth olefin polymerization catalysts of the invention are the same as those for the aforesaid third and fourth olefin polymerization catalysts.

The transition metal compound (A) used for the fifth and the sixth olefin polymerization catalysts of the invention is the same as that for the aforesaid first and second olefin polymerization catalysts, and is represented by the above formula (I).

Examples of the organoaluminum oxy-compounds (B-1) used for the fifth and the sixth olefin polymerization catalysts of the invention are the same as those used for the first and the second olefin polymerization catalysts.

Examples of the compounds (B-2) which react with the transition metal compound (A) to form an ion pair and used for the fifth and the sixth olefin polymerization catalysts of the invention are the same as those used for the first and the second olefin polymerization catalysts.

Examples of the organoaluminum compounds (C) used for the sixth olefin polymerization catalyst of the invention are the same as those used for the second olefin polymerization catalyst.

Further, in the fifth and the sixth olefin polymerization catalysts of the invention, such water as described in the first and the second olefin polymerization catalysts may be used as a catalyst component.

The fifth olefin polymerization catalyst of the invention can be prepared by prepolymerizing a small amount of an olefin to the solid catalyst component. The solid catalyst component is obtained by mixing the fine particle carrier, the component (A) and the component (B-1) (or the component (B-2)), and if desired water, in an inert hydrocarbon medium (solvent) or an olefin medium (solvent). In the mixing of those components, the component (C) can be further added.

There is no specific limitation on the order of mixing those components.

However, preferred processes are:
a process in which the fine particle carrier is mixed and contacted with the component (B-1) (or the component (B-2)), and then with the component (A), followed by mixing with water if desired a process in which a mixture of the component (B-1) (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

The mixing of the components is desirably carried out with stirring.

In the mixing of each components, the component (A) is used in an amount of usually $10^{-6}$ to $5 \times 10^{-3}$ mol, preferably $3 \times 10^{-6}$ to $10^{-3}$ mol, per 1 g of the fine particle carrier; and a concentration of the component (A) is in the range of about $5 \times 10^{-6}$ to $2 \times 10^{-2}$ mol/liter-medium, preferably $10^{-5}$ to $10^{-2}$ mol/liter-medium. An atomic weight ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio $(Al_{B-1}/H_2O)$ of the aluminum atom $(Al_{B-1})$ in the component (B-1) to water ($H_2O$) is in the range of 0.5 to 50, preferably 1 to 40.

The temperature for mixing the components is in the range of usually $-50°$ to $150°$ C, preferably $-20°$ to $120°$ C.; and the contact time is in the range of 1 to 1,000 minutes, preferably 5 to 600 minutes. The mixing temperature may be varied while the components are mixed and contacted with each other.

The fifth olefin polymerization catalyst of the invention can be prepared by prepolymerizing an olefin in the presence of the above-mentioned components. The prepolymerization can be carried out by introducing an olefin into an inert hydrocarbon medium (solvent) in the presence of the components and if necessary the component (C).

In the prepolymerization, the component (A) is used in an amount of usually 10–5 to $2 \times 10^{-2}$ mol/liter, preferably $5 \times 10^{-5}$ to $10^{-2}$ mol/liter. The prepolymerization temperature is in the range of $-20°$ to $80°$ C., preferably $0°$ to $50°$ C.; and the prepolymerization time is 0.5 to 100 hours, preferably about 1 to 50 hours.

The olefin used for the prepolymerization is selected from olefins which are used for polymerization, and it is preferable to use the same monomer as used in the polymerization or a mixture of the same monomer as used in the polymerization and an α-olefin.

In the olefin polymerization catalyst of the invention obtained as above, it is desired that the transition metal atom is supported in an amount of about $10^{-6}$ to $10^{-3}$ g.atom, preferably $2 \times 10^{-6}$ to $3 \times 10^{-4}$ g.atom, per 1 g of the fine particle carrier; and the aluminum atom is supported in an amount of about $10^{-3}$ to $10^{-1}$ g.atom, preferably $2 \times 10^{-3}$ to $5 \times 10^{-2}$ g.atom, per 1 g of the fine particle carrier. Further, it is also desired that the component (B-2) is supported in an amount of $5 \times 10^{-7}$ to 0.1 g.atom, preferably $2 \times 10^{-7}$ to $3 \times 10^{-2}$ g.atom, in terms of the boron atom contained in the component (B-2).

The amount of the prepolymerized polymer prepared by the prepolymerization is desired to be in the range of about 0.1 to 500 g, preferably 0.3 to 300 g, particularly preferably 1 to 100 g, per 1 g of the fine particle carrier.

The sixth olefin polymerization catalyst of the invention is formed from the above-mentioned fifth olefin polymerization catalyst (component) and the organoaluminum compound (C). The organoaluminum compound (C) is used in an amount of not more than 500 mol, preferably 5 to 200 mol, per 1 g.atom of the transition metal atom in the component (A).

The fifth and the sixth olefin polymerization catalysts of the invention may contain other components useful for the olefin polymerization than the above-described components.

Examples of the inert hydrocarbon solvents used for the fifth and the sixth olefin polymerization catalysts of the invention are the same as those used for preparing the aforesaid first and second olefin polymerization catalysts.

Polyolefins obtained by the use of the olefin polymerization catalysts as described above have a narrow molecular weight distribution, a narrow composition distribution and a high molecular weight and the olefin polymerization catalysts have a high polymerization activity.

Further, when olefins of 3 or more carbon atoms are polymerized in the presence of the olefin polymerization catalysts, polyolefins having excellent stereoregularity can be obtained.

Next, the process for olefin polymerization according to the present invention is described.

An olefin is polymerized in the presence of any of the above-described olefin polymerization catalysts. The polymerization may be carried out by a liquid phase polymerization process such as a suspension polymerization or by a gas phase polymerization.

In the liquid phase polymerization process, the same inert hydrocarbon solvent as used in the preparation of the catalyst can be used, or the olefin itself can be also used as a solvent.

In the polymerization of an olefin using the first or the second polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system.

In the polymerization of an olefin using the third or the fourth polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system. In this case, an aluminoxane which is not supported on the carrier may be employed, if desired.

In the polymerization of an olefin using the fifth or the sixth polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system. In this case, an aluminoxane which is not supported on the carrier may be employed, if desired.

In the slurry polymerization, the temperature for the olefin polymerization is in the range of usually −100° to 100° C., preferably −50° to 90° C. In the liquid phase polymerization, the temperature is in the range of usually −100° to 250° C., preferably −50° to 200° C. In the gas phase polymerization process, the temperature is in the range of usually −47° to 120° C., preferably −40° to 100° C. The polymerization pressure is in the range of usually atmospheric pressure to 100 kg/cm$^2$, preferably atmospheric pressure to 50 kg/cm$^2$. The polymerization reaction can be carried out either batchwise, semicontinuously or continuously. Further, the polymerization may be performed in two or more stages having different reaction conditions.

The molecular weight of the resulting olefin polymer can be regulated by allowing hydrogen to exist in the polymerization system or by varying the polymerization temperature.

Examples of the olefins to be polymerized using the olefin polymerization catalysts of the invention include:

α-olefins of 2 to 20 carbon atoms, such as ethylene, propylene, 1-butene, 1-pentene, 1-hexene, 4-methyl-1-pentene, 1-octene, 1-decene, 1-dodecene, 1-tetradecene, -1-hexadecene, 1-octadecene and 1-eicosene; and cycloolefins of 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Also employable are styrene, vinylcyclohexane, diene, etc.

The olefin polymerization catalyst according to the present invention is suitably used for homopolymerization of propylene or copolymerization of propylene with at least one kind of α-olefin selected from the group consisting of ethylene and α-olefins of 4 to 20 carbon atoms.

Polyolefin obtained by using the olefin polymerization catalyst of the present invention (e.g., said polyolefin is a propylene/ethylene copolymer containing not less than 50% by mol of propylene unit) usually has a value of Mw/Mn of 1.5 to 3.5, triad tacticity (mm fraction) of not less than 98.0%, a proportion of inversely inserted units based on 2,1-insertion of propylene monomer of not more than 0.20%, and a proportion of inversely inserted units based on 1,3-insertion of propylene monomer of not more than 0.03%.

When the resulting polyolefin is a propylene homopolymer, said polymer usually has a value of Mw/Mn of 1.5 to 3.5, triad tacticity (mm fraction) of not less than 99.0%, a proportion of inversely inserted units based on 2,1-insertion of propylene monomer of not more than 0.50%, and a proportion of inversely inserted units based on 1,3-insertion of propylene monomer of not more than 0.03%.

The propylene homopolymer, the propylene copolymer and the propylene elastomer according to the invention are described hereinafter.

Propylene homopolymer

The first propylene homopolymer according to the present invention is a homopolymer of propylene obtained by homopolymerization of propylene in the presence of the aforementioned catalyst for olefin polymerization.

The propylene homopolymer of the invention desirably has an intrinsic viscosity [η], as measured in decahydronaphthalene at 135° C., of 0.1 to 20 dl/g, preferably 0.5 to 10 dl/g, more preferably 1 to 5 dl/g, and a value of Mw/Mn of 1.5 to 3.5, preferably 2.0 to 3.0, more preferably 2.0 to 2.5.

The second propylene homopolymer according to the invention has a triad tacticity of not less than 99.0%, preferably not less than 99.2%, more preferably not less than 99.5%. The term "triad tacticity" means a proportion of such of three propylene units chains (i.e., chains consisting of three propylene units continuously bonded) that the directions of methyl branches in the propylene chain are the same as each other and each propylene unit is bonded to each other with head-to-tail bonds, to total three propylene units chain in the polymer, and this term is sometimes referred to as "mm fraction" hereinafter. It is also desirably that the proportion of inversely inserted units based on 2,1-insertion of propylene monomer is in the range of not more than 0.50%, preferably not more than 0.18%, more preferably not more than 0.15%, and the intrinsic viscosity [η], as measured in decahydronaphthalene at 135° C., is in the range of 0.1 to 20 dl/g, preferably 0.5 to 10 dl/g, more preferably 1 to 5 dl/g.

The propylene homopolymer having a triad tacticity (mm fraction) of not less than 99.0%, a proportion of inversely inserted units based on 2,1-insertion of propylene monomer of not more than 0.5%, and an intrinsic viscosity [η], as measured in decahydronaphthalene at 135° C., of 0.1 to 20 dl/g is novel.

Moreover, in the second propylene homopolymer according to the present invention, a proportion of inversely inserted units based on 1,3-insertion of propylene monomer is desirably less than the minimum limit of detection by a measurement of $^{13}$C-NMR, and a value of Mw/Mn is desirably in the range of 1.5 to 3.5, preferably 2.0 to 3.0, more preferably 2.0 to 2.5.

The second propylene homopolymer of the invention can be prepared by homopolymerizing propylene in the presence of, for example, the aforesaid olefin polymerization catalysts. The polymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, or propylene can be also used as a solvent.

In the suspension polymerization, the temperature for polymerizing propylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The polymerization pressure is in the range of usually atmospheric pressure to 100 kg/cm$^2$, preferably atmospheric pressure to 50 kg/cm$^2$. The polymerization reaction can be carried out either batchwise, semicontinuously or contiguously. Further, the polymerization can be carried out in two or more stages having different reaction conditions.

The molecular weight of the resultant propylene polymer can be regulated by allowing hydrogen to exist in the polymerization system or by varying the polymerization temperature and the polymerization pressure.

Propylene copolymer

The first propylene copolymer according to the present invention is a propylene/α-olefin copolymer obtained by copolymerization of propylene and at least one kind of α-olefin selected from the group consisting of ethylene and a-olefins of 4 to 20 carbon atoms in the presence of the aforementioned catalyst for olefin polymerization.

The propylene copolymer contains propylene units in an amount of not less than 50% by mol, preferably not less than 60% by mol, more preferably not less than 70% by mol, and comonomer units derived from the α-olefin selected from the group consisting of ethylene and α-olefins of 4 to 20 carbon atoms in an amount of not more than 50% by mol, preferably 5 to 40% by mol, more preferably 10 to 30% by mol.

Examples of α-olefin of 4 to 20 carbon atoms include 1-butene, 1-pentene, 1-hexene, 4-methyl-1-pentene, -1-heptene, 1-octene, 2-ethyl-1-hexene, 1-decene, 1-dodecene, 1-tetradecene and 1-eicosene.

Of these, preferred comonomers used for copolymerization include ethylene, 1-butene, 1-pentene, -1-hexene, 1-octene and 1-decene.

In the present invention, composition of the propylene copolymer is determined by using $^{13}$C-NMR.

The propylene copolymer has an intrinsic viscosity [η], as measured in decahydronaphthalene at 135° C., of 0.1 to 20 dl/g, preferably 0.5 to 10 dl/g, more preferably 1 to 5 dl/g, and a value of Mw/Mn of 1.5 to 3.5, preferably 2.0 to 3.0, more preferably 2.0 to 2.5.

The second propylene copolymer according to the present invention contains propylene units in an amount of not less than 50% by mol, preferably not less than 60% by mol, more preferably not less than 70% by mol, and ethylene units in an amount of not more than 50% by mol, preferably 5 to 40% by mol, more preferably 10 to 30% by mol. The propylene copolymer may contain constituent units derived from other olefins than propylene and ethylene, for example, monomer units derived from other monomers such as the aforementioned α-olefins of 4 to 20 carbon atoms and dienes in a small amount.

The second propylene copolymer according to the invention has a triad tacticity (mm fraction) of not less than 98.0%, preferably not less than 98.2%, more preferably not less than 98.5%. It is also desirably that the proportion of inversely inserted units based on 2,1-insertion of propylene monomer is in the range of not more than 0.50%, preferably not more than 0.18%, more preferably not more than 0.15%, and an intrinsic viscosity [η], as measured in decahydronaphthalene at 135° C., is in the range of 0.1 to 20 dl/g, preferably 0.5 to 10 dl/g, more preferably 1 to 5 dl/g.

The propylene/ethylene random copolymer having a triad tacticity (mm fraction) of not less than 98.0%, a proportion of inversely inserted units based on 2,1-insertion of propylene monomer of not more than 0.5%, and an intrinsic viscosity [η], as measured in decahydronaphthalene at 135° C., of 0.1 to 20 dl/g is novel.

Moreover, in the second propylene copolymer according to the present invention, a proportion of inversely inserted units based on 1,3-insertion of propylene monomer is desirably less than the minimum limit of detection by a measurement of $^{13}$C-NMR, and a value of Mw/Mn is desirably in the range of 1.5 to 3.5, preferably 2.0 to 3.0, more preferably 2.0 to 2.5.

The second propylene copolymer of the invention can be prepared by copolymerizing propylene and ethylene in the presence of, for example, the aforesaid olefin polymerization catalysts. The copolymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, or propylene and/or ethylene can be also used as a solvent.

In the suspension polymerization, the temperature for copolymerizing propylene and ethylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The copolymerization pressure is in the range of usually atmospheric pressure to 100 kg/cm$^2$, preferably atmospheric pressure to 50 kg/cm$^2$. The copolymerization reaction can be carried out either batchwise, semicontinuously or continuously. Further, the copolymerization can be carried out in two or more stages having different reaction conditions.

The third propylene copolymer according to the present invention contains propylene units in an amount of 95 to 99.5% by mol, preferably 95 to 99% by mol, more preferably 95 to 98% by mol, and ethylene units in an amount of 0.5 to 5% by mol, preferably 1 to 5% by mol, more preferably 2 to 5% by mol.

The propylene copolymer may contain constituent units derived from other olefins than propylene and ethylene in an amount of not more than 5% by mol.

The third propylene copolymer according to the invention has a triad tacticity of not less than 95.0%, preferably not less than 96.0%, more preferably not less than 97.0%. It is also desirably that the proportion of inversely inserted units based on 2,1-insertion of propylene monomer is in the range of 0.05 to 0.5%, preferably 0.05 to 0.4%, more preferably 0.05 to 0.3%, and the intrinsic viscosity [η], as measured in decahydronaphthalene at 135° C., is in the range of 0.1 to 12 dl/g, preferably 0.5 to 12 dl/g, more preferably 1 to 12 dl/g.

In the propylene copolymer of the invention, thea proportion of inversely inserted units based on 1,3-insertion of propylene monomer is desirably not more than 0.05%.

The third propylene copolymer according to the present invention can be prepared by copolymerizing ethylene and propylene in the presence of an olefin polymerization catalyst, for example, a catalyst comprising:

(A) a transition metal compound represented by the following formula (Ia);

(B) at least one compound selected from the group consisting of (B-1) an organoaluminum oxy-compound, and
 (B-2) a compound which reacts with the transition metal compound to form an ion pair; and optionally, (C) an organoaluminum compound.

The transition metal compound used in the preparation of the third propylene copolymer according to the present invention is a transition metal compound represented by the following formula (Ia).

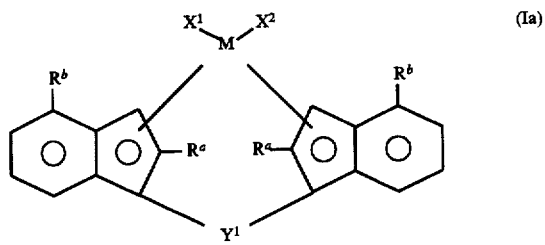

In the formula (Ia), M is a transition metal atom mentioned in the aforementioned formula (I).

$R^a$ is a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group. Examples of the halogen atoms, the hydrocarbon groups of 1 to 20 carbon atoms, the halogenated hydrocarbon groups of 1 to 20 carbon atoms include the atoms and groups exemplified for $X^1$ and $X^2$ in the aforementioned formula (I).

Examples of the silicon-containing groups include monohydrocarbon-substituted silyl such as methylsilyl and phenylsilyl; dihydrocarbon-substituted silyl such as dimethylsilyl and diphenylsilyl; trihydrocarbon-substituted silyl such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ether of hydrocarbon-substituted silyl such as trimethylsilyl ether; silicon-substituted alkyl group such as trimethylsilylmethyl; and silicon-substituted aryl group such as trimethylphenyl.

Examples of the oxygen-containing groups include a hydroxy group; an alkoxy group such as methoxy, ethoxy, propoxy and butoxy; an allyloxy group such as phenoxy, methylphenoxy, dimethylphenoxy and naphthoxy; and an arylalkoxy group such as phenylmethoxy and phenylethoxy.

Examples of the sulfur-containing groups include groups obtained by substituting sulfur for oxygen in the above-mentioned oxygen-containing groups.

Examples of the nitrogen-containing groups include an amino group; an alkylamino group such as methylamino, dimethylamino, diethylamino, dipropylamino, dibutylamino and dicyclohexylamino; an arylamino group such as phenylamino, diphenylamino, ditolylamino, dinaphthylamino and methylphenylamino; and an alkylarylamino group.

Examples of the phosphorus-containing groups include a phosphino group such as dimethylphosphino and diphenylphosphino.

Of these, $R^a$ is preferably a hydrocarbon group, particularly a hydrocarbon group of 1 to 4 carbon atoms such as methyl, ethyl, propyl and butyl.

$R^b$ is aryl group of 6 to 16 carbon atoms, and examples thereof are the same as the groups described as $R^2$.

The aryl groups may be substituted with a halogen atom, a hydrocarbon group of 1 to 20 carbon atoms or a halogenated hydrocarbon group of 1 to 20 carbon atoms, as same as the aforementioned $R^a$.

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group. Examples of those atoms and groups include the halogen atoms, the hydrocarbon groups of 1 to 20 carbon atoms, the halogenated hydrocarbon groups of 1 to 20 carbon atoms and the oxygen-containing groups exemplified above with respect to $X^1$ and $X^2$ as described in the aforementioned formula (I).

$Y^1$ is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— (R$^3$ is a hydrogen atom, a halogen atom, a hydrocarbon group of 1 to 20 carbon atoms or a halogenated hydrocarbon group of 1 to 20 carbon atoms). Examples thereof include the same groups mentioned as Y in the aforementioned formula (I) and divalent tin-containing groups include groups obtained by substituting tin for silicon in the above-mentioned divalent silicon-containing groups.

Of these, preferred are a divalent silicon-containing group, a divalent germanium-containing group and a divalent tin-containing group. More preferred is a divalent silicon-containing group. Of the silicon-containing groups, alkylsilylene, alkylarylsilylene and arylsilylene are particularly preferred.

Listed below are examples of the transition metal compounds represented by the above formula (Ia).

rac-Dimethylsilyl-bis{1-(4-phenylindenyl)}zirconium dichloride, rac-Dimethylsilyl-bis{1-(2-methyl-4-phenylindenyl)}zirconium dichloride, rac-Dimethylsilyl-bis{1-(2-methyl-4-(α-naphthyl)indenyl)}zirconium dichloride, rac-Dimethylsilyl-bis{1-(2-methyl-4-(β-naphthyl)indenyl)}zirconium dichloride, rac-Dimethylsilyl-bis{1-(2-methyl-4-(1-anthracenyl)indenyl)}zirconium dichloride, rac-Dimethylsilyl-bis{1-(2-methyl-4-(2-anthracenyl)indenyl)}zirconium dichloride, rac-Dimethylsilyl-bis{1-(2-methyl-4-(9-anthracenyl)indenyl)}zirconium dichloride, rac-Dimethylsilyl-bis{1-(2-methyl-4-(9-phenanthryl)indenyl)}zirconium dichloride, rac-Dimethylsilyl-bis{1-(2-methyl-4-(p-fluorophenyl)indenyl)}zirconium dichloride, rac-Dimethylsilyl-bis{1-(2-methyl-4(pentafluorophenyl)indenyl)}zirconium dichloride, rac-Dimethylsilyl-bis{1-(2-methyl-4-(p-chlorophenyl)indenyl)}zirconium dichloride, rac-Dimethylsilyl-bis{1-(2-methyl-4-(m-chlorophenyl)indenyl)}zirconium dichloride, rac-Dimethylsilyl-bis{1-(2-methyl-4-(o-chlorophenyl)indenyl)}zirconium dichloride, rac-Dimethylsilyl-bis{1-(2-methyl-4-(o,p-dichlorophenyl)phenyl-1-indenyl)}zirconium dichloride, rac-Dimethylsilyl-bis{1-(2-methyl-4-(p-bromophenyl)indenyl)}zirconium dichloride, rac-Dimethylsilyl-bis{1-(2-methyl-4-(p-tolyl)indenyl)}zirconium dichloride, rac-Dimethylsilyl-bis{1-(2-methyl-4-(m-tolyl)indenyl)}zirconium dichloride, rac-Dimethylsilyl-bis{1-(2-methyl-4-(o-tolyl)indenyl)}zirconium dichloride, rac-Dimethylsilyl-bis{1-(2-methyl-4-(o,o-dimethylphenyl)indenyl)}zirconium dichloride, rac-Dimethylsilyl-bis{1-(2-methyl-4-(p-ethylphenyl)indenyl)}zirconium dichloride, rac-Dimethylsilyl-bis{1-(2-methyl-4-(p-i-propylphenyl)indenyl)}zirconium dichloride, rac-Dimethylsilyl-bis{1-(2-methyl-4-(p-benzylphenyl)indenyl)}zirconium dichloride, rac-Dimethylsilyl-bis{1-(2-methyl-4-(p-biphenyl)indenyl)}zirconium dichloride, rac-Dimethylsilyl-bis{1-(2-methyl-4-(m-biphenyl)indenyl)}zirconium dichloride, rac-Dimethylsilyl-bis{1-(2-methyl-4-(p-trimethylsilylphenyl)indenyl)}zirconium dichloride, rac-Dimethylsilyl-bis{1-(2-methyl-4-(m-trimethylsilylphenyl)indenyl)}zirconium dichloride, rac-Dimethylsilyl-bis{1-(2-ethyl-4-phenylindenyl)}zirconium dichloride, rac-Diphenylsilyl-bis{1-(2-ethyl-4-phenylindenyl)}zirconium dichloride, rac-Dimethylsilyl-bis{1-(2-phenyl-4-phenylindenyl)}zirconium dichloride, rac-Dimethylsilyl-bis{1-(2-n-propyl-4-phenylindenyl)}zirconium dichloride, rac-Diethylsilyl-bis{1-(2-methyl-4-phenylindenyl)}zirconium dichloride, rac-Di-(i-propyl)silyl-bis{1-(2-methyl-4-phenylindenyl)}zirconium dichloride, rac-Di-(n-butyl)silyl-bis{1-(2-methyl-4-phenylindenyl)}zirconium dichloride, rac-Dicyclohexylsilyl-bis{1-(2-methyl-4-phenylindenyl)}zirconium dichloride, rac-methylphenylsilyl-bis{1-(2-methyl-4-phenylindenyl)}zirconium dichloride rac-diphenylsilyl-bis{1-(2-methyl-4-phenylindenyl)}zirconium dichloride, rac-di(p-tolyl)silyl-bis{1-(2-methyl-4-phenylindenyl)}zirconium dichloride, rac-di(p-chlorophenyl)silyl-bis{1-(2-methyl-4-phenylindenyl)}zirconium dichloride, rac-methylene-bis{1-(2-methyl-4-phenylindenyl)}zirconium dichloride, rac-ethylene-bis{1-(2-methyl-4-phenylindenyl)}zirconium dichloride, rac-dimethylgermyl-bis{1-(2-methyl-4-phenylindenyl)}zirconium dichloride, rac-dimethylstanyl-bis{1-(2-methyl-4-phenylindenyl)}zirconium dichloride, rac-dimethylsilyl-bis{1-(2-methyl-4-phenylindenyl)}zirconium dibromide, rac-dimethylsilyl-bis{1-(2-methyl-4-phenylindenyl)}zirconium dimethyl, rac-dimethylsilyl-bis{1-(2-methyl-4-phenylindenyl)}zirconium methylchloride, rac-dimethylsilyl-bis{1-(2-methyl-4-phenylindenyl)}zirconium monochloride mono(trifluoromethanesulfonato), rac-dimethylsilyl-bis{1-(2-methyl-4-phenylindenyl)}zirconium di(trifluoromethanesulfonato), rac-dimethylsilyl-bis{1-(2-methyl-4-phenylindenyl)}zirconium di(p-toluenesulfonato), rac-dimethylsilyl-bis{1-(2-methyl-4-phenylindenyl)}zirconium di(methylsulfonato), rac-dimethylsilyl-bis{1-(2-methyl-4-phenylindenyl)}zirconium di(trifluoromethanesulfinato), rac-dimethylsilyl-bis{1-(2-methyl-4-phenylindenyl)}zirconium di(trifluoroacetato), rac-dimethylsilyl-bis{1-(2-methyl-4-phenylindenyl)}zirconium monochloride(n-butoxide), rac-dimethylsilyl-bis{1-(2-methyl-4-phenylindenyl)}zirconium di(n-butoxide), and rac-dimethylsilyl-bis{1-(2-methyl-4-phenylindenyl)}zirconium monochloride(phenoxide).

There may also be used the transition metal compounds obtained by substituting titanium metal, hafnium metal, vanadium metal, niobium metal, tantalum metal, chromium metal, molybdenum metal or tungsten metal for zirconium metal in the above-exemplified compounds.

The transition metal compound is used as an olefin polymerization catalyst component in the form of usually a racemic modification, but the R configuration or the S configuration can be also used.

An olefin polymerization catalyst used for the preparation of the propylene copolymer according to the present invention is a catalyst obtained by replacing the component (A) of the first to sixth olefin polymerization catalysts with the transition metal compound represented by the aforementioned formula (Ia).

The propylene copolymer of the invention can be prepared by copolymerizing propylene and ethylene in the presence of, for example, the aforesaid olefin polymerization catalysts. The copolymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, and propylene and/or ethylene can be also used as a solvent.

In the suspension polymerization, the temperature for copolymerizing propylene and ethylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The copolymerization pressure is in the range of usually atmospheric pressure to 100 kg/cm$^2$, preferably atmospheric pressure to 50 kg/cm$^2$. The copolymerization reaction can be carried out either batchwise, semicontinuously or continuously. Further, the copolymerization can be carried out in two or more stages having different reaction conditions.

The molecular weight of the resultant propylene copolymer can be regulated by allowing hydrogen to exist in the copolymerization system or by varying the copolymerization temperature and the copolymerization pressure.

Propylene elastomer

The propylene elastomer of the invention is a propylene/ethylene random copolymer containing propylene units in an amount of 50 to 95% by mol, preferably 60 to 93% by mol, more preferably 70 to 90% by mol, and containing ethylene units in an amount of 5 to 50% by mol, preferably 7 to 40% by mol, more preferably 10 to 30% by mol.

The propylene elastomer may contain constituent units derived from other olefins than propylene and ethylene in an amount of not more than 10% by mol.

In the propylene elastomer of the invention, it is desirably that the triad tacticity is not less than 90.0%, preferably not less than 93.0%, more preferably not less than 96.0%, a proportion of inversely inserted units based on 2,1-insertion of propylene monomer is 0.05 to 0.5%, preferably 0.05 to 0.4%, more preferably 0.05 to 0.3%, and an intrinsic viscosity [η], as measured in decahydronaphthalene at 135° C., is 0.1 to 12 dl/g, preferably 0.5 to 12 dl/g, more preferably 1 to 12 dl/g.

Moreover, in the propylene elastomer according to the present invention, a proportion of inversely inserted units based on 1,3-insertion of propylene monomer is desirably not more than 0.05%, preferably not more than 0.03.

The propylene elastomer of the invention can be prepared by copolymerizing propylene and ethylene in the presence of, for example, the aforesaid olefin polymerization catalyst used in the preparation of the third propylene copolymer. The copolymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, and propylene and/or ethylene can be also used as a solvent.

In the suspension polymerization, the temperature for copolymerizing propylene and ethylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The copolymerization pressure is in the range of usually atmospheric pressure to 100 kg/cm$^2$, preferably atmospheric pressure to 50 kg/cm$^2$. The copolymerization reaction can be carried out either batchwise, semicontinuously or continuously. Further, the copolymerization can be carried out in two or more stages having different reaction conditions.

The molecular weight of the resultant propylene copolymer can be regulated by allowing hydrogen to exist in the copolymerization system or by varying the copolymerization temperature and the copolymerization pressure.

In the present invention, the molecular weight distribution (Mw/Mn), the triad tacticity (mm fraction), the proportion of inversely inserted units based on 2,1-insertion of propylene monomer, and the proportion of inversely inserted units based on 1,3-insertion of propylene monomer are determined by the following manner.

Molecular Weight Distribution (Mw/Mn)

The Mw/Mn was determined from a chromatograph measured using Gel permeation chromatography (GPC) (150-ALC/GPC™, manufactured by Waters Co.). The measurement was conducted at temperature of 140° C. by using column of GMH-HT and GMH-HLT type (both manufactured by Toyo Soda K. K) and o-dichlorobenzene as an eluting solvent. From the chromatograph, a number average molecular weight (Mn) and a weight average molecular weight (Mw), both in terms of polypropylene by universal method (with the proviso that when the comonomer content is not less than 10% by mol, polystyrene standard was used) were calculated to obtain Mw/Mn.

Triad Tacticity (mm fraction)

Triad tacticity (mm fraction) of the propylene copolymer is determined by defining as a proportion of such chains of three propylene units that directions of methyl branches in the propylene chain are the same as each other and each propylene units bonded to each other with head-to-tail bonds, when the main chains are represented by plane-zigzag structure. The triad tacticity (mm fraction) of the propylene copolymer can be determined from a $^{13}$C-NMR spectrum of the propylene copolymer and the following formula:

$$\text{Triad tacticity (\%)} = \frac{PPP(mm)}{PPP(mm) + PPP(mr) + PPP(rr)} \times 100$$

wherein PPP(mm), PPP(mr) and PPP(rr) denote peak areas derived from the methyl groups of the second units in the following three propylene units chain consisting of head-to-tail bonds, respectively:

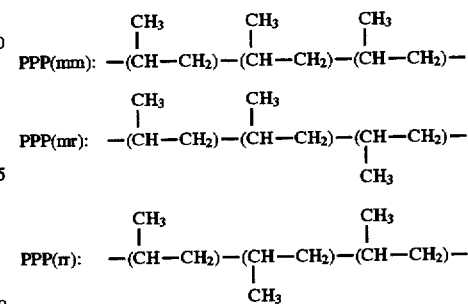

The $^{13}$C-NMR spectrum is measured in the following manner. A sample is completely dissolved in a mixed solvent containing about 0.5 ml of hexachlorobutadiene, o-dichlorobenzene or 1,2,4-trichlorobenzene and about 0.05 ml of deuterated benzene (i.e., lock solvent) in an NMR sample tube (diameter: 5 mm), and then subjected to a proton perfect decoupling method at 120° C. to measure the $^{13}$C-NMR spectrum. The measurement is conducted under the conditions of a flip angle of 45° and a pulse interval of not less than 3.4 T$_1$ (T$_1$ is a maximum value with respect to a spin-lattice relaxation time of the methyl group). In the polypropylene, T$_1$ of the methylene group and T$_1$ of the methine group are each shorter than that of the methyl group, and hence the magnetization recovery of all carbons under these conditions is not less than 99%. With respect to the chemical shift, the methyl group of the third unit in the five propylene units chain consisting of head-to-tail bonds is set to 21.593 ppm, and the chemical shift of other carbon peak is determined by using the above-mentioned value as a reference.

The spectrum is classified into the first region (21.1–21.9 ppm), the second region (20.3–21.0 ppm) and the third region (19.5–20.3 ppm).

In the first region, the methyl group of the second unit in the three propylene units chain represented by PPP(mm) resonates.

In the second region, the methyl group of the second unit in the three propylene units chain represented by PPP(mr) resonates and the methyl group (PPE-methyl group) of a propylene unit whose adjacent units are a propylene unit and an ethylene unit resonate.

In the third region, the methyl group of the second unit in the three propylene units chain represented by PPP (rr) resonates and the methyl group (EPE-methyl group) of a propylene unit whose adjacent units are ethylene units resonate.

Further, the propylene copolymer has the following structures (i), (ii) and (iii) containing an inversely inserted unit.

Structure (i)

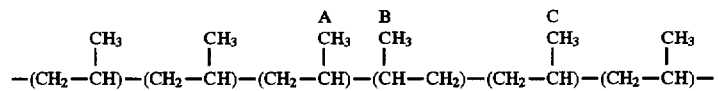

Structure (ii)

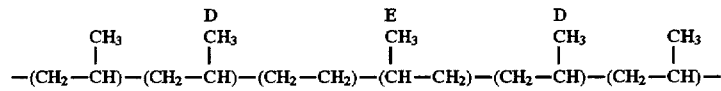

Structure (iii)

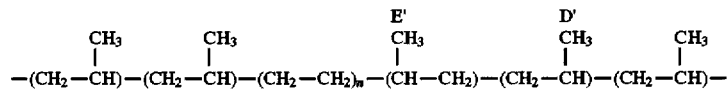

(n ≧ 2)

Among the peaks derived from the structures (i), (ii) and (iii), peaks of the carbon A and the carbon B do not appear in the first to third regions, because the carbon A resonates at 17.3 ppm and the carbon B resonates at 17.0 ppm. Further, the carbon A and the carbon B do not relate to the three propylene units chain, and hence it is not necessary to take these carbons into consideration of calculation of triad tacticity.

Peaks of the carbon C, carbon D and carbon D' appear in the second region; and peaks of the carbon E and carbon E' appear in the third region.

Of the peaks in the first to third regions as described above, peaks which are not based on the three propylene units chain consisting of head-to-tail bonds are peaks based on the EPE-methyl group (resonance in the vicinity of 20.7 ppm), the PPE-methyl group (resonance in the vicinity of 19.8 ppm), the carbon C, the carbon D, the carbon D', the carbon E and the carbon E'.

The peak area based on the PPE-methyl group can be evaluated by the peak area of the PPE-methine group (resonance in the vicinity of 30.6 ppm), and the peak area based on the EPE-methyl group can be evaluated by the peak area of the EPE-methine group (resonance in the vicinity of 32.9 ppm). The peak area based on the carbon C can be evaluated by the peak area of the adjacent methine group (resonance in the vicinity of 31.3 ppm), the peak area based on the carbon D can be evaluated by ½ as much as the sum of the peak areas of the αβ methylene carbons of the structure (ii) (resonance in the vicinity of 34.3 ppm and resonance in the vicinity of 34.5 ppm, respectively), and the peak area based on the carbon D' can be evaluated by the peak area of the adjacent methine group of the methyl group of the carbon E' of the aforementioned structure (iii) (resonance in the vicinity of 33.3 ppm), the peak area based on the carbon E can be evaluated by the peak area of the adjacent methine group (resonance in the vicinity of 33.7 ppm) and the peak area based on the carbon E' can be evaluated by the peak area of the adjacent methine group (resonance in the vicinity of 33.3 ppm).

Accordingly, by subtracting these peak areas from the total peak areas of the second region and the third region, the peak areas based on the three propylene units chain (PPP (mr) and PPP(rr)) consisting of head-to-tail bonds can be obtained.

Thus, the peak areas of PPP(mm), PPP(mr) and PPP(rr) can be evaluated, and hence the triad tacticity of the propylene units chain consisting of head-to tail bonds can be determined.

Triad tacticity (mm fraction) of the propylene homopolymer is also determined by defining as a proportion of such chains of three propylene units that directions of methyl branches in the propylene chain are the same as each other and each propylene units bonded to each other with head-to-tail bonds, when the main chains are represented by plane-zigzag structure. The triad tacticity (mm fraction) of the propylene homopolymer can be determined from a $^{13}$C-NMR spectrum of the propylene copolymer and the following formula:

$$\text{Triad tacticity (\%)} = \frac{PPP(mm)}{\Sigma I_{CH_3}} \times 100$$

wherein PPP(mm) has the same meanings defined above, and $\Sigma I_{CH_3}$ denotes the total areas of all peaks derived from the methyl groups.

With respect to the chemical shift, the methyl group of the third unit in the five propylene units chain consisting of head-to-tail bonds is set to 21.593 ppm, and the chemical shift of other carbon peak is determined by using the above-mentioned value as a reference.

In this standard, the peak of the methyl group of the second unit in the three propylene units chain represented by PPP(mm) appears in the range of 21.1 to 21.9 ppm, the peak of the methyl group of the second unit in the three propylene units chain represented by PPP(mr) appears in the range of 20.3 to 21.0 ppm and the peak of the methyl group of the second unit in the three propylene units chain represented by PPP(rr) appears in the range of 19.5 to 20.3 ppm.

Here, the propylene homopolymer contains a small amount of partial structure comprising inversely inserted units based on the 2,1-insertion represented by the aforementioned structure (i), in addition to the regular structure consisting of head-to-tail bonds of propylene units.

In the irregular structure represented by the aforementioned structure (i), the aforementioned definition of PPP (mm) is not applied to the carbon A, the carbon B and the carbon C. However, the carbon A and the carbon B resonate in the region of 16.5 to 17.5 ppm, and the carbon C resonates in the vicinity of 20.7 ppm (PPP(mr) region). In the partial structure containing inversely inserted units, not only the peak of the methyl group but also the peaks of the adjacent methylene and methine group must be confirmed. Therefore, the carbon A, the carbon B and the carbon C are not included in the region of PPP(mm).

Thus, the triad tacticity (mm fraction) of the propylene homopolymer can be calculated from the aforementioned formula.

Proportion of inversely inserted units based on 2,1-insertion of propylene monomer In the polymerization, the 1,2-insertion (methylene side is bonded to the catalyst) of the propylene monomer mainly takes place, but the 2,1-insertion insertion thereof sometimes takes place. Therefore, the propylene copolymer and the propylene elastomer contain the inversely inserted units based on the 2,1-insertion represented by the aforementioned structures (i), (ii) and (iii). The proportion of the inversely inserted units based on the 2,1-insertion was calculated from the following formula by using $^{13}$C-NMR.

$$\text{Proportion of inversely inserted units based on 2,1-insertion (\%)} = \frac{0.5 A + 0.25 B}{C + D + 0.5 E} \times 100$$

A: $I\alpha\beta$ [structures (i) and (iii)]
B: $I\alpha\beta$ [structure (ii)]
C: $I\alpha\alpha$
D: $I\alpha\beta$ [structures (i) and (iii)]
E: $I\alpha\gamma + I\alpha\beta$ [structure (ii)] + $I\alpha\delta$ Naming of these peaks was made in accordance with the method by Carman, et al. (Rubber Chem. Tachnol., 44, 781 (1971)). $I\alpha\beta$ and the like indicate the peak areas of $\alpha\beta$-peak and the like.

Homopolymer of propylene contains the inversely inverted units based on the 2,1-insertion. The proportion of the 2,1-propylene monomer insertions to the all propylene insertions was calculated from the following formula.

Proportion of inversely inserted units based on 2,1-insertion (%) =

$$\frac{0.5 \times (\text{area of methyl group resonated at 16.5-17.5 ppm})}{\Sigma I_{CH_3}} \times 100$$

wherein, $\Sigma I_{CH_3}$ is the same as those mentioned before.

Proportion of inversely inserted units based on 1,3-insertion of propylene monomer In the propylene copolymer and the propylene elastomer, the amount of three units chain based on the 1,3-insertion of propylene is determined from $\beta\gamma$-peak (resonance in the vicinity of 27.4 ppm).

In the propylene homopolymer, the amount of 3 unit chain based on the 1,3-insertion of propylene is determined from $\alpha\delta$-peak (resonance in the vicinity of 37.1 ppm) and $\beta\gamma$-peak (resonance in the vicinity of 27.4 ppm).

EFFECT OF THE INVENTION

The novel transition metal compound according to the invention can suitably be used as an olefin polymerization catalyst component.

The olefin polymerization catalyst of the invention has high polymerization activity and polyolefins prepared by the use of the catalyst have a narrow molecular weight distribution, a narrow composition distribution and high molecular weight. When an $\alpha$-olefin of 3 or more carbon atoms is used, obtainable is a polymer having high stereoregularity, being low in proportion of inversely inserted units, and having excellent in heat resistance and rigidity.

The propylene homopolymer according to the present invention is excellent in rigidity, heat resistance, surface hardness, glossiness, transparency and impact strength.

The first-and second propylene copolymers of the present invention (wherein the amount of monomer units derived from an $\alpha$-olefin other than propylene is not more than 5% by mol) are excellent in transparency, rigidity, surface hardness, heat resistance, heat-sealing property, anti-blocking property, anti-bleedout property and impact strength. The propylene copolymers of the present invention (wherein the amount of monomer units derived from an $\alpha$-olefin other than propylene is not less than 5% by mol) are excellent in transparency, environmental aging property, and effective in improving heat-sealing property at low temperature and impact strength.

The third propylene copolymer according to the invention is excellent in rigidity, surface hardness, heat resistance, transparency, heat-sealing property, anti-blocking property and anti-bleedout property, and suitable for films, sheets, containers, stretched yarns, nonwoven fabrics, etc.

The propylene elastomer according the invention is excellent in heat resistance, impact absorbing properties, transparency, heat-sealing properties and anti-blocking properties. Hence, it can be singly used for films, sheets, etc., and moreover it can be suitably used as a modifier of a thermoplastic resin.

EXAMPLE

The present invention is described in more detail with reference to the following examples, but it should be construed that the invention is in no way limited to those examples.

In the present invention, an intrinsic viscosity [$\eta$] and the composition of a copolymer are determined by the following methods.

Further, in some examples, a heat seal-starting temperature and a heat seal-starting temperature after heat treatment, a melting point (Tm), a melt flow rate (MFR), an izod impact strength (IZ) and a film impact strength are measured by the following method.

Intrinsic viscosity [$\eta$]

The intrinsic viscosity [$\eta$] was determined in decahydronaphthalene at 135° C., and expressed by dl/g.

Composition of copolymer

The composition of a propylene copolymer is measured by $^{13}$C-NMR.

Heat seal-starting temperature and heat seal-starting temperature after heat treatment With respect to the T-die film having a width of 30 cm and a thickness of 50 μm prepared using a single screw extruder having a diameter of 30 mm under the conditions of a resin temperature of 210° C. (at a portion of dicer of extruder), a take-off speed of 3 m/min and a temperature of cooling roll of 25° C., a heat seal of two films is carried out using a heat sealer by sealing at various seal bar temperatures under the conditions of a heat seal pressure of 2 kg/cm², a seal time of 1 second and a width of 5 mm to prepare a sealed film having a width of 15 mm. The above-prepared sealed film was allowed to stand overnight.

The heat seal-staring temperature is defined as a temperature of the heat sealer when the peeling resistance of the sealed film becomes 300 g/25 mm, under such conditions that the sealed film is peeled off at 23° C., a peeling speed of 200 mm/min and a peeling angle of 180°.

Separately, another sealed film was subjected to heat treatment at 50° C. for 7 days. The heat seal-starting temperature after heat treatment was measured using the heat treated specimen.

Melting point (Tm)

The melting point was determined from an endothermic curve given by heating about 5 mg of a sample charged in an aluminum pan to 200° C. at a rate of 10° C./min, keeping it at 200° C. for 5 minutes, then cooling it to room temperature at a rate of 20° C./min and heating it again at a rate of 10° C./min. The measurement was conducted using a DSC-7 type apparatus produced by Perkin Elmer Co.

Melt flow rate (MFR)

The MFR is measured in accordance with ASTM D 1238 under a load of 2.16 kg at 230° C.

Izod impact strength (IZ)

The IZ is measured in accordance with ASTM D 256 at 23° C. using a notched specimen of 12.7 mm (width)×6.4 mm (thickness)×64 mm (length).

The specimen is prepared by injection molding at a resin temperature of 200° C. and a molding temperature of 40° C. using a polypropylene composition obtained by dry-blending 20% by weight of a polymer according to the present invention and 80% by weight of a polypropylene (HIPOL™, grade J 700, melt flow rate: 11 g/10 min (at 230° C.), density: 0.91, manufactured by Mitsui Petrochemical Industries, Ltd.), and melt-kneading at 200° C. using a twin-screw extruder.

Film impact strength

The film impact strength is measured using a film impact tester (manufactured by Toyo Seiki K. K., diameter of impact head bulb: ½ inch (12.7 mm φ)).

Example 1

Synthesis of rac-dimethylsilyl-bis{1-(2-ethyl-4-phenylindenyl)}zirconium dichloride Synthesis of 3-(2-biphenylyl)-2-ethylpropionic acid A 500-ml four-necked round flask equipped with a stirrer, a Dimroth condenser, a dropping funnel and a thermometer was charged with 13.46 g (120 mmol) of potassium t-butoxide, 100 ml of toluene and 20 ml of N-methylpyrrolidone.

To the mixture was dropwise added a solution containing 20.7 g (110 mmol) of diethyl ethylmalonate dissolved in 50 ml of toluene under nitrogen atmosphere while warming at 60° C. After the addition was completed, the reaction mixture was stirred for 1 hour at this temperature. Then, to the resulting mixture was dropwise added a solution containing 20.27 g (100 mmol) of 2-phenylbenzylbromide dissolved in 30 ml of toluene. After the addition was completed, the temperature was elevated and the resulting mixture was stirred under reflux for 2 hours. The reaction mixture was poured onto 200 ml of water and the resulting mixture was adjusted with addition of 2N HCl to pH 1. The organic phase was separated and the aqueous phase was further extracted with 100 ml of toluene three times. The combined organic phase was washed with a saturated aqueous solution of sodium chloride until the resulting material was neutralized, followed by drying over anhydrous $Na_2SO_4$. The solvent was concentrated under reduced pressure to obtain 36.7 g of a yellow-orange liquid.

A 1-liter four-necked round flask equipped with a stirrer, a Dimroth condenser, a dropping funnel and a thermometer was charged with 67.3 g (1.02 mol) of potassium hydoxide and 160 ml of an aqueous solution of methanol (methanol/water=4/1(v/v)). To the mixture was dropwise added a solution containing the above-obtained concentrate dissolved in 50 ml of an aqueous solution of methanol (methanol/water=4/1(v/v)) at room temperature under a nitrogen atmosphere. After the addition was completed, the temperature was elevated and the resulting mixture was stirred under reflux for 4 hours. Thereafter, the temperature was cooled to room temperature and the resultant precipitated solid was filtered. The residue was dissolved in water and acidified with addition of sulfuric acid to pH 1. The resulting solution was extracted with 100 ml of methylene chloride five times. The combined organic phase was dried over anhydrous $Na_2SO_4$. The solvent was concentrated under reduced pressure to obtain 24.2 g of a white solid.

Then, a 300-ml three-necked round flask equipped with a stirring bar, a Dimroth condenser, a thermometer was charged with 24.2 g of the above-obtained white solid, 56 ml of acetic acid, 37 ml of water and 13.1 ml of concentrated sulfuric acid, and the mixture was stirred under reflux for 6 hours under a nitrogen atmosphere. After the reaction was completed, the acetic acid was evaporated under reduced pressure. To the resulting material was added 50 ml of water, which was then extracted with 50 ml of methylene chloride three times. The combined organic phase was washed with 50 ml of a saturated aqueous solution of sodium chloride, followed by drying over anhydrous $Na_2SO_4$. The solvent was evaporated under reduced pressure. The residue was chromatographed on silica gel (eluting with hexane/ethyl acetate (2/1), and hexane/ethyl acetate (1/1), parts by volume) to obtain 13.7 g of the desired product as a white solid (yield: 54%).

| FD-MS | 2.54 (M⁺) |
|---|---|
| mp. | 91.2–94.0° C. |
| NMR (CDCl₃, 90Hz) | δ=0.71(t, J = 7.2Hz, 3H, CH₃); |
| | 1.16–1.58(m, 2H); |
| | 2.32 (bquin, J=7.0Hz, 1H, —CH—); |
| | 2.61–2.99(m, 2H); |
| | 6.89–7.47(m, 9H). |
| IR (Kbr disk) | 1696 cm⁻¹ (ν_c=o) |

Synthesis of 3-(2-biphenylyl)-2-ethylpropionyl chloride

A 100-ml three-necked round flask equipped with a stirring bar, a Dimroth condenser, a thermometer and a NaOH trap was charged with 13.3 g (52.4 mmol) of 3-(2-biphenylyl)-2-ethylpropionic acid and 25.9 ml (355 mmol) of thionyl chloride, and the resulting mixture was stirred under reflux for 2.5 hours under a nitrogen atmosphere. After the reaction was completed, the unreacted thionyl chloride was distilled off under reduced pressure to obtain 15.2 g of a crude product as a yellow-orange liquid. The thus obtained acid chloride was used in the next reaction without further purification.

IR (Neat): 1786 cm$^{-1}$ ($v_{c=o}$)

Synthesis of 4-ethyl-2-phenyl-1-indanone

A 200-ml three-necked round flask equipped with a stirring bar, a Dimroth condenser, a dropping funnel, a thermometer and a NaOH trap was charged with 8.04 g (60.3 mmol) of anhydrous aluminum chloride and 50 ml of carbon disulfide. To the mixture was dropwise added a solution containing 15.2 g (52.4 mmol) of the above-obtained 3-(2-biphenylyl)-2-ethyl propionyl chloride under a nitrogen atmosphere at 0° C. After the addition was completed, the temperature in the flask was elevated to room temperature and the reaction mixture was stirred for 1 hour. The reaction mixture was poured onto 200 ml of ice-water and extracted with 100 ml of ether two times. The combined organic phase was washed with 100 ml of a saturated aqueous solution of NaHCO$_3$ and further 100 ml of a saturated aqueous solution of sodium chloride, followed by drying over anhydrous Na$_2$SO$_4$. The solvent was evaporated under reduced pressure. The residue was chromatographed on silica gel (eluting with hexane/ethyl acetate (10/1), parts by volume) to obtain 10.8 g of the desired product as a yellow solid (yield: 88%).

| NMR (CDCl$_3$, 90 MHz) | δ=0.98(t, J=7.2Hz, 3H, CH$_3$); 1.60–2.20(m, 2H); 2.42–2.82(m, 1H, —CH—); 2.80(dd, J=3.8Hz, 16.5Hz, 1H); 3.36(dd, J=7.6Hz, 16.5Hz, 1H); 7.09–7.91(m, 8H). |
|---|---|
| IR (Neat) | 1705 cm$^{-1}$ ($v_{c=o}$) |

Synthesis of 2-ethyl-1-hydroxy-4-phenylindene

A 200-ml three-necked round flask equipped with a stirring bar, a Dimroth condenser, a dropping funnel and a thermometer was charged with 0.85 g (22.6 mmol) of sodium borohydride and 28 ml of ethanol. To the mixture was dropwise added a solution containing 10.6 g (45.1 mmol) of the above-obtained 2-ethyl-4-phenyl-1-indanone dissolved in 20 ml of ethanol at room temperature under a nitrogen atmosphere. After the addition was completed, the temperature of was elevated to 50° C., and the reaction mixture was stirred for 3.5 hours. After the reaction was completed, the unreacted sodium borohydride was decomposed by acetone. Then, the reaction mixture was concentrated under reduced pressure, and then dissolved in 50 ml of water and extracted with 50 ml of ether. After the organic phase was separated, the aqueous phase was extracted with 50 ml of ether two times. The combined organic phase was washed with 100 ml of a saturated aqueous solution of sodium chloride, followed by drying over anhydrous Na$_2$SO$_4$. The solvent was evaporated under reduced pressure to obtain 10.67 g of the desired product as a pasty pale yellow liquid (mixture of two kinds of isomers) (yield: 99%).

| NMR (CDCl$_3$, 90 MHz) | δ=1.02(t, J=7.1Hz, 3H, CH$_3$); 1.31–3.28(m, 5H); 4.86, 5.03(each d, each J=6.4Hz, 5.1Hz, total 1H, —CH—O—); 7.10–7.66(m, 8H). |
|---|---|
| IR (Neat) | 3340 cm$^{-1}$ ($v_{c=o}$) |

Synthesis of 2-ethyl-4-phenylindene

A 300-ml four-necked round flask equipped with a stirring bar, a dropping funnel and a thermometer was charged with 9.78 g (41.3 mmol) of 2-ethyl-1-hydroxy-4-phenylindane, 17.2 ml (123.8 mmol) of triethylamine, 0.25 g (2.1 mmol) of 4-dimethylaminopyridine and 98 ml of methylene chloride. To the mixture was dropwise added a solution containing 6.4 ml (82.5 mmol) of methanesulfonyl chloride dissolved in 6.5 ml of methylene chloride under a nitrogen atmosphere at 0° C. After the addition was completed, the reaction mixture was stirred for 3.5 hours at this temperature. The reaction mixture was poured onto 250 ml of ice-water. Then, the organic phase was separated and the aqueous phase was further extracted with 50 ml of methylene chloride two times. The combined organic phase was washed with a saturated aqueous solution of NaHCo$_3$, and then a saturated aqueous solution of sodium chloride, followed by drying over anhydrous Na$_2$SO$_4$. The solvent was evaporated under reduced pressure. The residue was chromatographed on silica gel (eluting with hexane) to obtain 6.56 g of the desired product as a pale yellow liquid (mixture of two kinds of isomers) (yield: 73%).

NMR (CDCl$_3$, 90 MHz): δ=1.20(t, J=7.6 Hz, 3H, CH$_3$); 2.49(q, J=7.6 Hz, 2H); 3.41(s, 2H); 6.61, 6.72 (each bs, total 1H); 7.09–8.01(m, 8H).

Synthesis of dimethylsilyl-bis(2-ethyl-4-phenylindene)

A 200-ml three-necked round flask equipped with a stirring bar, a Dimroth condenser, a dropping funnel and a thermometer was charged with 5.0 g (22.8 mmol) of 2-ethyl-4-phenylindene, 80 mg (0.63 mmol) of copper thiocyanate and 50 ml of anhydrous ether. To the mixture was gradually dropwise added 15.7 ml (25.1 mmol) of a 1.6M solution of n-butyl lithium in hexane under a nitrogen atmosphere at 0° C. After the addition was completed, the temperature was elevated to room temperature, the reaction mixture was stirred for 1 hour. Then, to the reaction mixture was gradually dropwise added a solution containing 1.52 ml (12.6 mmol) of dimethyldichlorosilane dissolved in 4.5 ml of anhydrous ether. After the addition was completed, the reaction mixture was stirred for 12 hours at room temperature. The reaction mixture was filtered through Celite, and the filtrate was poured onto 50 ml of a saturated aqueous solution of ammonium chloride. After the organic phase was separated, the aqueous phase was extracted with 50 ml of ether. The combined organic phase was washed with a saturated aqueous solution of sodium chloride, followed by drying over anhydrous Na$_2$SO$_4$. The solvent was evaporated under reduced pressure. The residue was chromatographed on silica gel (eluting with hexane, and hexane/methylene chloride (20/1), parts by volume) to obtain 4.5 g of the desired product (mixture of two kinds of isomers) as a pale yellow solid (yield: 80%).

| | |
|---|---|
| NMR (CDCl$_3$, 90 MHz) | δ=−0.23, −0.17(each s, total 6H, Si—CH$_3$); 1.12, 1.19(each t, each J=7.4Hz, 6H, CH$_3$); 2.44(bq, J=7.4Hz, 4H);<br>$\quad\mid$<br>3.81(s, 2H, —CH—Si);<br>6.75(bs, 2H, 3-H—Ind);<br>6.88–7.74(m, 16H). |

Synthesis of rac-dimethylsilyl-bis{1-(2-ethyl-4-phenylindenyl)}zirconium dichloride A 50-ml three-necked round flask equipped with a stirring bar, a condenser, a dropping funnel and a thermometer was charged with 0.84 g (1.69 mmol) of dimethylsilyl-bis(2-ethyl-4-phenylindene) and 17 ml of anhydrous ether. To the mixture was gradually dropwise added 2.25 ml (3.56 mmol) of a 1.58M solution of n-butyl lithium in hexane at room temperature. After the addition was completed, the reaction mixture was stirred for 13.5 hours. To the resulting solution was gradually added 0.395 g (1.69 mmol) of ZrCl$_4$ at −70° C. After the addition was completed, the mixture was allowed to warm to room temperature overnight. Then, the solvent was evaporated at room temperature under reduced pressure. To the resulting material was added 30 ml of methylene chloride. Then, the insoluble material was filtered off and the filtrate was concentrated and crystallized at room temperature. After the precipitates were filtered, the residue was washed with 3 ml of anhydrous ether two times, followed by drying under reduced pressure to obtain 0.17 g of the desired product as an orange-yellow solid (yield: 15%).

NMR (CDCl$_3$, 90 MHz): δ=1.09(t, J=7.3 Hz, 6H, CH$_3$); 1.34 (s, 6H, Si—CH$_3$); 2.46 (quin, J=7.3 Hz, 2H) 2.73 (quin, J=7.3 Hz, 2H) 6.96 (s, 2H, 3-H-Ind); 6.99–7.88 (m, 16H).

Example 2

A 2-liter gas through type-glass reactor thoroughly purged with nitrogen was charged with 1.7 liters of toluene. The reactor was cooled to −30 ° C., and the reaction system was sufficiently saturated by passing through propylene at a flow rate of 100 liters/hr and hydrogen at a flow rate of 10 liters/hr. Then, to the reactor were added 4.25 mmol of triisobutylaluminum, 8.5 mmol (in terms of Al atom) of methylaluminoxane and 0.017 mmol (in terms of Zr atom) of rac-dimethylsilyl-bis{1-(2-ethyl-4-phenylindenyl)}zirconium dichloride. While maintaining the temperature of the reaction system at −30° C., the polymerization was carried out for 45 minutes. The polymerization was stopped by the addition of a small amount of methanol. The polymerization suspension was added to 3 liters of methanol containing a small amount of hydrochloric acid, which was then sufficiently stirred and filtered. The resulting polymer was washed with a large amount of methanol and dried at 80° C. for 10 hours.

The amount of the thus obtained polymer was 51.3 g. The polymerization activity was 4.02 kg-PP/mmol-Zr.hr, the intrinsic viscosity [η] was 3.37 dl/g, and Mw/Mn was 2.22. In the polymer, the triad tacticity was 99.7%, the proportion of the inversely inserted units based on the 2,1-insertion of the propylene monomer was 0.10%, and the proportion of the inversely inserted units based on the 1,3-insertion of the propylene monomer was less than the detectable lower limit (less than 0.03%).

The results are shown in Table 1 (I) and (II).

Example 3

The polymerization was carried out in the same manner as in Example 2 except that propylene and ethylene were passed through at a flow rate of 100 liters/hr and a flow rate of 2 liters/hr, respectively, 0.65 mmol of triisobutylaluminum and 0.0026 mmol (in terms of Zr atom) of the rac-dimethylsilyl-bis{1-(2-ethyl-4-phenylindenyl)}zirconium dichloride were used, and the system was maintained at 60° C., to obtain a polymer.

The amount of the thus obtained polymer was 60.7 g. The polymerization activity was 31.1 kg-PP/mmol-Zr.hr, the intrinsic viscosity [η] was 3.01 dl/g, and Mw/Mn was 2.18. In the polymer, the triad tacticity was 99.5%, the proportion of the inversely inserted units based on the 2,1-insertion of the propylene monomer was 0.15%, and the proportion of the inversely inserted units based on the 1,3-insertion of the propylene monomer was less than the detectable lower limit (less than 0.03%).

The results are shown in Table 1 (I) and (II).

Comparative Example 1

The polymerization was carried out in the same manner as in Example 3 except that the rac-dimethylsilyl-bis{1-(2-methyl-4-phenylindenyl)}zirconium dichloride was used in place of the rac-dimethylsilyl-bis{1-(2-ethyl-4-phenylindenyl)}zirconium dichloride.

The amount of the thus obtained polymer was 4.7 g. The polymerization activity was 2.4 kg-PP/mmol-Zr.hr, the intrinsic viscosity [H] was 4.05 dl/g, and Mw/Mn was 2.18. In the polymer, the triad tacticity was 98.6%, the proportion of the inversely inserted units based on the 2,1-insertion of the propylene monomer was 0.33%, and the proportion of the inversely inserted units based on the 1,3 insertion of the propylene monomer was less than the detectable lower limit (less than 0.03%).

The results are shown in Table 1 (I) and (II).

Example 4

A 500-ml gas through type-glass reactor thoroughly purged with nitrogen was charged with 250 ml of toluene. The reactor was cooled to 0° C., and the reaction system was sufficiently saturated by passing through propylene at a flow rate of 160 liters/hr and ethylene at a flow rate of 40 liters/hr. Then, to the reactor were added 0.25 mmol of triisobutylaluminum, 0.5 mmol (in terms of Al atom) of methylaluminoxane and 0.001 mmol (in terms of Zr atom) of rac-dimethylsilyl-bis{1-(2-ethyl-4-phenylindenyl)}zirconium dichloride. While maintaining the temperature of the reaction system at 0° C., the polymerization was carried out for 10 minutes. The polymerization was stopped by the addition of a small amount of methanol. The polymerization suspension was poured onto 2 liters of methanol containing a small amount of hydrochloric acid, which was then sufficiently stirred and filtered. The resulting polymer was washed with a large amount of methanol and dried at 80° C. for 10 hours.

The amount of the thus obtained polymer was 5.62 g. The polymerization activity was 33.7 kg-polymer/mmol-Zr.hr. The ethylene content was 3.9% by mol, the intrinsic viscosity [η] was 1.80 dl/g, Mw/Mn was 2.15, and Tm was 126° C. In the polymer, the triad tacticity was 99.3%, the proportion of the inversely inserted units based on the 2,1-insertion of the propylene monomer was 0.12%, and the proportion of the inversely inserted units based on the 1,3-insertion propylene monomer was less than the detectable lower limit (less than 0.03%).

The results are shown in Table 1 (I) and (II).

The film of the polymer had a heat seal-starting temperature of 129° C. and a heat seal-starting temperature after heat treatment of 132° C.

The results are shown in Table 2.

Example 5

The polymerization was carried out in the same manner as in Example 4 except that the reaction system was sufficiently saturated by passing through propylene at a flow rate of 140 liters/hr and ethylene at a flow rate of 60 liters/hr, respectively. The thus obtained polymer solution was poured onto 2 liters of methanol containing a small amount of hydrochloric acid to precipitate a polymer. The methanol was sufficiently removed, and the resulting polymer was dried at 130° C. for 10 hours.

The amount of the thus obtained polymer was 6.63 g and the polymerization activity was 39.8 kg-polymer/mmol-Zr.hr. The ethylene content was 8.7% by mol, the intrinsic viscosity [η] was 1.66 dl/g, Mw/Mn was 2.46, and Tm was 105° C. In the polymer, the triad tacticity was 99.2%, the proportion of the inversely inserted units based on the 2,1-insertion of the propylene monomer was 0.12%, and the proportion of the inversely inserted units based on the 1,3-insertion of the propylene monomer was less than the detectable lower limit (less than 0.03%).

The results are shown in Table 1 (I) and (II).

The film of the polymer had a heat seal-starting temperature of 106° C. and a heat seal-starting temperature after heat treatment of 109° C.

The results are shown in Table 2.

Example 6

The polymerization reaction was carried out in the same manner as in Example 4 except that the reaction system was sufficiently saturated by passing through propylene at a flow rate of 100 liters/hr and ethylene at a flow rate of 100 liters/hr, respectively. The thus obtained polymer solution was poured onto 2 liters of methanol containing a small amount of hydrochloric acid to precipitate a polymer. The methanol was sufficiently removed and the resulting polymer was dried at 130° C. for 10 hours.

The amount of the thus obtained polymer was 8.95 g and the polymerization activity was 53.7 kg-polymer/mmol-Zr.hr. The ethylene content was 28.9% by mol, the intrinsic viscosity [η] was 1.34 dl/g, and Mw/Mn was 1.95. In the polymer, the triad tacticity was 98.5%, the proportion of the inversely inserted units based on the 2,1-insertion of the propylene monomer was 0.09%, and the proportion of the inversely inserted units based on the 1,3-insertion of the propylene monomer was less than the detectable lower limit (less than 0.03%).

The results are shown in Table 1 (I) and (II).

The copolymer had an izod impact strength of 28 kg.cm/cm and a film impact strength of 5300 kg.cm/cm.

The results are shown in Table 2.

Example 7

Synthesis of rac-dimethylsilyl-bis{1-(2-ethyl-4-(1naphthyl)indenyl)}zirconium dichloride Synthesis of 3-(2-bromophenylyl)-2-ethylpropionic acid A 2-liter four-necked round flask equipped with a stirrer, a Dimroth condenser, a dropping funnel and a thermometer was charged with 44.2 g (394 mmol) of potassium t-butoxide, 392 ml of toluene and 30 ml of N-methylpyrrolidone. To the mixture was dropwise added a solution containing 61.2 g (325 mmol) of diethyl ethylmalonate dissolved in 61 ml of toluene under a nitrogen atmosphere at 60° C. After the addition was completed, the reaction mixture was stirred for 1 hour at this temperature. Then, to the resulting mixture was dropwise added a solution containing 75.4 g (302 mmol) of 2-bromobenzylbromide dissolved in 75 ml of toluene. After the addition was completed, the temperature was elevated and the resulting mixture was stirred under reflux for 5 hours. The reaction mixture was poured onto 300 ml of water and adjusted with 10% sulfuric acid to pH 1. The organic phase was separated and the aqueous phase was extracted with 100 ml of ether three times. The combined organic phase was washed with 200 ml of a saturated aqueous solution of sodium bicarbonate and then 150 ml of a saturated aqueous solution of sodium chloride three times, followed by drying over anhydrous Na$_2$SO$_4$. The solvent was concentrated under reduced pressure to obtain 111.1 g of a concentrate as a yellow liquid.

A 2-liter four-necked round flask equipped with a stirrer, a Dimroth condenser, a dropping funnel and a thermometer was charged with 195 g (2.96 mol) of potassium hydoxide and 585 ml of an aqueous solution of methanol (methanol/water=4/1(v/v)). To the mixture was dropwise added the above-obtained concentrate at room temperature under a nitrogen atmosphere. After the addition was completed, the temperature was elevated and the resultant mixture was stirred under reflux for 3 hours. Thereafter, the temperature was cooled to room temperature and the precipitated white solid was filtered. The filtrate was concentrated and cooled to obtain a second crop. The same procedure was repeated as described above to obtain a third crop. The combined crops were slurried in hexane and filtered. The solid thus obtained was dried to obtain 101.5 g of a white powder. The white powder was dissolved in 400 ml of water and the resulting solution was acidified with addition of 50% H$_2$SO$_4$ aq. to pH 1. The resulting mixture was extracted with 200 ml of methylene chloride five times. The combined organic phase was dried over anhydrous Na$_2$SO$_4$. The solvent was concentrated under reduced pressure to obtain 74.2 g of a hard white solid.

Then, a 300-ml three-necked round flask equipped with a stirring bar, a Dimroth condenser, a thermometer was charged with the above-obtained white solid. Then, the solid was heated to 200° C. and stirred for 5 hours under a nitrogen atmosphere. After the reaction was completed, the reaction product was cooled to room temperature to obtain 61.2 g of the desired product as a pale yellow-white solid (yield: 79%).

| FD-MS | 256 (M$^+$), 258 (M$^+$ +2) |
|---|---|
| NMR (CDCl$_3$, 90 MHz) | δ = 1.0 (t, J=7.0 Hz, 3H, CH$_3$); 1.40–1.85 (m, 2H); 2.53–3.12 (m, 3H); 6.88, 7.66 (m, 3H) |

Synthesis of 3-(2-bromophenyl)-2-ethylpropionyl chloride

A 300-ml three-necked round flask equipped with a stirring bar, a Dimroth condenser, a thermometer and a NaOH trap was charged with 60.86 g (237 mmol) of 3-(2-bromophenylyl)-2-ethylpropionic acid, 40 ml of benzene and 120 ml of thionyl chloride, and the mixture was stirred under reflux for 1.5 hours under a nitrogen atmosphere. After the reaction was completed, the unreacted thionyl chloride was distilled off under reduced pressure to obtain the crude product as a yellow liquid. The thus obtained acid chloride was used in the next reaction without further purification.

Synthesis of 4-bromo-2-ethyl-1-indanone

A 1-liter three-necked round flask equipped with a stirring bar, a Dimroth condenser, a dropping funnel, a thermometer and a NaOH trap was charged with 36.3 g (272 mmol) of anhydrous aluminum chloride and 280 ml of carbon disulfide. To the mixture was dropwise added a solution containing the above obtained 3-(2-bromophenyl)-2-ethylpropionyl chloride dissolved in 50 ml of carbon disulfide under a nitrogen atmosphere at 0° C. After the addition was completed, the temperature in the flask was elevated to room temperature and the reaction mixture was stirred for 1 hour. The reaction mixture was poured onto 1 liter of ice-water and extracted with 300 ml of ether two times. The combined organic phase was washed with a saturated aqueous solution of $NaHCO_3$, and then a saturated aqueous solution of sodium chloride, followed by drying over anhydrous $Na_2SO_4$. The solvent was evaporated under reduced pressure to obtain 56.9 g of the desired product as a slightly pasty red-brown liquid. The thus obtained ketone was used in the next reaction without further purification.

Synthesis of 4-bromo-2-ethyl-1-trimethylsilyloxyindane

A 500-ml three-necked round flask equipped with a stirring bar, a Dimroth condenser, a dropping funnel and a thermometer was charged with 4.97 g (118 mmol) of sodium borohydride and 200 ml of ethanol. To the mixture was dropwise added a solution containing 56.93 g of the above-obtained 4-bromo-2-ethyl-1-indanone dissolved in 85 ml of ethanol at room temperature under a nitrogen atmosphere. After the addition was completed, the reaction mixture was stirred for additional 4 hours. After the reaction was completed, the reaction mixture was cooled and the unreacted sodium borohydride was decomposed by acetone. Then, the reaction mixture was concentrated under reduced pressure, and dissolved in 300 ml of water and extracted 300 ml of ether. After the organic phase was separated, the aqueous phase was extracted with 100 ml of ether three times. The combined organic phase was washed three times with 150 ml of a saturated aqueous solution of sodium chloride, followed by drying over anhydrous $Na_2SO_4$. The solvent was evaporated under reduced pressure to obtain 58.92 g of a flesh colored solid.

A 500-ml four-necked round flask equipped with a stirring bar, a Dimroth condenser, a dropping funnel and a thermometer was charged with 58.91 g (244 mmol) of the above-obtained solid, 43.3 ml (307 mmol) of triethylamine and 280 ml of methylene chloride. To the mixture was gradually dropwise added a solution containing 37.2 ml (293 mmol) of $Me_3SiCl$ dissolved in 15 ml of methylene chloride under a nitrogen atmosphere at 0° C. After the addition was completed, the temperature was elevated to room temperature, and the reaction mixture was stirred for additional 3.5 hours. The reaction mixture was poured onto 100 ml of water. Then, the organic phase was separated and the aqueous phase was extracted with 100 ml of methylene chloride two times. The combined organic phase was washed with 100 ml of water three times, followed by drying over anhydrous $Na_2SO_4$. The solvent was evaporated under reduced pressure. The residue was distilled under reduced pressure to obtain 69.9 g of the desired product (mixture of two isomers) as a colorless liquid (total yield: 95% from 3-(2-bromophenylyl)-2-ethylpropionic acid).

mp.: 133°–135° C./2 mmHg

FD-MS: 312 ($M^+$), 314($M^+$+2)

NMR ($CDCl_3$, 90 MHz): δ=0.17, 0.24(each s, total 9H, Si—$CH_3$); 0.79–1.12(m, 3H); 1.16–3.31(m, 5H); 4.82, 5.10 (each bd, each J=6.4 Hz, total 1H, —CH—O—); 6.91–7.46 (m, 3H).

Synthesis of 2-ethyl-4-(1-naphthyl)phenylindene

A 300-ml three-necked round flask equipped with a stirring bar, a Dimroth condenser, a dropping funnel and a thermometer was charged with 11.4 g (36.4 mmol) of 4-bromo-2-ethyl-1-trimethylsilyloxyindane, 0.13 g (0.18 mmol) of $PdCl_2$ (dppf) and 35 ml of anhydrous ether. To the resulting mixture was dropwise added 101 ml (72.8 mmol) of a 0.72M solution of 1-naphthylmagnesiumbromide in ether/benzene at room temperature under a nitrogen atmosphere. After the addition was completed, the reaction mixture was stirred for 1 hour. Then, the temperature in the flask was elevated to 50° to 51° C., and the reaction mixture was stirred for additional 5 hours. After the reaction was completed, to the reaction mixture was added 135 ml of 5N hydrochloric acid at 0° C. to decompose the excess amount of Grignard reagent, and the resulting mixture was extracted with 100 ml of ether two times. The combined organic phase was washed with a saturated aqueous solution of sodium bicarbonate, and then a saturated aqueous solution of sodium chloride, followed by drying over anhydrous $Na_2SO_4$. The solvent was evaporated under reduced pressure to obtain 20.5 g of a product as a red-brown liquid.

Then, the above-obtained red-brown liquid was diluted with 20 ml of tetrahydrofuran. To the mixture was added 5 ml of 12% hydrochloric acid and the reaction mixture was stirred at room temperature overnight. After the reaction was completed, to the reaction mixture was added 100 ml of ether and the organic phase was separated. The organic phase was washed with a saturated aqueous solution of sodium bicarbonate, and then a saturated aqueous solution of sodium chloride, followed by drying over anhydrous $Na_2SO_4$. The solvent was evaporated under reduced pressure. The residue was chromatographed on silica gel (Silica gel 60 from MERCK Co., 70–230 mesh, eluting with hexane, and then hexane/ethyl acetate (⅕, parts by volume)) to obtain 9.0 g of the desired product (mixture of two isomers) as a yellow solid (yield: 98%).

FD-MS: 270 ($M^+$)

NMR ($CDCl_3$, 90 MHz): δ=1.20(t, J=7.4 Hz, 3H, $CH_3$); 2.38(bq, J=7.4 Hz, 2H); 3.02, 3.42(each s, total 2H); 6.54(bs, 1H); 6.19–8.12(m, 10H)

Synthesis of dimethylsilyl-bis{1-(2-ethyl-4-(1-naphthyl)indene)}

A 200-ml three-necked round flask equipped with a stirring bar, a Dimroth condenser, a dropping funnel and a thermometer was charged with 4.97 g (18.4 mmol) of 2-ethyl-4-(1-naphthyl)indene, 50 mg (0.51 mmol) of copper cyanide and 53 ml of anhydrous ether. To the mixture was gradually dropwise added 12.8 ml (20.2 mmol) of a 1.58M solution of n-butyl lithium in hexane under a nitrogen atmosphere at −10° C. After the addition was completed, the temperature was elevated to room temperature and the reaction mixture was stirred for 4 hours. Then, to the reaction mixture was gradually dropwise added a solution containing 1.24 ml (10.1 mmol) of dimethyldichlorosilan dissolved in 5 ml of anhydrous ether. After the addition was completed, the reaction mixture was stirred for 15 hours at room temperature. The reaction mixture was poured onto 50 ml of a saturated aqueous solution of ammonium chloride and filtered through Celite. The organic phase was separated and the aqueous phase was extracted with 50 ml of ether. The combined organic phase was washed with a saturated aqueous solution of sodium chloride, followed by drying over anhydrous $Na_2SO_4$. The solvent was evaporated under reduced pressure. The residue was chromatographed on silica gel (eluting with hexane) to obtain 3.2 g of the desired product (mixture of two isomers) as a yellow solid (yield: 58%).

FD-MS: 596 ($M^+$)

NMR ($CDCl_3$, 90 MHz): δ=–0.20, –0.20(each s, total 6H, Si—$CH_3$); 0.82–1.41(m, 6H, $CH_3$); 2.23, 2.74(m, 4H); 3.84–4.10(m, 2H, —CH—Si); 6.20, 6.30(each bd, 2H); 6.98–8.14(m, 20H)

Synthesis of rac-dimethylsilyl-bis{1-(2-ethyl-4-(1-naphthyl)indenyl)}zirconium dichloride A 100-ml three-necked round flask equipped with a stirring bar, a condenser having beads, a dropping funnel and a thermometer was charged with 2.0 g (3.36 mmol) of dimethylsilyl-bis(2-ethyl-4-(1-naphthyl)indene and 40 ml of anhydrous ether under an argon atmosphere. To the mixture was gradually dropwise added 4.58 ml (7.06 mmol) of a 1.54M solution of n-butyl lithium in hexane at room temperature. After the addition was completed, the reaction mixture was stirred for 17.5 hours. The resulting reaction solution was cooled to –75° C. Then, to the solution was gradually added 0.83 g (3.56 mmol) of $ZrCl_4$. After the addition was completed, the mixture was allowed to warm to room temperature overnight.

The thus obtained red-yellow reaction slurry was filtered, and washed with 45 ml of anhydrous ether. To the residue were added 60 ml of methylene chloride and 40 ml of anhydrous ether, and then the insoluble material was filtered off. The filtrate was concentrated to dryness at room temperature. The residue was dissolved in 15 ml of methylene chloride and concentrated to about ⅓ of total volume of the mixture. Then, 2 ml of anhydrous ether to give the precipitate. The precipitate was filtered and washed with 2 ml of anhydrous ether, followed by drying under a reduced pressure to obtain 0.12 g of the desired product as a yellow-orange powder (yield: 5%).

NMR ($CDCl_3$, 90 MHz): δ=1.04(t, J=7.4 Hz, 6H, $CH_3$); 1.38 (s, 6H, Si—$CH_3$); 2.12–3.02 (m, 4H); 6.53 (s, 2H, 3-H-Ind); 6.86–8.02 (m, 20H).

Example 8

The polymerization was carried out in the same manner as in Example 3 except that the rac-dimethylsilyl-bis{1-(2-ethyl-4-(1-naphthyl)indenyl)}zirconium dichloride was used in place of the rac-dimethylsilyl-bis{1-(2-ethyl-4-phenylindenyl)}zirconium dichloride as a transition metal compound catalyst component.

The amount of the thus obtained polymer was 20.2 g and the polymerization activity was 10.4 kg-PP/mmol-Zr.hr. The intrinsic viscosity [η] was 3.08 dl/g, and Mw/Mn was 2.09. In the polymer, the triad tacticity was 99.7%, the proportion of the inversely inserted units based on the 2,1-insertion of the propylene monomer was 0.12%, and the proportion of the inversely inserted units based on the 1,3-insertion of the propylene monomer was less than the detectable lower limit (less than 0.03%).

The results are shown in Table 1 (I) and (II).

Example 9

The polymerization reaction was carried out in the same manner as in Example 5 except that the rac-dimethylsilyl-bis{1-(2-ethyl-4-(1naphthyl)indenyl)}zirconium dichloride was used in place of the rac-dimethylsilyl-bis{1-(2-ethyl-4-phenylindenyl)}zirconium dichloride as a transition metal compound catalyst component.

The amount of the thus obtained polymer was 2.08 g and the polymerization activity was 12.5 kg-polymer/mmol-Zr.hr. The ethylene content was 7.9% by mol, the intrinsic viscosity [η] was 1.39 dl/g, Mw/Mn was 2.33, and Tm was 109° C. In the polymer, the triad tacticity was 99.2%, the proportion of the inversely inserted units based on the 2,1-insertion of the propylene monomer was 0./10%, and the proportion of the inversely inserted units based on the 1,3-insertion of the propylene monomer was less than the detectable lower limit (less than 0.03%).

The results are shown in Table 1 (I) and (II).

The film of the polymer had a heat seal-starting temperature of 106° C. and a heat seal-starting temperature after heat treatment of 110° C.

The results are shown in Table 2.

Example 10

Synthesis of rac-dimethylsilyl-bis{1-(2-n-propyl-4-(1naphthyl)indenyl)}zirconium dichloride Synthesis of 3-(2-bromophenyl)-2-n-propylpropionic acid A 1-liter four-necked round flask equipped with a stirrer, a Dimroth condenser, a dropping funnel and a thermometer was charged with 37 g (330 mmol) of potassium t-butoxide, 32 ml (334 mmol) of N-methylpyrrolidone and 400 ml of toluene. To the mixture was added dropwise a solution containing 60.7 g (300 mmol) of n-diethyl propylmalonic acid dissolved in 50 ml of toluene at the reaction temperature of 5° to 10° C. for 30 minutes with stirring in an ice bath. After the addition was completed, the mixture was stirred at 45° C. for 30 minutes and at 65° C. for additional 1 hour. The resulting solution turned a cream colored heterogeneous material immediately after heating.

To the resultant material was added dropwise a solution containing 75 g (300 mmol) of 2-bromobenzylbromide dissolved in 50 ml of toluene at the reaction temperature of 5° to 15° C. for 30 minutes in an ice bath. After the addition was completed, the mixture was stirred at 65° C. for 30 minutes. The temperature was elevated and the reaction mixture was heated under reflux for 1 hour. The color of the reaction product was gradually changed to gray. After allowing to cool, the reaction product was poured onto 500 ml of water and the mixture was controlled to pH 1 with addition of an aqueous solution of 10% sulfuric acid. The organic phase was separated and the aqueous phase was extracted with 100 ml of toluene five times. The combined organic phase was washed with 200 ml of NaCl aq. four times, followed by drying over $MgSO_4$. The solvent was evaporated to give 114 g of a brown liquid.

A 1-liter four-necked round flask equipped with a stirrer, a Dimroth condenser, a dropping funnel and a thermometer was charged with the above-obtained liquid and 200 ml of methanol, and stirred. To the mixture was added a solution containing 237 g (content: 85%, 3.59 mol) of potassium hydroxide dissolved in 520 ml of methanol and 180 ml of water. Then, this flask was heated at 90° C. and the mixture was refluxed for 5 hours. Thereafter, almost of the methanol was evaporated using an evaporator and 500 ml of water was added thereto to give a homogeneous solution. While cooling with ice, the homogeneous solution was controlled to pH 1 with addition of an aqueous solution of 10% sulfuric acid. The resultant white precipitate was separated by filtration. Then, the organic phase was separated from the filtrate, and the aqueous phase was extracted with 200 ml of ether six times. The combined organic phase was dried over anhydrous $MgSO_4$. The solvent was evaporated to give 94 g of a yellow-white semisolid.

Then, the semisolid was charged into 1-liter round flask, and heated for 10 minutes at 180° C. After heating, the resulting product was cooled to give 78.0 g of the desired product as a brown transparent liquid (yield: 96%).

FD-MS: 270 ($M^+$), 272 ($M^++2$)

NMR ($CDCl_3$, 90 MHz): $\delta$=0.95 (t, J=7.0 Hz, 3H, $CH_3$); 1.10–2.00 (m, 4H); 2.60–3.25 (m, 3H); 6.90–7.80 (m, 4H)

Synthesis of 3-(bromophenyl)-2-n-propylpropionyl chloride

A 500-ml three-necked round flask equipped with a stirring bar, a Dimroth condenser, a thermometer and a NaOH trap was charged with 277 mmol of 3-(2-bromophenyl)-propylpropionic acid and 200 ml of thionyl chloride, and the mixture was heated under reflux for 2 hours. Then, the excess thionyl chloride was removed by a single distillation, and the distillation of the residue under reduced pressure gave 77.4 g of a crude product having a boiling point of 130° to 135° C./1 mmHg as a pale brown transparent liquid. This acid chloride was used in the next reaction without further purification Synthesis of 4-bromo-2-n-propyl-1-indanone A 1-liter four-necked round flask equipped with a stirring bar, a Dimroth condenser, a dropping funnel, a thermometer and a NaOH trap was charged with 74.5 g (559 mmol) of anhydrous aluminum chloride and 400 ml of carbon disulfide. To the mixture was added gradually dropwise a solution containing the above-obtained acid chloride dissolved in 100 ml of carbon disulfide while cooling with ice bath. After the addition was completed, the mixture was stirred at 0° C. for 3 hours. Then, the reaction solution was poured onto 600 ml of ice water. The organic phase was separated and the aqueous phase was extracted with 200 ml of ether four times. The combined organic phase was washed four times with 300 ml of a saturated aqueous solution of sodium bicarbonate, followed by drying over anhydrous $MgSO_4$. The solvent was evaporated to give 66.7 g of a brown liquid. This ketone was used in the next reaction without further purification.

Synthesis of 4-bromo-2-n-propyl-1-trimethylsilyloxyindane

A 1-liter four-necked round flask equipped with a stirring bar, a Dimroth condenser, a dropping funnel and a thermometer was charged with 4.96 g (131 mmol) of sodium born hydride and 300 ml of ethanol. To the mixture was added dropwise a solution containing the above-obtained 4-bromo-2-n-propyl-1-indanone dissolved in 200 ml of ethanol while cooling with ice bath. After the addition was completed, the mixture was stirred for 3 hours at room temperature. After the reaction was completed, to the reaction mixture was added 200 ml of ice water and the almost of the methanol was evaporated using an evaporator. The residue was transferred to a separating funnel using 300 ml of ether. After the organic phase was separated, the aqueous phase was extracted with 200 ml of ether three times. The combined organic phase was dried over anhydrous $MgSO_4$. Then, the solvent was evaporated to give 66.50 g of a yellow-white powder.

Then, the above-obtained yellow-white powder, 200 ml of ether and 47 ml (337 mmol) of triethylamine were charged into a 1-liter four-necked round flask. To the mixture was added a solution containing 39 ml (307 mmol) of trimethylsilyl chloride dissolved in 50 ml of ether while cooling with ice bath. After the reaction mixture was stirred for 7 hours, the reaction mixture was poured onto 400 ml of a saturated aqueous solution of sodium bicarbonate, and the organic phase was separated. Then, the aqueous phase was extracted with 200 ml of ether three times. The combined organic phase was washed with 400 ml of a saturated NaCl aq., followed by dried over anhydrous $MgSO_4$. Then, the solvent was evaporated to give a yellow-brown liquid. The liquid was distilled under reduced pressure to give 76.00 g of the desired product as a pale yellow-white transparent liquid having a boiling point of 120° to 125° C./2 mmHg. The total yield of this liquid was 81% from the 3-(2-bromophenyl)-2-n-propylpropionic acid.

Synthesis of 2-n-propyl-4-(1-naphthyl)indene

A 300-ml four-necked round flask equipped with a stirring bar, a dropping funnel and a thermometer was charged with 10 g (30.5 mmol) of 4-bromo-2-n-propyl-1-trimethylsilyloxyindane, 50 ml of dry ether and 112 mg (0.153 mmol) of $PdCl_2$ (dppf). To the mixture was added gradually dropwise 85 ml (61 mmol) of an ether/benzene solution containing 0.72M 1-naphthyl magnesium bromide at room temperature. Then, the temperature in the flask was elevated to 48° C. and the mixture was stirred under reflux for 4 hours. Thereafter, the reaction product was poured onto 300 ml of a saturated aqueous solution of ammonium chloride, which was then extracted with 200 ml of ether four times. The organic phase was washed with a saturated NaCl aq., followed by dried over anhydrous $MgSO_4$. The solvent was evaporated to give 17.83 g of a yellow-brown semisolid.

The above-obtained yellow-brown semisolid and 50 ml of ether were charged into a 300-ml three-necked round flask. To the mixture was added dropwise 60 ml of an aqueous solution of 5N hydrochloric acid at room temperature, and vigorously stirred. After 2 hours, the mixture was transferred to a separating funnel and extracted with 50 ml of ether three times. The combined organic phase was washed with 100 ml of a saturated aqueous solution of sodium bicarbonate two times, followed by dried over anhydrous $MgSO_4$. The solvent was evaporated to give a brown semisolid. The semisolid thus obtained was purified with silica gel chromatography (eluting with hexane/ethyl acetate=50/1 to 50/5) to give 8.40 g of a yellow-white powder.

Then, the above-obtained yellow-white powder, 80 ml of anhydrous methylene chloride, 11.3 ml (81 mmol) of triethylamine and 165 ml (1.35 mmol) of 4-dimethylaminopyridine were charged into a 200-ml four-necked round flask. To the mixture was added gradually dropwise a solution containing 4.2 ml (5.43 mmol) of methanesulfonyl chloride dissolved in 20 ml of anhydrous methylene chloride while cooling with ice bath. After the addition was completed, the temperature was elevated to room temperature, and the mixture was stirred overnight. Then, the reaction product was poured onto 100 ml of ice water, which was then extracted with 100 ml of methylene chloride three times. The combined organic phase was washed with 100 ml of a saturated aqueous solution of sodium bicarbonate three times, followed by dried over anhydrous MgSO$_4$. The solvent was evaporated to give a brown liquid. The thus obtained brown liquid was chromatographed on silica gel (200 g of silica gel, hexane/ethyl acetate=50/1) to give 6.51 g of the desired product as a white solid (yield: 75%).

NMR (CDCl$_3$, 90 MHz): δ=0.91 (t, J=7.0 Hz, 3H, CH$_3$); 1.53 (m, 2H); 2.40 (t, J=7.0 Hz, 2H); 3.04, 3.41 (each s, total 2H); 6.60 (s, 1H) 7.00–8.00 (m, 10H)

Synthesis of dimethylsilyl-bis{1-(2-n-propyl-4-(1-naphthyl)indene

A 200-ml four-necked round flask equipped with a stirring bar, a Dimroth condenser, a dropping funnel and a thermometer was charged with 6.27 g (22.0 mmol) of 2-n-propyl-4-(1-naphthyl)indene, 120 ml of dry ether and 60 mg of copper cyanide. To the mixture was added dropwise 15 ml (24.5 mmol) of a hexane solution containing 1.63M n-butyl lithium while cooling with ice bath. After the addition was completed, the mixture was stirred under reflux for 30 minutes. Then, to the resulting mixture was added dropwise a solution containing 1.5 ml (12.4 mmol) of dimethyldichlorosilane dissolved in 5 ml of dry ether while cooling with ice bath. After the addition was completed, the mixture was stirred overnight at room temperature. Then, the reaction mixture was poured onto a saturated aqueous solution of ammonium chloride. After filtration, the organic phase of the filtrate was separated, and the aqueous phase was extracted with 50 ml of ether two times. The combined organic phase was washed with 100 ml of a saturated NaCl aq. two times, followed by dried over anhydrous MgSO$_4$. The solvent was evaporated to give a yellow oil. The yellow oil thus obtained was then purified with silica gel chromatography (200 g of silica gel, hexane/ethyl acetate=50/1) to give 5.80 g of the desired product as a yellow-white powder (yield: 84%).

NMR (CDCl$_3$, 90 MHz): δ=−0.20, −0.17 (each s, total 6H, Si—CH$_3$); 0.64–2.70 (m, 14H); 3.80–4.10 (m, 2H, —CH—Si); 6.25, 6.34 (each 6d, total 2H); 7.20–8.20 (m, 20H)

Synthesis of rac-dimethylsilyl-bis{1-(2-n-propyl-4-(1-naphthyl)indenyl)}zirconium dichloride A 100-ml four-necked round flask equipped with a stirring bar, a condenser, a dropping funnel and a thermometer was charged with 2.5 g (4.00 mmol) of dimethylsilyl-bis{1-(2-n-propyl-4-(1-naphthyl)indene}and 50 ml of dry ether. To the mixture was added dropwise 5.15 ml (8.40 mmol) of a hexane solution containing 1.63M n-butyl lithium in a water bath. After the addition was completed, the mixture was stirred overnight at room temperature. Thereafter, to the resulting mixture was added 1.00 g (4.29 mmol) of ZrCl$_4$ at −78° C. After the addition was completed, the mixture was allowed to stand overnight. The resultant orange color reaction slurry was filtered and the filtered material was washed with 40 ml of dry ether and 40 ml of dry methylene chloride. The mixture was filtered and the filtrate was concentrated to about ⅓ of a total volume of the filtrate. The precipitate was dissolved in 10 ml of methylene chloride, which was then crystallized from 20 ml of dry ether. The precipitate was filtered and washed with 5 ml of dry ether, followed by dried under reduced pressure to give 0.09 g of the desired product as the yellow powder (yield: 3%).

NMR (CDCl$_3$, 90 MHz): δ=0.80 (t, J=7.4 Hz, 6H, CH$_3$); 1.36 (s, 6H, Si—CH$_3$); 1.10–3.00 (m, 8H); 6.53 (s, 2H, 3-H-Ind); 7.00–8.00 (m, 20H)

Example 11

Synthesis of rac-dimethylsilyl-bis{1-(2-n-propyl-4-(9-phenanthryl)indenyl)}zirconium dichloride Synthesis of 2-n-propyl-4-(9-phenanthryl)indene A 300-ml four-necked round flask equipped with a stirring bar, a dropping funnel and a thermometer was charged with 10 g (30.5 mmol) of the 4-bromo-2-n-propyl-1-trimethylsilyloxyindane synthesized in Example 10, 50 ml of dry ether and 112 mg (0.153 mmol) of PdCl$_2$ (dppf). To the mixture was added dropwise 42 ml (61 mmol) of an ether/benzene solution containing 1.45M 9-phenantolyl magnesium bromide at room temperature while stirring. Then, the temperature in the flask was elevated to 42° C. and the mixture was stirred under reflux for 10 hours. Thereafter, the reaction mixture was poured onto 300 ml of a saturated aqueous solution of ammonium chloride, which was then extracted with 200 ml of ether four times. The combined organic phase was washed with a saturated NaCl aq. and dried over anhydrous MgSO$_4$. The solvent was evaporated to give 20.3 g of a brown liquid.

The above-obtained brown liquid and 50 ml of ether were charged into a 300-ml four-necked round flask. To the flask was added dropwise 60 ml of an aqueous solution of 5N hydrochloric acid at room temperature, and the mixture was vigorously stirred for 6.5 hours. The resulting mixture was transferred to a separating funnel, and washed with 50 ml of ether four times. The combined organic phase was washed with 100 ml of a saturated aqueous solution of sodium bicarbonate two times, followed by dried over anhydrous MgSO$_4$. The solvent was evaporated to give a brown semisolid. The brown semisolid thus obtained was purified with silica gel chromatography to give 10.75 g of a yellow powder.

Then, the above-obtained yellow powder, 80 ml of anhydrous methylene chloride, 12.8 ml (92.0 mmol) of triethylamine and 187 ml (1.53 mmol) of 4-dimethylaminopyridine were charged into a 200-ml four-necked round flask. To the mixture was added dropwise a solution containing 4.72 ml (61.0 mmol) of methanesulfonyl chloride dissolved in 20 ml of anhydrous methylene chloride while cooling with ice bath. After the addition was completed, the temperature was elevated to room temperature and the mixture was stirred for four hours. Thereafter, the reaction product was poured onto 100 ml of ice water, which was then extracted with 100 ml of methylene chloride three times. The combined organic phase was washed with 100 ml of a saturated aqueous solution of sodium bicarbonate three times, followed by dried over anhydrous MgSO$_4$. The solvent was evaporated to give a red-brown semisolid. The red-brown semisolid thus obtained was purified with silica gel chromatography to give 7.20 g of the desired product as a yellow-white powder (yield: 71%).

NMR (CDCl$_3$, 90 MHz): δ=0.92 (t, J=7.0 Hz, 3H, CH$_3$); 1.50 (m, 2H); 2.36 (t, J=7.0 Hz, 2H); 3.02 (bd, 2H); 6.60 (s, 1H); 7.05–9.00 (m, 12H)

Synthesis of dimethylsilyl-bis{1-(2-n-propyl-4-(9-phenanthryl)indene

A 300-ml four-necked round flask equipped with a stirring bar, a Dimroth condenser, a dropping funnel and a thermometer was charged with 6.20 g (18.5 mmol) of 2-n-propyl-4-(9-phenantolyl)indene, 120 ml of dry ether and 50 mg of copper cyanide. To the mixture was added dropwise 12.5 ml (20.4 mmol) of a hexane solution containing 1.63M n-butyl lithium while cooling with ice bath. After the addition was completed, the mixture was stirred under reflux for 1.5 hours. Then, to the resulting mixture was added dropwise a solution containing 1.34 ml (11.1 mmol) of dimethyldichlorosilan dissolved in 10 ml of dry ether. After the addition was completed, the mixture was stirred overnight at room temperature. Then, the reaction mixture was poured onto 200 ml of a saturated aqueous solution of ammonium chloride. After the filtration, the filtrate was extracted with 100 ml of ether three times. The organic phase was washed with 200 ml of a saturated NaCl aq. and dried over anhydrous $MgSO_4$. The solvent was evaporated to give a yellow-white powder. The powder thus obtained was purified with silica gel chromatography to give 3.80 g of the desired product as a yellow-white powder (yield: 54%).

NMR ($CDCl_3$, 90 MHz): δ=−0.17, −0.15 (each s, total 6H, Si—$CH_3$); 0.65–2.75 (m, 14H); 3.86–4.25 (m, 2H, —CH—Si); 6.25, 6.34 (each 6d, 2H); 7.05–9.05 (m, 24H)

Synthesis of rac-dimethylsilyl-bis{1-(2-n-propyl-4-(9-phenanthryl)indennyl)}zirconium dichloride A 200-ml four-necked round flask equipped with a stirring bar, a condenser having beads, a dropping funnel and a thermometer was charged with 2.9 g (4.00 mmol) of dimethylsilyl-bis{1-(2-n-propyl-4-(9-phenantolyl)indene)} and 60 ml of dry ether. To the mixture was added dropwise 5.15 ml (8.40 mmol) of a hexane solution containing 1.63M n-butyl lithium while cooling with ice bath. After the addition was completed, the mixture was stirred overnight at room temperature. Then, to the resulting mixture was added dropwise 1.00 g (4.29 mmol) of $ZrCl_4$ at −78° C. After the addition was completed, the mixture was allowed to warm to room temperature. The resulting orange color reaction mixture was filtered and washed with 100 ml of dry methylene chloride. The filtrate was concentrated to dryness, which was then dissolved in 100 ml of dry methylene chloride. To the solution was added dry ether to give precipitate which was then filtered and washed with 15 ml of dry ether, followed by dried under reduced pressure to give 0.10 g of the desired product as a yellow powder (yield: 2.8%).

NMR ($CDCl_3$, 90 MHz): δ=0.80 (t, J=7.4 Hz, 6H, $CH_3$); 1.39 (s, 6H, Si—$CH_3$); 1.10–3.00 (m, 8H); 6.61 (s, 2H, 3-H-Ind); 7.00–9.10 (m, 24H)

Example 12

Synthesis of rac-dimethylsilyl-bis{1-(2-ethyl-4-(9-phenanthryl)indenyl)}zirconium dichloride Synthesis of 2-ethyl-1-hydroxy-4-(9-phenanthryl) indane A 200-ml three-necked round flask equipped with a stirring bar, a Dimroth condenser, a dropping funnel and a thermometer was charged with 11.54 g (36.8 mmol) of 4-bromo-2-ethyl-1-trimethylsilyloxyindane, 0.135 g (0.184 mmol) of $PdCl_2$ (dppf) and 35 ml of dry ether. To the mixture was added dropwise 51.5 ml (73.7 mmol) of an ether/benzene solution containing 1.4M 9-phenantolyl magnesium bromide at room temperature under a nitrogen atmosphere. After the addition was completed, the temperature in the flask was elevated to 42° C., and the mixture was stirred under reflux for 8 hours. After the reaction was completed, the reaction mixture was cooled to room temperature, and the excess amount of Gringnard reagent was decomposed by gradually adding 100 ml of water. After the addition of 50 ml of ether, organic phase was separated, filtered through Celite, and the filtrate was washed with 100 ml of a saturated NaCl aq., followed by dried over anhydrous $Na_2SO_4$. The solvent was evaporated under reduced pressure to give 25 g of a dark red-brown liquid.

Then, a 200-ml three-necked round flask equipped with a stirring bar, a Dimroth condenser, a dropping funnel and a thermometer was charged with the above-obtained red-brown liquid and 50 ml of tetrahydrofuran. To the mixture was added dropwise 6 ml of an aqueous solution of 12% hydrochloric acid at room temperature under a nitrogen atmosphere. The reaction mixture was stirred for 5 hours. After the reaction was completed, 100 ml of ether was added and the organic phase was separated, washed with 100 ml of a saturated aqueous solution of sodium bicarbonate, and then 100 ml of a saturated aqueous solution of salt three times, followed by dried over anhydrous $Na_2SO_4$. The solvent was evaporated to give a dark red liquid residue. The thus obtained dark red liquid residue was purified with silica gel chromatography (eluting with hexane, and then hexane/ethyl acetate (4/1 parts by volume)) to give 12.33 g of the desired product (mixture of two isomers) as a pasty red-brown liquid (yield: 99%).

FD-MS: 338 ($M^+$)

Synthesis of 2-ethyl-4-(9-phenanthryl)indene

A 300-ml three-necked round flask equipped with a stirring bar, a Dimroth condenser, a dropping funnel and a thermometer was charged with 12.3 g (36.3 mmol) of 2-ethyl-1-hydroxy-4-(9-phenanthryl)indane, 19.7 ml (142 mmol) of triethylamine and 61.5 ml of methylene chloride. To the mixture was gradually dropwise added a solution containing 3.3 ml (42.6 mmol) of methanesulfonyl chloride dissolved in 5 ml of methylene chloride under a nitrogen atmosphere at 0° C. After the addition was completed, the temperature was elevated to room temperature, and the reaction mixture was stirred for additional 4 hours. To the reaction mixture was added 80 ml of a saturated aqueous solution of sodium bicarbonate. The organic phase was separated, and the aqueous phase was extracted with 50 ml of methylene chloride two times. The combined organic phase was washed with water, and then a saturated aqueous solution of sodium chloride, followed by drying over anhydrous $Na_2SO_4$. The solvent was evaporated under reduced pressure. The residue was chromatographed on silica gel (eluting with hexane, and hexane/ethyl acetate (100/3 parts by volume)) to give 9.61 g of the desired product (mixture of two isomers) as a pasty pale yellow-green liquid (yield: 83%).

FD-MS: 320 ($M^+$)

NMR ($CDCl_3$, 90 MHz): δ=0.86–1.44 (m, 3H, $CH_3$); 2.16–2.58 (m, 2H); 3.04, 3.42 (each bs, total 2H); 6.09, 6.55 (each bs, total 1H); 6.95–7.97 (m, 10H); 8.57–8.93 (m, 2H)

Synthesis of dimethylsilyl-bis{1-(2-ethyl-4-(9-phenanthryl)indene)}

A 200-ml three-necked round flask equipped with a stirring bar, a Dimroth condenser, a dropping funnel and a thermometer was charged with 5.3 g (16.5 mmol) of 2-ethyl-4-(9-phenanthryl)indene, 45 mg (0.45 mmol) of copper cyanide and 106 ml of dry ether. To the mixture was added dropwise 11.8 ml (18.2 mmol) of a hexane solution containing 1.54M n-butyl lithium under a nitrogen atmosphere at −10° C. After the addition was completed, the temperature was elevated to room temperature and the mixture was further stirred for 5 hours. Then, to the reaction mixture was added dropwise a solution containing 1.12 ml (9.1 mmol) of dimethyldichlorosilane dissolved in 5 ml of dry ether while cooling with ice bath. After the addition was completed, the temperature was elevated to room temperature, and the mixture was stirred for 15 hours. To the reaction mixture was added 50 ml of a saturated aqueous solution of ammonium chloride. Then, the insoluble substance was filtered through Celite, and the filtrate was separated to an organic phase and an aqueous phase. The aqueous phase was extracted with 50 ml of ether. The combined organic phase was washed with 50 ml of a saturated NaCl aq. three times, and dried over anhydrous $Na_2SO_4$. The solvent was evaporated under reduced pressure to obtain a residue of a pasty pale yellow-brown liquid. The thus obtained residue was separated with silica gel chromatography (eluting with hexane, and hexane/ethyl acetate (1000/7 parts by volume)) to give 3.19 g of the desired product (mixture of sstereoisomers) as a yellow solid (yield: 55%).

| | |
|---|---|
| FD-MS | 697 ($M^+$) |
| NMR ($CDCl_3$, 90 MHz) | δ=−0.18, −0.14(each s, total 6H, Si—$CH_3$); |
| | 0.79–1.41(m, 6H, $CH_3$); |
| | 2.13–2.73(m, 4H); |
| | | |
| | 3.84–4.15(m, 2H, —CH—Si); |
| | 6.21, 6.31(each bs, 2H); |
| | 6.98–8.05(m, 20H); |
| | 8.52–8.93(m, 4H) |

Synthesis of rac-dimethylsilyl-bis{1-(2-ethyl-4-(9-phenanthryl)indenyl)}zirconium dichloride A 100-ml three-necked round flask equipped with a stirring bar, a condenser, a dropping funnel and a thermometer was charged with 0.60 g (0.86 mmol) of dimethylsilyl-bis{1-(2-ethyl-4-(9-phenanthryl)indene)} and 12 ml of dry ether under an argon atmosphere. To the mixture was added dropwise 1.18 ml (1.81 mmol) of a hexane solution containing 1.54M n-butyl lithium at room temperature. After the addition was completed, the mixture was further stirred for 18.5 hours. The pale yellow-orange reaction mixture was cooled to −70° C. Then, to the mixture was added 0.20 g (0.86 mmol) of $ZrCl_4$. After the addition was completed, the mixture was allowed to warm to room temperature overnight. The resulting orange-yellow reaction slurry was filtered, and the residue was washed with 6 ml of dry ether, and then 5 ml of methylene chloride five times. To the resulting product was added 55 ml of methylene chloride, and then the insoluble material was filtered off. The filtrate was concentrated to dryness. The dried product was reslurried in 2 ml of dry ether and dried to obtain 80 mg of a yellow-orange powder. NMR analysis showed that this powder comprises a mixture of rac/meso (91/9). Then, the above-obtained powder was reslurried and washed in 2 ml of methylene chloride and 2 ml of dry ether. Then, the resulting product was dried under reduced pressure to obtain 66 mg of the desired product as a yellow-orange powder (yield: 9%).

NMR ($CDCl_3$, 90 MHz): δ=1.01 (t, J=7.6 Hz, 6H, $CH_3$); 1.37 (s, 6H, Si—$CH_3$); 2.16–2.91 (m, 4H); 6.55 (s, 2H, 3-H-Ind)); 6.78–8.12 (m, 20H); 8.39–8.76 (m, 4H)

Example 13

Synthesis of rac-dimethylsilyl-bis{1-(2-i-butyl-4-(1-naphthyl)indenyl)}zirconium dichloride 2-bromobenzylidene diethylmalonic acid A 500-ml three-necked round flask (Dean & Stark) equipped with a stirring bar, a Dimroth condenser and a thermometer was charged with 74.0 g (400 mmol) of 2-bromobenzaldehyde, 70.48 g (440 mmol) of diethylmaloic acid, 1.6 ml of piperidine, 4.8 ml of acetic acid and 80 ml of benzene. The mixture was subjected to azeotoropic dehydration for 7 hours in an oil bath of 110° C. under a nitrogen atmosphere. After the reaction was completed, the reaction mixture was cooled to room temperature and 300 ml of ether was added, followed by washing with 100 ml of water two times. The organic phase was dried over anhydrous $Na_2SO_4$. The solvent was concentrated under reduced pressure and the concentrate of a orange liquid was distilled under reduced pressure to obtain 117.2 g of the desired product as a yellow liquid (yield: 90%).

bp.: 164°–171° C./0.2 mmHg

NMR ($CDCl_3$, 90 MHz): δ=1.17 (t, J=7.0 Hz, 3H, $CH_3$); 1.34 (t, J=7.0 Hz, 3H, $CH_3$); 4.22 (q, J=7.0 Hz, 2H, —O—$CH_2$—); 4.32 (q, J=7.0 Hz, 2H, —O—$CH_2$—) 7.06–7.80 (m, 3H); 7.97 (s, 1H);

IR (Neat): 1725 $cm^{-1}$($v_{c=o}$);

mp.: 43.6°–45.6° C.

Synthesis of 2-bromobenzyl diethylmalonic acid

A 500-ml three-necked round flask equipped with a stirrer, a dropping funnel and thermometer was charged with 13.64 g (360.8 mmol) of sodium borohydride and 280 ml of ethanol. To the mixture was added a solid of 2-bromobenzylidene diethylmalonic acid in portions under a nitrogen atmosphere while cooling with ice bath. After the addition was completed, the mixture was further stirred for 1 hour. Then, the resulting white slurry was filtered, and the residue was washed with 50 ml of ethanol. The combined filtrate was concentrated under reduced pressure, which was then extracted with 200 ml of water and 200 ml of ether. The organic phase was separated, and the aqueous phase was further extracted with 200 ml of ether. The combined organic phase was washed with 200 ml of a saturated NaCl aq. two times, followed by drying over anhydrous $Na_2SO_4$. The solvent was evaporated under reduced pressure. The residue was separated and purified with silica gel chromatography (eluting with hexane/ethyl acetate (6/1 parts by volume)) to obtain 55.4 g of the desired product as a colorless liquid (yield: 47%).

NMR ($CDCl_3$, 90 MHz): δ=1.21 (t, J=7.1 Hz, 6H, $CH_3$); 3.33 (d, J=7.6 Hz, 2H); 3.84 (dd, J=7.6 Hz, 7.6 Hz, 1H); 4.13 (q, J=7.1 Hz, 4H, —O—$CH_2$—) 6.87–7.36 (m, 3H); 7.51 (dd, J=2.3 Hz, 7.6 Hz, 1H);

IR (Neat): 1730 $cm^{-1}$($v_{c=o}$)

Synthesis of 3-(2-bromophenyl)-2-i-butylpropionic acid

A 1-liter four-necked round flask equipped with a stirrer, a Dimroth condenser, a dropping funnel and a thermometer was charged with 20.45 g (182.3 mmol) of potassium-t-butoxide, 180 ml of toluene and 25 ml of N-methylpyrrolidone. To the mixture was added a solution containing 50.0 g (151.9 mmol) of 2-bromobenzyl diethylmalonic acid dissolved in 40 ml of toluene at room temperature under a nitrogen atmosphere. After the addition was completed, the temperature in the flask was elevated to 60° C. and the reaction mixture was stirred for 1 hour. Then, to the resulting mixture was added a solution containing 24.97 g (182.3 mmol) of i-butylbromide dissolved in 30 ml of toluene at the same temperature. After the addition was completed, the temperature was elevated and the mixture was stirred under reflux for 18 hours. The reaction mixture was poured onto 150 ml of a saturated aqueous solution of sodium chloride, and the mixture was adjusted to pH 3 with addition of 12% hydrochloric acid. The organic phase was separated, and the aqueous phase was extracted with 100 ml of ether two times. The combined organic phase was washed with 200 ml of a saturated aqueous solution of sodium bicarbonate, and then 150 ml of a saturated aqueous solution of sodium chloride, followed by drying over anhydrous $Na_2SO_4$. The solvent was concentrated under reduced pressure to obtain 64 g of the concentrate as an orange liquid.

Then, a 1-liter four-necked round flask equipped with a stirrer, a Dimroth condenser, a dropping funnel and a thermometer was charged with 100 g (1.52 mol) of potassium hydroxide and 300 ml of an aqueous methanol solution (methanol/water=4/1 (v/v)). To the mixture was added dropwise the above-obtained concentrate at room temperature under a nitrogen atmosphere. After the addition was completed, the temperature was elevated and the mixture was stirred under reflux for 7 hours. After the reaction was completed, the methanol was evaporated under reduced pressure. The residue was dissolved in water and adjusted to pH 3 with addition of dilute sulfuric acid. The precipitate was filtered and washed with 150 ml of ether. The combined filtrate was separated to an oil phase and an aqueous phase. The aqueous phase was extracted with 100 ml of ether two times. The combined organic phase was washed with 100 ml of a saturated aqueous solution of sodium chloride, followed by drying over anhydrous $Na_2SO_4$. The solvent was concentrated under reduced pressure to obtain 49.7 g of an orange-brown pasty liquid. Then, the above-obtained orange-brown pasty liquid was charged into a 300-ml flask equipped with a stirring bar and a Dimroth condenser, and heated to 180° C. and stirred for 1.5 hours under a nitrogen atmosphere. 42.1 g of the desired product was obtained as a dark red pasty liquid (yield: 97%). This carboxylic acid was used in the next reaction without further purification.

NMR ($CDCl_3$, 90 MHz): $\delta$=0.90 (d, J=6.4 Hz, 3H, $CH_3$); 0.93 (d, J=6.4 Hz, 3H, $CH_3$); 1 07–1.89 (m, 3H); 2.57–3.09 (m, 3H); 6.72–7.30 (m, 4H); 7.51 (dd, J=2.0 Hz, 7.1 Hz, 1H);

Synthesis of 3-(2-bromophenyl)-2-i-butylpropionic acid chloride

A 200-ml four-necked round flask equipped with a stirring bar, a Dimroth condenser, a hermometer and a NaOH trap was charged with 42.1 g of 3-(2-bromophenyl)-2-i-butylpropinonic acid and 60 ml of thionyl chloride. The mixture was stirred under reflux for 1.5 hour under a nitrogen atmosphere. After the reaction was completed, the unreacted thionyl chloride was evaporated under reduced pressure. The residue was distilled under reduced pressure to obtain 40.3 g of the desired product as a pale orange liquid (yield: 90%).

bp.: 130°–132° C./0.1–0.2 mmHg

NMR ($CDCl_3$, 90 MHz): $\delta$=0.90 (d, J=6.4 Hz, 3H, $CH_3$); 0.96 (d, J=6.4 Hz, 3H, $CH_3$); 1.13–2.06 (m, 3H); 2.71–3.53 (m, 3H): 6.88–7.40 (m, 3H); 7.50 (d, J=6.9 Hz, 1H);

IR (Neat): 1780 $cm^{-1}$($v_{c=o}$)

Synthesis of 4-bromo-4-i-butyl-1-indanone

A 500-ml four-necked round flask equipped with a stirrer, a Dimroth condenser, a dropping funnel, a thermometer and a NaOH trap was charged with 20.33 g (152.5 mmol) of anhydrous aluminum chloride and 70 ml of carbon disulfide. To the mixture was added dropwise a solution containing 40.2 g (132.6 mmol) of the above-obtained 3-(2-bromophenyl)-2-i-butylpropionic acid chloride dissolved in 50 ml of carbon disulfide under a nitrogen atmosphere while cooling with ice bath. After the addition was completed, the temperature in the flask was elevated to room temperature, and the mixture was stirred for 1 hour. Then, the reaction mixture was quenched by pouring onto 200 ml of ice water, which was then extracted with 100 ml of ether three times. The combined organic phase was washed with 100 ml of a saturated aqueous solution of sodium bicarbonate, and then 100 ml of a saturated NaCl aq., followed by dried over anhydrous $Na_2SO_4$. The solvent was evaporated under reduced pressure to give 37.4 g of the desired product as an orange liquid. This ketone was used in the next reaction without further purification.

NMR ($CDCl_3$, 90 MHz): $\delta$=0.99 (t, J=6.4 Hz, 6H, $CH_3$); 1.02–1.55 (m, 1H); 1.59–2.12 (m, 2H); 2.53–2.94 (m, 2H): 3.02–3.62 (m, 1H); 7.24 (t, J=7.6 Hz, 1H); 7.66 (d, J=7.6 Hz, 1H); 7.74 (d, J=7.6 Hz, 1H);

IR (Neat): 1718 $cm^{-1}$($v_{c=o}$)

Synthesis of 4-bromo-2-i-butyl-1-hydroxyindane

A 300-ml three-necked round flask equipped with a stirring bar, a Dimroth condenser, a dropping funnel and a thermometer was charged with 2.51 g (66.3 mmol) of sodium boron hydride and 85 ml of ethanol. To the mixture was added dropwise a solution containing 37.0 g (132.6 mmol) of the above-obtained 4-bromo-2-i-butyl-1-indanone dissolved in 55 ml of ethanol at room temperature under a nitrogen atmosphere. After the addition was completed, the mixture was further stirred for 16 hours. Then, the reaction mixture was concentrated under reduced pressure, which was then extracted with 150 ml of water and 150 ml of ether. The organic phase was separated, and the aqueous phase was further extracted with 100 ml of ether. The combined organic phase was washed with 100 ml of a saturated NaCl aq. two times, followed by dried over anhydrous $Na_2SO_4$. The solvent was evaporated under reduced pressure to obtain 34.4 g of the desired product (mixture of two isomers) as a pale yellow solid (yield: 96%). This alcohol was used in the next reaction without further purification.

| NMR ($CDCl_3$, 90 MHz) | $\delta$=0.76–1.23(m, 6H, $CH_3$); 1.25–2.01(m, 3H); 2.05–3.36(m, 3H); 4.80, 5.03(each bs, total 1H, \|  —CH—O—); 6.89–7.57(m, 3H); |
|---|---|
| IR (KBr disk) | 3232 $cm^{-1}$ ($v_{OH}$) |

Synthesis of 4-bromo-2-i-butyl-1-trimethylsilyloxyindane

A 300-ml three-necked round flask equipped with a stirring bar, a Dimroth condenser, a dropping funnel and a thermometer was charged with 34.4 g (127.8 mmol) of 4-bromo-2-i-butyl-1-hydoxyindane, 23.1 ml (166.2 mmol) of triethylamine and 118 ml of methylene chloride. To the mixture was added dropwise 20 ml of a methylene chloride solution containing 19.45 ml (153.4 mmol) of trimethylsilyl chloride under a nitrogen atmosphere while cooling with ice bath. After the addition was completed, the temperature was elevated to room temperature, and the mixture was further stirred for 1.5 hours. The reaction mixture was poured onto a mixture of 200 ml of ice water and 20 ml of a saturated aqueous solution of sodium bicarbonate. Then, the organic phase was separated, and the aqueous phase was further extracted with 50 ml of methylene chloride two times. The combined organic phase was washed with 100 ml of a saturated NaCl aq., followed by dried over anhydrous Na$_2$SO$_4$. The solvent was evaporated under reduced pressure. The residue was distilled under reduced pressure to obtain 41.8 g of the desired product (mixture of two isomers) as a pale yellow liquid (yield: 96%).

| bp. | 141–146° C./0.1–0.2. mmHg |
|---|---|
| NMR (CDCl$_3$, 90 MHz) | δ=0.15–0.24(each s, total 9H, Si—CH$_3$); 0.76–1.10(m, 6H, CH$_3$); 1.20–1.84(m, 3H); 2.12–3.26(m, 3H); 4.77, 5.06(each bd, each<br>\|<br>J=6.4Hz, total 1H, —CH—O—); 6.88–7.44(m, 3H) |

Synthesis of 2-i-butyl-1-hydroxy-4-(1-naphtyl)indene

A 200-ml three-necked round flask equipped with a stirring bar, a Dimroth condenser, a dropping funnel and a thermometer was charged with 5.0 g (14.65 mmol) of 4-bromo-2-i-n-butyl-1-trimethylsilyloxyindane, 53.6 mg (0.073 mmol) of PdCl$_2$ (dppf) and 15 ml of dry ether. To the mixture was added dropwise 40.7 ml (29.3 mmol) of an ether/benzene solution containing 0.72M 1-naphthylmagnesium bromide at room temperature under a nitrogen atmosphere. After the addition was completed, the temperature in the flask was elevated to 50° to 51° C., and the mixture was stirred under reflux for 18 hours. After the reaction was completed, the temperature was cooled to room temperature. Thereafter, the reaction mixture was added to a mixture of 100 ml of a saturated aqueous solution of ammonium chloride and ice so as to decompose an excess amount of Grignard reagent. The resultant mixture was extracted with 50 ml of ether two times. The combined organic phase was washed with a saturated aqueous solution of sodium bicarbonate, and then a saturated NaCl aq., followed by dried over anhydrous Na$_2$SO$_4$. The solvent was evaporated to obtain 12.1 g of a pasty liquid.

Then, the above-obtained pasty liquid was diluted with 24.2 ml of tetrahydrofuran and 7 ml of 12% hydrochloric acid was added. The mixture was stirred at room temperature for 3 hours. After the reaction was completed, the reaction mixture was added to 50 ml of a saturated aqueous solution of sodium bicarbonate, which was then extracted with 50 ml of ether two times. The combined organic phase was washed with a saturated aqueous solution of sodium bicarbonate, and then a saturated NaCl aq., followed by dried over anhydrous Na$_2$SO$_4$. The solvent was evaporated under reduced pressure. The residue was separated and purified with silica gel chromatography (eluting with hexane/ethyl acetate (20/1 parts by volume)) to obtain 4.54 g of the desired product (mixture of two kinds of isomers) as a brown pasty liquid (yield: 98%).

| NMR (CDCl$_3$, 90 MHz) | δ=0.71–1.07(m, 6H); 1.13–2.91(m, 7H); 4.88, 5.07(each bs, total 1H,<br>\|<br>—CH—O—); 7.12–8.01(m, 10H); |
|---|---|
| IR (neat) | 3328 cm$^{-1}$ (ν$_{o—o}$) |

Synthesis of 2-i-butyl-4-(1-naphthyl)indene

A 200-ml three-necked round flask equipped with a stirring bar, a Dimroth condenser, a dropping funnel and a thermometer was charged with 4.54 g (14.4 mmol) of 2-i-butyl-1-hydroxy-4-(1-naphthyl)indene, 5.13 g (50.8 mmol) of triethylamine, 0.10 g (0.82 mmol) of 4-dimethylaminopyridine and 57.7 ml of methylene chloride. To the mixture was added dropwise a solution containing 3.87 ml (33.8 mmol) of methanesulfonyl chloride dissolved in 7.7 ml of methylene chloride under a nitrogen atmosphere while cooling with ice bath. After the addition was completed, the temperature was elevated to room temperature and the mixture was further stirred for 3 hours. The reaction mixture was poured onto 100 ml of water. Thereafter, the organic phase was separated, and the aqueous phase was extracted with 50 ml of methylene chloride. The extracted organic phases were combined and washed with a saturated NaCl aq., followed by dried over anhydrous Na$_2$SO$_4$. The solvent was evaporated under reduced pressure. The residue was separated and purified with silica gel chromatography (eluting with hexane/ethyl acetate (20/1 parts by volume)) to obtain 3.98 g of the desired product (mixture of two isomers) as a pale yellow pasty liquid (yield: 93%).

NMR (CDCl$_3$, 90 MHz): δ=0.86 (d, J=6.4 Hz, 6H, CH$_3$); 1.13–1.99 (m, 1H); 2.24 (d, J=6.4 Hz, 2H); 3.01, 3.40 (each s, total 2H): 6.07, 6.55 (each s, total 1H); 6.92–7.98 (m, 10H)

Synthesis of dimethylsilyl-bis [1-(2-i-butyl-4-(1-naphthyl)indene

A 100-ml three-necked flask equipped with a stirring bar, a Dimroth condenser, a dropping funnel and a thermometer was charged with 2.37 g (7.95 mmol) of 2-i-butyl-4-(1-naphthyl)indene, 28 mg (0.22 mmol) of copper thiocyanate and 24 ml of absolute ether. To the mixture was added dropwise 5.54 ml (8.75 mmol) of a hexane solution containing 1.58M n-butyl lithium at room temperature under a nitrogen atmosphere. After the addition was completed, the mixture was further stirred for 15 hours. Then, to the reaction mixture was added dropwise a solution containing 0.53 ml (4.37 mmol) of dimethyldichlorosilane dissolved in 1.6 ml of dry ether. After the addition was completed, the mixture was further stirred for 27.5 hours at room temperature. The reaction mixture was filtered with Celite, and the filtrate was separated to an organic phase and an aqueous phase by addition of 30 ml of water. The organic phase was separated, and the aqueous phase was extracted with 30 ml of ether. The combined organic phase was washed with a saturated NaCl aq., followed by dried over anhydrous Na$_2$SO$_4$. The solvent was evaporated under reduced pressure to obtain a yellow pasty liquid residue. The thus obtained yellow pasty liquid residue was separated and purified with silica gel chromatography (eluting with hexane/ethyl ether (160/1 parts by volume)) to obtain 1.85 g of the desired product (mixture of two isomers) as a pale yellow solid (yield: 71%).

| FD-MS | 653 (M⁺) |
|---|---|
| NMR (CDCl$_3$, 90 MHz) | $\delta$=−0.37 to −0.08(m, 6H, Si−CH$_3$); |
| | 0.59–1.10(m, 12H, CH$_3$); |
| | 1.19–2.06(m, 2H); |
| | 2.12–2.57(m, 4H); |
| | 3.86, 3.95(each bs, total 2H, —CH—Si); |
| | 6.17, 6.26(each bs, total 2H); |
| | 6.92–8.04(m, 20H) |

Synthesis of rac-dimethylsilyl-bis{1-(2-i-butyl-4-(1-naphtyl)indenyl)}zirconium dichloride A 50-ml three-necked round flask equipped with a stirring bar, a condenser, a dropping funnel and thermometer was charged with 1.0 g (1.53 mmol) of dimethylsilyl-bis{1-(2-i-butyl-4-(1-naphthyl)indene)} and 20 ml of dry ether. To the mixture was added dropwise 2.09 ml (3.22 mmol) of a hexane solution containing 1.54M n-butyl lithium at room temperature. After the addition was completed, the mixture was further stirred for 15 hours. The resulting clear red reaction liquid was cooled to −68° C. To the solution was added 0.36 g (1.53 mmol) of ZrCl$_4$. After the addition was completed, the mixture was allowed to warm to room temperature overnight under stirring. The resulting orange-yellow reaction slurry was filtered and washed with dry ether two times. To the residue was added 25 ml of methylene chloride and the insoluble material was filtered off. The filtrate was concentrated to dryness at room temperature. The resulting orange-yellow dried material was dissolved in 8 ml of methylene chloride, and the solution was concentrated to about ½ of the total amount of the solution. To the solution was added 1 ml of dry ether, to give the precipitates which were filtered, and washed with 1 ml of dry ether. The resulting solid was dried under reduced pressure to obtain 140 mg of an orange-yellow powder. NMR analysis showed that this powder comprises a mixture of rac/meso (88/12). Then, the above-obtained powder was dissolved in 3 ml of methylene chloride. To the solution was added 6 ml of dry ether, to give the precipitates which were filtered, and washed with 0.5 ml of dry ether, followed by dried under reduced pressure to obtain 77 mg of the desired product as a yellow-orange powder (yield: 6%).

FD-MS: 812 (M⁺)

NMR (CDCl$_3$, 90 MHz): $\delta$=0.71 (d, J=6.4 Hz, 6H, CH$_3$); 0.86 (d, J=6.4 Hz, 6H, CH$_3$); 1.36 (s, 6H, Si—CH$_3$); 1.78–2.22 (m, 2H): 2.51–2.87 (m, 4H); 6.41 (s, 2H, 3-H-Ind); 6.86–8.02 (m, 20H)

Example 14

The polymerization was carried out in the same manner as in Example 2 except that the rac-dimethylsilyl-bis{1-(2-ethyl-4-(phenantolyl)indenyl)}zirconium chloride was used in place of the rac-dimethylsilyl-bis{1-(2-ethyl-4-phenylindenyl)}zirconium dichloride as a transition metal compound catalyst component, and the flow rate of hydrogen was changed to 3 liters/hr.

The amount of the thus obtained polymer was 23.4 g and the polymerization activity was 12.0 kg-PP/mmol-Zr.hr. The intrinsic viscosity [η] was 2.92 dl/g, and Mw/Mn was 2.22. In the polymer, the triad tacticity was 99.7%, the proportion of the inversely inserted units based on the 2,1-insertion of the propylene monomer was 0.14%, and the proportion of the inversely inserted units based on the 1,3-insertion of the propylene monomer was less than the detectable lower limit (less than 0.03%).

The results are shown in Table 1 (I) and (II).

Example 15

The polymerization was carried out in the same manner as in Example 2 except that the rac-dimethylsilyl-bis{1-(2-butyl-4-(1-naphthyl)indenyl)}zirconium dichloride was used in place of the rac-dimethylsilyl-bis{1-(2-ethyl-4-phenylindenyl)}zirconium dichloride as a transition metal compound catalyst component, and the flow rate of hydrogen was changed to 3 liters/hr.

The amount of the thus obtained polymer was 24.6 g and the polymerization activity was 12.6 kg-PP/mmol-Zr.hr. The intrinsic viscosity [η] was 3.05 dl/g, and Mw/Mn was 2.10. In the polymer, the triad tacticity was 99.2%, the proportion of the inversely inserted units based on the 2,1-insertion of the propylene monomer was 0.19%, and the proportion of the inversely inserted units based on the 1,3-insertion of the propylene monomer was less than the detectable lower limit (less than 0.03%).

The results are shown in Table 1 (i) and (II).

Example 16

The polymerization was carried out in the same manner as in Example 2 except that the rac-dimethylsilyl-bis{1-(2-n-propyl-4-(1-naphthyl)indenyl)}zirconium dichloride was used in place of the rac-dimethylsilyl-bis{1-(2-ethyl-4-phenylindenyl)}zirconium dichloride as a transition metal compound catalyst component, and the flow rate of hydrogen was changed to 3 liters/hr.

The amount of the thus obtained polymer was 19.9 g and the polymerization activity was 10.2 kg-PP/mmol-Zr.hr. The intrinsic viscosity [η] was 3.13 dl/g, and Mw/Mn was 2.19. In the polymer, the triad tacticity was 99.5%, the proportion of the inversely inserted units based on the 2,1-insertion of the propylene monomer was 0.19%, and the proportion of the inversely inserted units based on the 1,3-insertion of the propylene monomer was less than the detectable lower limit (less than 0.03%).

The results are shown in Table 1 (I) and (II).

Example 17

The polymerization was carried out in the same manner as in Example 2 except that the rac-dimethylsilyl-bis{1-(2-n-propyl-4-(9-phenanthryl)indenyl)}zirconium dichloride was used in place of the rac-dimethylsilyl-bis{1-(2-ethyl-4-phenylindenyl)}zirconium dichloride as a transition metal compound catalyst component, and the flow rate of hydrogen was changed to 3 liters/hr.

The amount of the thus obtained polymer was 14.5 g and the polymerization activity was 7.4 kg-PP/mmol-Zr.hr. The intrinsic viscosity [η] was 3.47 dl/g, and Mw/Mn was 2.15. In the polymer, the triad tacticity was 99.7%, the proportion of the inversely inserted units based on the 2,1-insertion of the propylene monomer was 0.16%, and the proportion of the inversely inserted units based on the 1,3-insertion of the propylene monomer was less than the detectable lower limit (less than 0.03%).

The results are shown in Table 1 (I) and (II).

Example 18

A 2-liter autoclave throughly purged with nitrogen was charged with 920 ml of hexane and 50 g of 1-butene. Then, to the autoclave was added 1 mmol of triisobutylaluminum. After elevating the temperature of the reaction system to 70° C., propylene was fed to the system to a total pressure of 7 kg/cm$^2$-G. To the autoclave were added 0.28 mmol of methylaluminoxane and 7×10$^{-4}$ mmol (in terms of Zr atom) of rac-dimethylsilyl-bis{1-(2-ethyl-4-phenyl-indenyl)}zirconium dichloride to polymerize the monomers for 30 minutes while propylene was continuously fed to keep the total pressure of 7 kg//cm$^2$-G. After the polymerization, the autoclave was released, the resulting polymer was recovered in a large amount of methanol, and dried at 110° C. for 12 hours under reduced pressure.

The amount of the polymer obtained was 52.1 g. The polymerization activity was 149 kg-polymer/mmolZr.hr. The polymer had a 1-butene content of 20.2 mol %, an intrinsic viscosity [η] of 1.90 dl/g, Mw/Mn of 2.05 and a melting point of 101.5° C.

The results are shown in Table 1 (I) and (II).

Example 19

A 500-ml gas through type glass reactor throughly purged with nitrogen was charged with 250 ml of toluene and 9.4 ml of 1-octene, followed by elevating the temperature of the reactor to 50° C. The system was sufficiently saturated by feeding propylene at a flow rate of 250 liters/hr. Then, to the autoclave were added 0.1 mmol of triisobutylaluminum, 1.1 mmol of methylaluminoxane and 0.002 mmol (in terms of Zr atom) of rac-dimethylsilylbis{1-(2-ethyl-4-phenylindenyl)}zirconium dichloride to polymerize the monomers for 30 minutes while propylene was continuously fed at a flow rate of 250 liters/hr to keep the temperature in the system of 50° C. The polymerization was stopped by the addition of a small amount of methanol. The polymer solution was added to 2 liters of methanol containing a small amount of hydrochloric acid to precipitate a polymer. The precipitated polymer was recovered and dried under reduced pressure at 110° C. for 12 hours.

The amount of the polymer obtained was 5.4 g. The polymerization activity was 5.4 kg-polymer/mmolZr.hr. The polymer had a 1-octene content of 6.7 mol %, an intrinsic viscosity [η] of 1.44 dl/g, Mw/Mn of 2.41 and a melting point of 131° C.

The results are shown in Table 1 (I) and (II).

Example 20

A 200-ml reactor equipped with stirring blade throughly purged with nitrogen was charged with 80 liters of hexane, 80 mmol of triisobutylaluminum, 0.25 liter of hydrogen, 9 kg of ethylene and 0.3 kg of propylene, followed by elevating the temperature of the reactor to 70° C. Then, to the reactor were added 18 mmol of methylaluminoxane and 0.06 mmol (in terms of Zr atom) of rac-dimethylsilyl-bis{1-(2-methyl-4-phenylindenyl)}zirconium dichloride to polymerize at 70° C. for 30 minutes. During the polymerization, 13.7 kg of propylene and 0.5 kg of ethylene were respectively fed to the reactor. After the polymerization, the autoclave was released, the resulting polymer was recovered in a large amount of methanol, and dried at 80° C. for 10 hours under reduced pressure.

The amount of the polymer obtained was 7.0 kg. The polymerization activity was 117 kg-polymer/mmolZr.hr. The polymer had an ethylene content of 4.7 mol % and an intrinsic viscosity [B] of 2.7 dl/g. In the polymer, the triad tacticity of the propylene unit chain consisting of head-to-tail bonds was 97.5%, the proportion of the inversely inserted units based on the 2,1-insertion of the propylene monomer was 0.22%, and the proportion of the inversely inserted units based on the 1,3-insertion of the propylene monomer was not more than 0.05%.

The results are shown in Table 1 (I) and (II).

The film of the copolymer had a heat seal-starting temperature of 120° C. and a heat seal-starting temperature after heat treatment of 123° C.

The results are shown in Table 2.

Example 21

A 2-liter autoclave throughly purged with nitrogen was charged with 900 ml of hexane. Then, to the autoclave was added 1 mmol of triisobutylaluminum. After elevating the temperature of the reaction system to 70° C., ethylene was fed to the system to keep a pressure of 1.5 kg/cm$^2$-G, and then propylene was fed to the system to keep a total pressure of 8 kg/cm$^2$-G. To the autoclave were added 0.3 mmol of methylaluminoxane and 0.001 mmol (in terms of Zr atom) of rac-dimethylsilyl-bis{1-(2-dimethyl-4-phenylindenyl)}zirconium dichloride to polymerize the monomers for 7 minutes while propylene was continuously fed to keep the total pressure of 8 kg//cm$^2$-G. After the polymerization, the autoclave was released, the resulting polymer was recovered in a large amount of methanol, and dried at 110° C. for 10 hours under reduced pressure.

The amount of the polymer obtained was 25.4 g. The polymerization activity was 25 kg-polymer/mmolZr.hr. The polymer had an ethylene content of 2.5 mol % and an intrinsic viscosity [η] of 3.1 dl/g. In the polymer, the triad tacticity of the propylene unit chain consisting of head-to-tail bonds was 97.6%, the proportion of the inversely inserted units based on the 2,1-insertion of the propylene monomer was 0.22%, and the proportion of the inversely inserted units based on the 1,3-insertion of the propylene monomer was not more than 0.05%.

The results are shown in Table 1 (i) and (II).

The film of the copolymer had a heat seal-starting temperature of 134° C. and a heat seal-starting temperature after heat treatment of 134° C.

The results are shown in Table 2.

Example 22

A 17-liter autoclave throughly purged with nitrogen was charged with 8 liters of hexane. After the temperature of the reaction system was elevated to 60° C., propylene and ethylene were continuously fed to the system at a flow rate of 250 liters/hr and a flow rate of 170 liters/hr, respectively, to elevate the pressure to 8 kg/cm$^2$-G.

Then, to the autoclave were added 8 mmol of triisobutylaluminum, 1.8 mmol of methylaluminoxane and 0.006 mmol (in terms of Zr atom) of rac-dimethylsilylbis{1-(2-dimethyl-4-phenylindenyl)}zirconium dichloride to polymerize the monomers at 60° C. for 45 minutes while a mixed gas of propylene and ethylene (mol ratio: 60/40) were continuously fed to keep the pressure of 8 kg//cm$^2$-G. After the polymerization, the autoclave was released, the resulting polymer was recovered in a large amount of methanol, and dried at 110° C. for 10 hours under reduced pressure.

The amount of the polymer obtained was 860 g. The polymerization activity was 143 kg-polymer/mmolZr.hr. The polymer had an ethylene content of 33.6 mol % and an intrinsic viscosity [η] of 1.4 dl/g. In the polymer, the triad tacticity of the propylene unit chain consisting of head-to-tail bonds was 97.5%, the proportion of the inversely inserted units based on the 2,1-insertion of the propylene monomer was 0.27%, and the proportion of the inversely inserted units based on the 1,3-insertion of the propylene monomer was not more than 0.03%.

The results are shown in Table 1 (I) and (II).

The copolymer had an izod impact strength of 30 kg.cm/cm, a film impact strength of 5300 kg.cm/cm and MFR of 17.8 g/10 min.

The results are shown in Table 2.

Example 23

The polymerization was carried out in the same manner as in Example 22 except that the feed of ethylene was changed to 60 liters from 170 liters, and the mol ratio of propylene to ethylene in the mixed gas was changed to 81/19 from 60/40.

The amount of the polymer obtained was 900 g. The polymerization activity was 150 kg-polymer/mmolZr.hr. The polymer had an ethylene content of 15.4 mol % and an intrinsic viscosity [η] of 1.5 dl/g. In the polymer, the triad tacticity of the propylene unit chain consisting of head-to-tail bonds was 96.7%, the proportion of the inversely inserted units based on the 2,1-insertion of the propylene monomer was 0.28%, and the proportion of the inversely inserted units based on the 1,3-insertion of the propylene monomer was not more than 0.03%.

The results are shown in Table 1 (I) and (II).

The film of the copolymer had a heat seal-starting temperature of 80° C. and a heat seal-starting temperature after heat treatment of 83° C.

The results are shown in Table 2.

Example 24

A 17-liter autoclave throughly purged with nitrogen was charged with 8 liters of hexane and 40 ml of hydrogen. After the temperature of the reaction system was elevated to 70° C., propylene and ethylene were continuously fed to the system at a flow rate of 253 liters/hr and a flow rate of 22 liters/hr, respectively, to elevate the pressure to 6.5 kg/cm²-G.

Then, to the autoclave were added 8 mmol of triisobutylaluminum, 1.8 mmol of methylaluminoxane and 0.006 mmol (in terms of Zr atom) of rac-dimethylsilylbis{1-(2-dimethyl-4-phenylindenyl)}zirconium dichloride to polymerize the monomers at 70° C. for 30 minuets while a mixed gas of propylene and ethylene (mol ratio: 92/8) was continuously fed to keep the pressure of 6.5 kg//cm²-G. After the polymerization, the autoclave was released, the resulting polymer was recovered in a large amount of methanol, and dried at 110° C. for 10 hours under reduced pressure.

The amount of the polymer obtained was 700 g. The polymerization activity was 117 kg-polymer/mmolZr.hr. The polymer had an ethylene content of 6.0 mol % and an intrinsic viscosity [η] of 2.0 dl/g. In the polymer, the triad tacticity of the propylene unit chain consisting of head-to-tail bonds was 97.5%, the proportion of the inversely inserted units based on the 2,1-insertion of the propylene monomer was 0.18%, and the proportion of the inversely inserted units based on the 1,3-insertion of the propylene monomer was not more than 0.03%.

The results are shown in Table 1 (I) and (II).

The film of the copolymer had a heat seal-starting temperature of 112° C. and a heat seal-starting temperature after heat treatment of 115° C.

The results are shown in Table 2.

TABLE 1 (I)

| | Comonomer | | Polymerization | | |
|---|---|---|---|---|---|
| | Kind | Content (%) | Yield (g) | Activity *1 | [η] (dl/g) |
| Ex. 2 | — | — | 51.3 | 4.02 | 3.37 |
| Ex. 3 | — | — | 60.7 | 31.1 | 3.01 |
| Comp. Ex. 1 | — | — | 4.7 | 2.4 | 4.05 |
| Ex. 4 | ethylene | 3.9 | 5.62 | 33.7 | 1.80 |
| Ex. 5 | ethylene | 8.7 | 6.63 | 39.8 | 1.66 |
| Ex. 6 | ethylene | 28.9 | 8.95 | 53.7 | 1.34 |
| Ex. 8 | — | — | 20.2 | 10.4 | 3.08 |
| Ex. 9 | ethylene | 7.9 | 2.08 | 12.5 | 1.39 |
| Ex. 14 | — | — | 23.4 | 12.0 | 2.92 |
| Ex. 15 | — | — | 24.6 | 12.6 | 3.05 |
| Ex. 16 | — | — | 19.9 | 10.2 | 3.13 |
| Ex. 17 | — | — | 14.5 | 7.4 | 3.47 |
| Ex. 18 | 1-butene | 20.2 | 52.1 | 149 | 1.90 |
| Ex. 19 | 1-octene | 6.7 | 5.4 | 5.4 | 1.44 |
| Ex. 20 | ethylene | 4.7 | 7000 | 117 | 2.7 |
| Ex. 21 | ethylene | 2.5 | 25.4 | 25 | 3.1 |
| Ex. 22 | ethylene | 33.6 | 860 | 143 | 1.4 |
| Ex. 23 | ethylene | 15.4 | 900 | 150 | 1.5 |
| Ex. 24 | ethylene | 6.0 | 700 | 117 | 2.0 |

*1: kg-polymer/mmol-Zr·hr

TABLE 1 (II)

| | | Proportion of inversely inserted units | | |
|---|---|---|---|---|
| | mm Fraction | 2,1-insertion (%) | 1,3-insertion (%) | Mw/Mn |
| Ex. 2 | 99.7 | 0.10 | <0.03 | 2.22 |
| Ex. 3 | 99.5 | 0.15 | <0.03 | 2.18 |
| Comp. Ex. 1 | 98.6 | 0.33 | <0.03 | 2.18 |
| Ex. 4 | 99.3 | 0.12 | <0.03 | 2.15 |
| Ex. 5 | 99.2 | 0.12 | <0.03 | 2.46 |
| Ex. 6 | 98.5 | 0.09 | <0.03 | 1.95 |
| Ex. 8 | 99.7 | 0.12 | <0.03 | 2.09 |
| Ex. 9 | 99.2 | 0.10 | <0.03 | 2.33 |
| Ex. 14 | 99.7 | 0.14 | <0.03 | 2.22 |
| Ex. 15 | 99.2 | 0.19 | <0.03 | 2.10 |
| Ex. 16 | 99.5 | 0.19 | <0.03 | 2.19 |
| Ex. 17 | 99.7 | 0.16 | <0.03 | 2.15 |
| Ex. 18 | — | — | — | 2.05 |
| Ex. 19 | — | — | — | 2.41 |
| Ex. 20 | 97.5 | 0.22 | <0.05 | — |
| Ex. 21 | 97.6 | 0.22 | <0.05 | — |
| Ex. 22 | 97.5 | 0.27 | <0.03 | — |
| Ex. 23 | 96.7 | 0.28 | <0.03 | — |
| Ex. 24 | 97.5 | 0.18 | <0.03 | — |

TABLE 2

| Example | Melting point (°C.) | Heat seal-starting temperature (°C.) | Heat seal-starting temperature after heat treatment (°C.) | Film impact strength (kg·cm/cm) | IZ of composition with polypropylene (kgf·cm/cm) | MFR of composition with polypropylene (g/10 min) |
|---|---|---|---|---|---|---|
| Ex. 4 | 126 | 129 | 132 | — | — | — |
| Ex. 5 | 105 | 106 | 109 | — | — | — |
| Ex. 6 | — | — | — | 5300 | 28 | — |
| Ex. 9 | 109 | 106 | 110 | — | — | — |
| Ex. 20 | 123 | 120 | 123 | — | — | — |

TABLE 2-continued

| Example | Melting point (°C.) | Heat seal-starting temperature (°C.) | Heat seal-starting temperature after heat treatment (°C.) | Film impact strength (kg-cm/cm) | IZ of composition with polypropylene (kgf-cm/cm) | MFR of composition with polypropylene (g/10 min) |
|---|---|---|---|---|---|---|
| Ex. 21 | 137 | 134 | 134 | — | — | — |
| Ex. 22 | — | — | — | 5300 | 30 | 17.8 |
| Ex. 23 | 78 | 80 | 83 | — | — | — |
| Ex. 24 | 115 | 112 | 115 | — | — | — |

What is claimed is:

1. A propylene homopolymer obtained by polymerizing propylene in the presence of an olefin polymerization catalyst comprising:

(A) a transition metal compound catalyst component represented by the following formula (I):

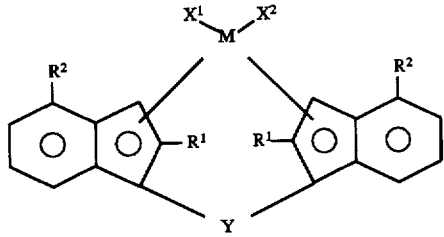

wherein
M is zirconium,
$R^1$ is an alkyl group of 2 to 4 carbon atoms,
$R^2$ is an aryl group selected from the group consisting of phenyl, naphthyl, anthracenyl and phenanthryl,
$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group; and
Y is a divalent silicon-containing group selected from the group consisting of alkylsilylene, alkylarysilylene and arylsilylene;

and (B) at least one compound selected from the group consisting of (B-1) an organoaluminum oxy-compound, and
(B-2) a compound which reacts with the transition metal compound to form an ion pair.

2. A propylene copolymer containing not less than 50% by mol of propylene unit, which is obtained by copolymerizing propylene and an α-olefin selected from the group consisting of ethylene and α-olefins of 4 to 20 carbon atoms in the presence of an olefin polymerization catalyst comprising:

(A) a transition metal compound catalyst component represented by the following formula (I):

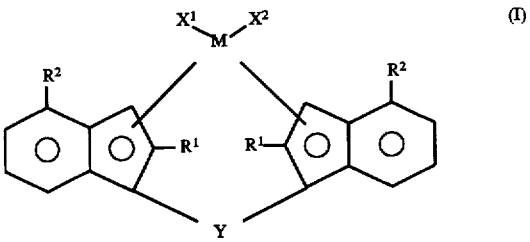

wherein
M is zirconium,
$R^1$ is an alkyl group of 2 to 4 carbon atoms,
$R^2$ is an aryl group selected from the group consisting of phenyl, naphthyl, anthracenyl and phenanthryl, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group; and
Y is a divalent silicon-containing group selected from the group consisting of alkylsilylene, alkylarylsilylene and arylsilylene;

and (B) at least one compound selected from the group consisting of (B-1) an organoaluminum oxy-compound, and
(B-2) a compound which reacts with the transition metal compound to form an ion pair.

* * * * *